US006262269B1

(12) United States Patent
Hayes et al.

(10) Patent No.: US 6,262,269 B1
(45) Date of Patent: Jul. 17, 2001

(54) 4-SUBSTITUTED-QUINOLINE DERIVATIVES AND 4-SUBSTITUTED-QUINOLINE COMBINATORIAL LIBRARIES

(75) Inventors: Thomas K. Hayes; Behrouz Forood; John S. Kiely, all of San Diego, CA (US)

(73) Assignee: Trega Biosciences, Inc., San Diego, CA (US)

( * ) Notice: Subject to any disclaimer, the term of this patent is extended or adjusted under 35 U.S.C. 154(b) by 0 days.

(21) Appl. No.: 09/017,785

(22) Filed: Feb. 3, 1998

Related U.S. Application Data
(60) Provisional application No. 60/126,414, filed on Feb. 4, 1997, now abandoned.

(51) Int. Cl.$^7$ ..................... C07D 215/06; C07D 401/04; C07D 407/04; C07D 409/04
(52) U.S. Cl. .................. 546/159; 546/165; 546/167; 546/171; 546/173
(58) Field of Search .................. 546/165, 167, 546/159, 171, 173

(56) References Cited

U.S. PATENT DOCUMENTS

| | | | | |
|---|---|---|---|---|
| 3,262,906 | * | 7/1966 | Perry ................................ | 260/45.8 |
| 3,910,918 | * | 10/1975 | Monroy ......................... | 260/283 SY |
| 5,767,129 | * | 6/1998 | Yuen ................................. | 514/307 |
| 5,856,503 | * | 1/1999 | Aebi et al. ............................ | 548/207 |
| 5,962,200 | * | 10/1999 | Taniguchi et al. .................. | 430/440 |

FOREIGN PATENT DOCUMENTS

| | | | |
|---|---|---|---|
| 462761 | * | 12/1991 | (EP) . |
| 0 634 169 | | 1/1995 | (EP) . |
| 95/11592 | * | 5/1995 | (WO) . |
| 96/33717 | | 10/1996 | (WO) . |

OTHER PUBLICATIONS

Bortolotti et al., "DDQ–Mediated Formation of Carbon––Carbon Bonds: Oxidation of Imines," *Tetrahedron*, 49(44) :10157–10174 (1993).
Gallop et al., "Applications of combinatorial technologies to drug discovery. 1. Background and peptide combinatorial libraries," *J. of Med. Chem.*, 37(9) :1233–1251 (April 29, 1994).
Gordon et al., "Applications of combinatorial technologies to drug discovery. 2. Combinatorial organic synthesis, library screening strategies, and future directions," *J. of Med. Chem.*, 37(10) :1385–1401 (May 13, 1994).
Leardini et al., "Annulation Reactions with Iron(III) Chloride: Oxidation of Imines," *J. Org. Chem.*, 57:1842–1848 (1992).
Leeson et al., "4–Amido–2–carboxytetrahydroquinolines, Structure Activity Relationships for Antagonism at the Glycine Site of the NMDA Receptor," *J. Med. Chem.*, 35:1954–1968 (1992).

Makioka et al., "Ytterbium (III) Triflate Catalyzed Synthesis of Quinoline Derivatives from N–Arylaldimines and Vinyl Ethers," *Synthesis*, 801–804 (1995).
Mellor and Merriman, "Reaction of Electron Rich Alkenes with Anilines and Formaldehyde: Syntheses of Tetrahydroquinolines," *Tetrahedron*, 51(21) :6115–6132 (1995).
Mellor et al., "Synthesis of Tetrahydroquinolines From Aromatic Amines, Formaldehyde and Electron Rich Alkenes: Evidence For Nonconcertedness," *Tetrahedron Letters*, 32(48) :7103–7106 (1991).
Nefzi et al., "The Current Status of Heterocyclic Combinatorial Libraries," *Chem. Rev.*, 97(2) :449–472 (1997).
Case et al., CA 57:9825g, 1962.*
Yamada, CA 58:4515f, 1963.*
Yun et al., CA 122:56707, 1995.*
Ryu et al., CA 118:233411, 1993.*
Ali et al., CA 118:102287, 1993.*
Rim et al., CA 119:181340, 1993.*
Spector et al., CA 123:218394, 1995.*
Dunn et al., CA 119:117598, 1993.*
Leardini et al., CA 117:26286, 1992.*
Friesen et al., CA 123:198641, 1995.*
Uchida et al., CA 112:198213, 1990.*
Atwell et al., CA 108:167271, 1988.*
Asaks et al., CA 94:15526, 1981.*
Echavarren et al., CA 109:55027, 1988.*
Gaspar et al., CA 108:167451, 1988.*
Leardini et al., CA 106:176141, 1987.*
Alford et al., CA 103:149982, 1985.*
LaMontagne et al., CA 88:284, 1978.*
Ciufolini et al., CA 124:87455, 1995.*
Desai et al., CA 112:228873, 1990.*
Uchida et al., CA 108:186740, 1988.*

(List continued on next page.)

*Primary Examiner*—Laura L. Stockton
(74) *Attorney, Agent, or Firm*—Law Office of David Spolter

(57) ABSTRACT

The present invention relates to novel 4-substituted quinoline compounds of the following formula, libraries containing such compounds, and to the generation of such combinatorial libraries composed of such compounds:

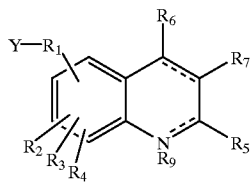

Formula I wherein $R^1$, $R^2$, $R^3$, $R^4$, $R^5$, $R^6$, $R^7$, $R^9$, and Y, have the meanings provided.

42 Claims, 5 Drawing Sheets

OTHER PUBLICATIONS

Hahn et al., CA 108:7509, 1988.*
Hirsch et al., CA 103:123375, 1985.*
Dienys et al., CA 87:53052, 1977.*
Nakahara et al., CA 126:19095, Oct. 1, 1996.*
Oku et al., CA 125:142578, 1996.*
Rauch, CA 76:61043, 1972.*
Kobayashi et al., "A new methodology for combinatorial synthesis. Preparation of diverse quinoline derivatives using a novel polymer–supported scandium catalyst," *J. Am. Chem. Soc.* 118:8977–8978 (1996).

* cited by examiner

Reaction Scheme I

Reaction Scheme III ant title="US 6,262,269 B1"

4-SUBSTITUTED-QUINOLINE DERIVATIVES AND 4-SUBSTITUTED-QUINOLINE COMBINATORIAL LIBRARIES

This application claims the benefit of priority of U.S. Provisional Application No. 60/126,414, filed Feb. 4, 1997, now abandonded which was converted from U.S. Ser. No. 08/795,392, filed Feb. 4, 1997, the entire contents of which is incorporated herein by reference.

BACKGROUND OF THE INVENTION

1. Field of the Invention

The present invention relates generally to the synthesis of heterocyclic compounds based on the 4-substituted quinoline ring. More specifically, the invention provides novel 4-substituted quinolines as well as novel libraries comprised of such compounds.

2. Background Information

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as 4-substituted quinolines.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such libraries and the rapid screening of the library which identifies lead pharmaceutical peptides.

Combinatorial approaches have recently been extended to "organic," or non-peptide, libraries. The organic libraries to the present, however, are of limited diversity and generally relate to peptidomimetic compounds; in other words, organic molecules that retain peptide chain pharmacophore groups similar to those present in the corresponding peptide.

Combinatorial chemical methods have been applied to a limited number of heterocyclic compounds, as described, for example, in U.S. Pat. No. 5,288,514 to Ellman, U.S. Pat. No. 5,324,483 to Cody et al. and Goff and Zuckermann, J. Org. Chem., 60:5748–5749 (1995)). Additionally, there is U.S. Pat. No. 5,549,974 to Holmes and U.S. Pat. No. 5,506,337 to Summerton and Weller. The patent application WO 94/08051 discloses the reaction of ether-linked aldehyde-derived imines with dihydrofuran under Lewis acid catalysis. The library, however, was limited to 108 compounds. However, the heterocyclic libraries to date contain compounds of limited diversity and complexity.

Leeson et al., J. Med. Chem., 35:1954 (1992), reported related tetrahydroquinolines as N-methyl-D-aspartate (NMDA) receptor site antagonists wherein the 2-position was by necessity a carboxy group, the 4position an acylated amine and two chlorine atoms present in the aromatic ring. In the one example employing N-vinylpyrrolidinone, Leeson et al. were limited to a stepwise procedure that required boron trifluoride as condensation agent. Mellor et al., Tetrahedron Letters 32:7103 (1991), described the use of 300 mole percent styrenes and formaldehyde with electron deficient anilines to prepare tetrahydroquinolines in modest yield but not free of the uncyclized adduct. This was modestly extended in Mellor and Merriman, Tetrahedron, 51:6115 (1995) but could not be halted at the single adduct stage except for electron withdrawn anilines.

Substituent limitations have been overcome for mixtures of peptides and peptidomimetics through the use of solid phase techniques versus solution-phase. An important step in the development of solid-phase techniques was the discovery of methods to identify active individual compounds from soluble mixtures of large numbers of compounds, as described, for example, by Rutter in U.S. Pat. No. 5,010,175 and Simon in WO PCT 91/19735. These soluble mixture methods, however, have rarely been applied to the syntheses of complex heterocyclic structures. There exists a need to develop more complex "organic" libraries based on heterocyclic medicinal compounds which would require less time and effort in the synthesis and testing needed to bring an organic pharmaceutical product to fruition. In short, improved methods for generating therapeutically useful heterocyclic compounds, such as -4-substituted quinoline derivatives, are desired.

This invention satisfies these needs and provides related advantages as well. The present invention overcomes the known limitations to classical organic synthesis of -4-substituted quinolines and as well as the shortcomings of combinatorial chemistry with heterocycles. The present invention combines the techniques of solid-phase synthesis of heterocycles and the general techniques of synthesis of combinatorial libraries to prepare new 4-substituted quinoline compounds.

SUMMARY OF THE INVENTION

The present invention relates to novel 4-substituted quinoline compounds of the following formula, libraries containing at least two or more such compounds, and to the generation of such combinatorial libraries composed of such compounds:

Formula I

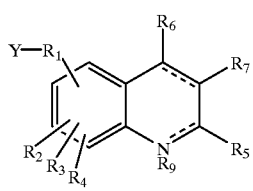

wherein $R^1$, $R^2$, $R^3$, $R^4$, $R^5$, $R^6$, $R^7$, $R^9$, and Y have the meanings provided below.

DETAILED DESCRIPTION OF THE INVENTION

Figure 1:
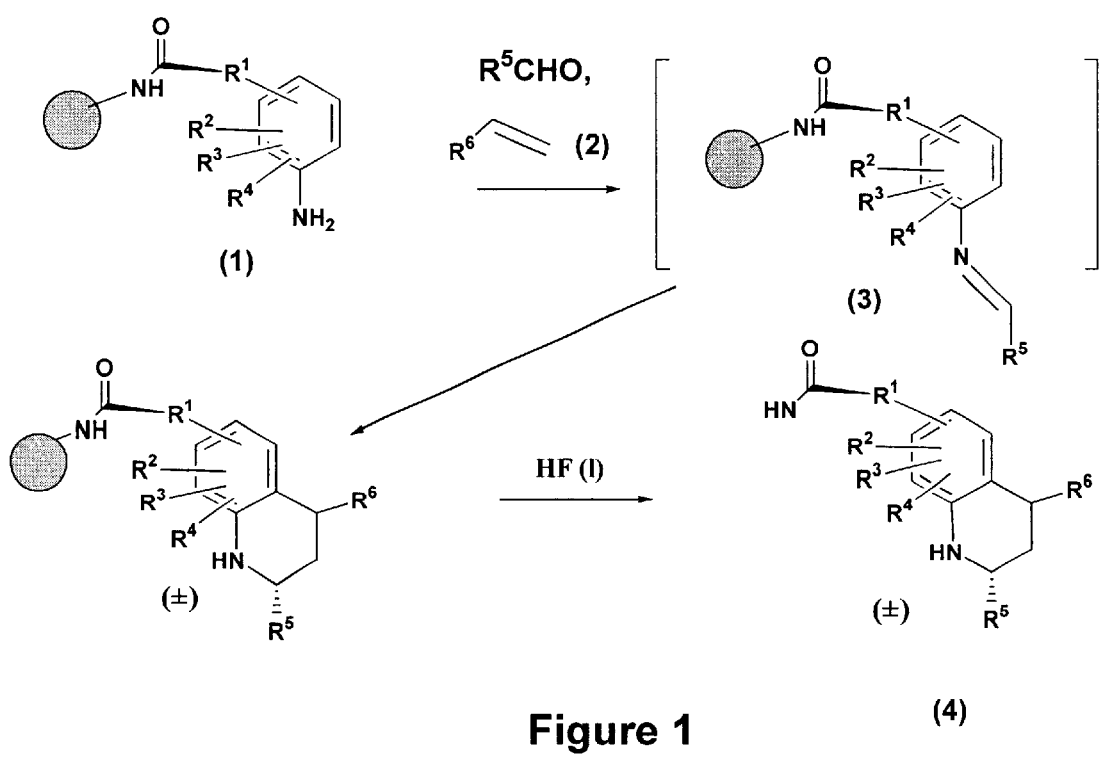
FIG. 1 provides Reaction Scheme I for preparing the 4-substituted quinoline compounds of the present invention.

The present invention provides novel derivatives and libraries of novel derivatives of variously substituted 4-substituted quinoline compounds of Formula I:

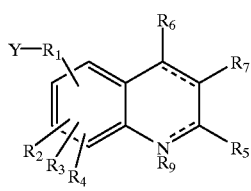

Formula I

In the above Formula I, the dashed lines ( - - - ) means fully saturated or fully unsaturated and when unsaturated, $R^9$ will be absent. Further, in the above Formula:

$R^1$ is absent or present and, when present, is $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —CH$_2$CONH— or a group of the formula:

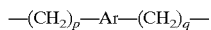

wherein p and q are independently selected from a number 0 to 6, wherein both p and q are not both 0; and Ar is an aryl group selected from the group consisting of phenyl, substituted phenyl, heteroaryl ring or substituted heteroaryl ring;

$R^2$, $R^3$, and $R^4$ are, independently, a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_1$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted) amino, (disubstituted)amino, carboxamide, protected carboxamide, $C_1$ to $C_4$ alkylthio, $C_1$ to $C_4$ substituted alkyltitio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl or substituted phenylsulfonyl;

$R^5$ is hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring or substituted heteroaryl ring;

$R^6$ is a phenyl, substituted phenyl, napthyl, substituted naphthyl, or a group of the formula:

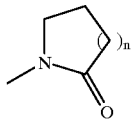

wherein n is from 1 to 4, or a group of the formula:

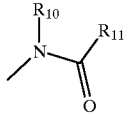

wherein $R_{10}$ and $R_{11}$ are, independently, selected from hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $_{R1}$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, or substituted phenylsulfonyl;

$R^7$ is a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, or substituted phenyl;

$R^9$ is a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, or substituted phenylaminocarbonyl; and Y is CO$_2$H, OH, SH, NHR$^{12}$, C(O)NHR$^{12}$, CH$_2$OH, CH$_2$NH$_2$, or CH$_2$NHR$^{12}$, wherein R$^{12}$ is a hydrogen atom, $C_1$ to $C_{10}$ alkyl, $C_1$ to $C_{10}$ substituted alkyl, or a functionalized resin, and more preferably, Y is CO$_2$H, NHR$^{12}$ or C(O)NHR$^{12}$ wherein R$^{12}$ is a hydrogen atom, $C_1$ to $C_{10}$ alkyl, $C_1$ to $C_{10}$ substituted alkyl, or a functionalized resin.

For $R^1$ defined above, p and q are independently selected from a number 0 to 6, wherein p and q are not both 0. Preferably, p and q are independently selected from 0 to 4 and, more preferably, from 0 to 3.

In another embodiment of the invention the 4-substituted quinoline compounds and libraries containing the same are wherein:

$R^1$ is absent or present and, when present, is $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, or a group of the formula: —$CH_2CONH$—;

$R^2$, $R^3$, and $R^4$ are, independently, a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, or nitro;

$R^5$ is hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring or substituted heteroaryl ring;

$R^6$ is a phenyl, substituted phenyl, napthyl, substituted naphphyl, or a group of the formula:

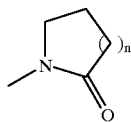

wherein n is from 1 to 2, or a group of the formula:

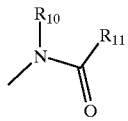

wherein $R_{10}$ and $R_{11}$ are, independently, selected from hydrogen, $C_1$ to $C_{10}$ alkyl, $C_1$ to $C_{10}$ substituted alkyl, phenyl, substituted phenyl, $C_7$ to $C_{12}$ phenylalkyl, or $C_7$ to $C_{12}$ substituted phenylalkyl;

$R^7$ is a hydrogen atom, $C_1$ to $C_{10}$ alkyl, or $C_1$ to $C_{10}$ substituted alkyl;

$R^9$ is a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, or substituted phenylaminocarbonyl; and Y is $CO_2H$, $NHR^{12}$ or $C(O)NHR^{12}$, wherein $R^{12}$ is a hydrogen atom, $C_1$ to $C_6$ alkyl, $C_1$ to $C_6$ substituted alkyl, or a functionalized resin, and more preferably, Y is $C(O)NHR^2$, wherein $R^{12}$ is a hydrogen atom, $C_1$ to $C_6$ alkyl, $C_1$ to $C_6$ substituted alkyl, or a functionalized resin.

In further embodiments of the invention, the R groups and Y are as defined above or below, provided that when $R^5$ is carboxy or carboalkoxy, $R^6$ is not N-pyrrolidinyl and/or that when $R^5$ is hydrogen and $R^2$, $R^3$, and/or $R^{R4}$ are nitro, R6 is not phenyl.

In yet another embodiment of this invention, the 4-substituted quinoline compounds and libraries containing the same are wherein:

$R^1$ is absent or present and, when present, is —$CH_2CONH$— or —$CH_2CH(NHR^8)$—, wherein $R^8$ is hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, aminocarbonyl, protected aminocarbonyl, (monosubstituted) aminocarbonyl, protected (monosubstitituted) aminocarbonyl, (disubstituted)aminocarbonyl, $C_1$ to $C_4$ alkylsulfonyl, $C_7$ to $C_{12}$ phenylalkylsulfonyl, phenylsulfonyl, or substituted phenylsulfonyl;

$R^2$, $R^3$, and $R^4$ are each, independently, a hydrogen atom, hydroxy, halo, $C_1$ to $C_6$ alkyl, $C_1$ to $C_7$ alkoxy, cyclic $C_2$ to $C_7$ alkylene, or nitro;

$R^5$ is a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_1$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring or substituted heteroaryl ring;

$R^6$ is a phenyl, substituted phenyl, or a group of the formula:

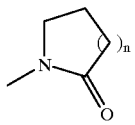

wherein n is from 1 to 2, or a group of the formula:

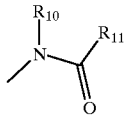

wherein $R_{10}$ and $R_{11}$ are, independently, selected from a hydrogen atom, $C_1$ to $C_{10}$ alkyl, $C_1$ to $C_{10}$ substituted alkyl, phenyl, or substituted phenyl;

$R^7$ is a hydrogen atom or $C_1$ to $C_{10}$ alkyl;

$R^9$ is a hydrogen atom; and

Y is $C(O)NH_2$ or $C(O)NH$ bound to a functionalized resin.

In a further embodiment, $R^1$ is absent or present, and when present is $CH_2NHCO$ or $CH_2CH(NHR^8)$, wherein $R^8$ is acetyln, α-cyclohexylphenylacetyl, α-methylcinnamoyl, α,α, α-trifluoro-m-toluoyl, α,α,α-trifluoro-o-toluoyl, α,α, α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrroleole-2-carboxyl, 4-fluoro-α-methylphenylacetyl, -4-fluorobenzoyl, 4-fluorophenylacetyl, tert-butylacetyl, tetrahydro-2-furoyl, tetrahydro-3-furoyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, xanthene-9-carboxyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4difluorobenzoyl, 4methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/-)-2-ethylhexanoyl, 2-fluorobenzoyl, 2-furyl, 4-hydroxyquinoline-2-carboxyl, (+/--2-methylbutyroyl, 2-methylcyclopropanecarboxyl, 2-naphthylacetyl, 2-napthoyl, 2-norbomaneacetyl, 2-phenylbutyroyl, 2-propylpentanoyl, 2-pyrazinecarboxyl, 2-thiopheneacetyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-imidazolecarboxyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-methyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl) propionoyl, heptanoyl, 3-benzoylpropionoyl, 3-bromobenzoyl, 3-bromophenylacetyl, chromone-2-carboxyl, 5-methyl-2-pyrazinecarboxyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methyliicotinoyl, 1-isoquinolinecarboxyl, lauryl, 3-methoxyphenylacetyl, 3-methyl-2-thiophenecarboxyl, 3-methylvaleroyl, 3-phenoxybenzoyl, 3-phenylbutyroyl, 3-thipheneacetyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, or 4-chlorobenzoyl;

$R^2$, $R^3$, and $R^4$ are each, independently, a hydrogen atom, hydroxy, fluoro, chloro, bromo, iodo, methyl, methoxy, nitro or —CH═CH—CH═CH— fused to adjacent positions;

$R^5$ is 1-methyl-2-pyrrolyl, 1-napthyl, 2,2-dimethyl-3-butenyl, 2,3,4-trifluorophenyl, 2,3,5-trichlorophenyl, 2,3-difluorophenyl, 1,2-methylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6fluorophenyl, 2-cyanophenyl, 3-pentyl, 2-fluorophenyl, 2-(3-(3-oxapropanoic acid))phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-chromonyl, 3-furyl, 3-hydroxy-4nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromo-2-thiophenyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-nitro-2-furyl, 5-norbonene-2-yl, 6-methyl-2-pyridinyl, 9-ethyl-3-carbazolyl, phenyl, chloromethyl, cyclohexanyl, D,L-1,2-(dihydroxy)ethyl, carboxy, hydrogen atom, acetyl, 2-hydroxyphenyl, tribromomethyl, tifluoro-p-tolulyl, or 2-methyl-2-propyl;

$R^6$ is 4-methoxyphenyl, 4-ethoxyphenyl, 3,4-dimethoxyphenyl, 2,4,5-trimethoxyphenyl, N-pyrrolidonyl, or N-methyl-N-acetyl-amino;

$R^7$ is a hydrogen atom or methyl;

$R^9$ is a hydrogen atom; and

Y is $C(O)NH_2$ or $C(O)NH$ bound to a functionalized resin.

In yet another embodiment, $R^1$ is $CH_2CH(NHR^8)$ wherein $R^8$ is acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tetrahydro-2-furoyl, tetrahydro-3-furoyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, xanthene-9-carboxyl, (2,5-dimethoxyphenyl)acetyl, (2-naphthoxy)acetyl, (3,4-dimethoxyphenyl)acety, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/−)-2-ethylhexanoyl, 2-fluorobenzoyl, 2-furyl, 4-hydroxyquinoline-2-carboxyl, (+/−)-2-methylbutyroyl, 2 -methylcyclopropanecarboxyl, 2-naphthylacetyl, 2-naptoyl, 2-norbornaneacetyl, 2-phenylbutyroyl, 2-propylpentanoyl, 2-pyrazinecarboxyl, 2-thiopheneacetyl, 3,3,3-triphenylpropionoyl, 3,3-phenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-imidazolecarboxyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl)propionoyl, heptanoyl, 3-benzoylpropionoyl, 3-bromobenzoyl, 3-bromophenylacetyl, chromone-2-carboxyl, 5-methyl-2-pyrazinecarboxyl, 3-chlorobenzoyl, 3-cyanobenzoyl, 3-cyclopentylpropionoyl, 3dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, 1-isoquinolinecarboxyl, lauryl, 3-methoxyphenylacetyl, 3-methyl-2-thiophenecarboxyl, 3-methylvaleroyl, 3-phenoxybenzoyl, 3-phenylbutyroyl, 3-thiopheneacetyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, or 4-chlorobenzoyl;

$R^2$, $R^3$, and $R^4$ are each, independently, a hydrogen atom;

$R^5$ is 1-methyl-2-pyrrolyl, 1-napthyl, 2,2-dimethyl-3-butenyl, 2,3,4-trifluorophenyl, 2,3,5-trichlorophenyl, 2,3-fluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-(3-oxapropanoic acid))phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5 -bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-chromonyl, 3-furyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromo-2-thiophenyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-nitro-2-furyl, 5-norbomene-2-yl, 6-methyl-2-pyiidinyl, 9-ethyl-3-carbazolyl, phenyl, chloromethyl, cyclohexanyl, D,L-1,2-(dihydroxy)ethyl, carboxy, hydrogen atom, acetyl, 2-hydroxyphenyl, tribromomethyl, trifluoro-ptolulyl, or 2-methyl-2-propyl;

$R^6$ is 4-methoxyphenyl, 4-ethoxyphenyl, 3,4-dimethoxyphenyl, 2,4,5-trimethoxyphenyl, N-pyrrolidonyl, or N-methyl-N-acetyl-amino;

$R^7$ is a hydrogen atom or methyl;

$R^9$ is a hydrogen atom; and

Y is $C(O)NH_2$ or C(O)NH bound to a functionalized resin.

In another embodiment, $R^1$ is absent or $CH_2NHCO$;

$R^2$, $R^3$, and $R^4$ are each, independently, a hydrogen atom, hydroxy, fluoro, chloro, bromo, iodo, methyl, methoxy, nitro or —CH═CH—CH═CH— fused to adjacent positions;

$R^5$ is 1-methyl-2-pyrrolyl, 1-napthyl, 2,2dimethyl-3-butenyl, 2,3,4-trifluorophenyl, 2,3,5-trichlorophenyl, 2,3-difluorophenyl, 1,2-dimethylbutyl, 2,4-dichlorophenyl, 2,5-difluorophenyl, 2,5-methylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-oxa-3-propionoyl)-phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-chromonyl, 3-furyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromo-2-thiophenyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-nitro-2-furyl, 5-norbornene-2-yl, 6-methyl-2-pyridinyl, 9-ethyl-3-carbazolyl, phenyl, chloromethyl, cyclohexanyl, D,L-1,2-(dihydroxy)ethyl, carboxy, hydrogen atom, acetyl, 2-hydroxyphenyl, tribromomethyl, trifluoro-p-tolulyl, or 2-methyl-2-propyl;

$R^6$ is 4-methoxyphenyl, 4-ethoxyphenyl, 3,4-dimethoxyphenyl, 2,4,5-trimethoxyphenyl, N-pyrolidonyl, or N-methyl-N-acetyl-amino;

$R^7$ is a hydrogen atom or methyl;
$R^9$ is a hydrogen atom; and
Y is $C(O)NH_2$ or C(O)NH bound to a functionalized resin.
In a further embodiment,
$R^1$ is absent or present and, when present, is selected from —$CH_2NHCO$— or $CH_2CH(NHR^8)$ wherein $R^8$ is acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrroleole-2-carboxyl, 4-fluoro-α-methylphenylacetyl, -4-fluorobenzoyl, 4-fluorophenylacetyl, tert-butylacetyl, tetrahydro-2-furoyl, tetrahydro-3-furoyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, xanthene-9-carboxyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorpheny)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/−)-2-ethylhexanoyl, 2-fluorobenzoyl, 2-furyl, 4-hydroxyquinoline-2-carboxyl, (+/−)-2-methylbutyroyl, 2-methylcyclopropanecarboxyl, 2-naphthylacetyl, 2-napthoyl, 2-norbomaneacetyl, 2-phenylbutyroyl, 2-propylpentanoyl, 2-pyrazinecarboxyl, 2-thiopheneacetyl, 3,3,3-triphenylpropionoyl, 3,3-phenylpropionoyl, 3,4,5-triethoxybenzoyl, 3,4,5-trimethoxybenzoyl, 3,4,5-tnimethoxycinnamoyl, 3,4-dichlorobenzoyl, 3,4-dichlorophenylacetyl, 3,4-difluorobenzoyl, 4-imidazolecarboxyl, 4-tert-butyl-cyclohexanecarboxyl, 3,4-dimethoxybenzoyl, 3,4-dimethylbenzoyl, 3,5,5-timethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl) propionoyl, heptanoyl, 3-benzoylpropionoyl, 3-bromobenzoyl, 3-bromophenylacetyl, chromone-2-carboxyl, 5-methyl-2-pyrazinecarboxyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, 1-isoquinolinecarboxyl, lauryl, 3-methoxyphenylacetyl, 3-methyl-2-thiophenecarboxyl, 3-methylvaleroyl, 3-phenoxybenzoyl, 3-phenylbutyroyl, 3-thiopheneacetyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, or 4-chlorobenzoyl;

$R^2$, $R^3$, and $R^4$ are each, independently, a hydrogen atom, hydroxy, fluoro, chloro, bromo, iodo, methyl, methoxy, nitro or —CH=CH—CH=CH— fused to adjacent positions;

$R^5$ is a hydrogen atom, phenyl, chloroacetyl, cyclohexanyl, D,L-1,2-(dihydroxy)ethyl, carboxy, acetyl, 2-hydroxyphenyl, tribromoacetyl, trimethylacetyl, 1-methyl-2-pyrrolyl, 1-napthyl, 2,3,4-trifluorophenyl, 2,3,5-trichlorophenyl, 2,3-difluorophenyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 2-ethylbutyryl, 2-fluorophenyl, 2-(2-oxymethylenecarboxy)phenyl, 2-methoxy-1-naphthyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-formylchromonyl, 3-furyl, 3-hydroxyphenyl, 3-nitro-4-chlorophenyl, 3-nitrophenyl, 3-phenoxyphenyl, 3-phenylbutyryl, 3-pyridinyl, 4-bromo-2-thiophenyl, 4-bromophenyl, 4-carboxyphenyl, 4-cyanophenyl, 4-fluorophenyl, 4-nitrophenyl, 4-pyridinyl, 4-quinolinyl, 5-bromo-2-hydroxyphenyl, 5-nitro-2-furyl, 5-norbornene-2-yl, 6-methyl-2-pyridinyl, 9-ethyl-3-carbazolyl, 2,3-dimethylvaleryl, 2,2-dimethyl-4-pentenyl, 3-methoxy-2-nitro-phenyl, 3-hydroxy-4-nitro-phenyl, 2-methylbutyryl, 2-methylvaleryl, 4-chloro-3-nitro-phenyl, 4-trifluromethyl)phenyl, 2-methylundecanyl, or β-phenylcinnaminyl;

$R^6$ is nalidixoyl, 2-phenyl-4-quinolinecarboxy, 2-pyrazinecarboxy, niflumoyl, 4-nitrophenylacetyl, 4-(4-nitrophenyl)butyroyl, (3,4-dimethoxyphenyl)-acetyl, 3,4-(methylenedioxy)phenylacetyl, 4-nitrocinnamoyl, 3,4,-(methylenedioxycinnamoyl, 3,4,5-trimethoxycinnamoyl, benzoyl, 2-chlorobenzoyl, 2-nitrobenzoyl, 2-(p-toluoyl)benzoyl, 2,4-dinitrophenylacetyl, 3-(3,4,5-trimethoxyphenyl)-propionyl, 4-biphenylacetyl, 1-napthylacetyl, (2-napthoxy)acetyl, trans-cinnamoyl, picolinyl, 3-amino-4-hydroxybenzoyl, (4-pyridylthio)acetyl, 2,4-dichlorobenzoyl, 3,4-dichlorobenzoyl, 4-biphenylcarboxy, thiophenoxyacetyl, 1-benzoylpropionyl, phenylacetyl, hydrocinnamoyl, 3,3-diphenylpropionyl, 3,3,3-triphenylpropionyl, 4-phenylbutyryl, phenoxyacetyl, (+/−)-2-phenoxypropionyl, 2,4-dimethoxybenzoyl, 3,4-dimethoxybenzoyl, 3,4-dihydroxybenzoyl, 2,4-dihydroxybenzoyl, 3,4,5-trimethoxybenzoyl, 3,4,5-triethoxybenzoyl, 3,4,5-trihydroxybenzoyl, 2-benzoylbenzoyl, 1-napthoyl, xanthene-9-carboxy, 4-chloro-2-nitrobenzoyl, 2-chloro-4-nitrobenzoyl, 4-chloro-3-nitrobenzoyl, 2-chloro-5-nitrobenzoyl, 4-dimethylaminobenzoyl, 4-(diethylamino)benzoyl, 4-nitrobenzoyl, 3-(dimethylamino)benzoyl, p-methylbenzoyl, p-methoxybenzoyl, trimethylacetyl, tert-butylacetyl, (−)-menthoxyacetyl, cyclohexanecarboxy, cyclohexylacetyl, dicyclohexylacetyl, 4-cyclohexylbutyroyl, cycloheptanecarboxy, 13-isopropylpodocarpa-7,13-dien-15-oyl, acetyl, octanoyl, (methylthio)acetyl, 3-nitropropionyl, 4-amino-3-hydroxybenzoyl, 3-(2-methyl-4-nitro-1-imidizoyl)propionyl, 2-furoyl, (s)(−)-2-pyrrolidone-5-carboxy, (2-pyrimidylthio)acetyl, 4-methoxy-2-quinolinecarboxy, 1-adamantanecarboxy, piperonoyl, 5-methyl-3-phenylisoxazole-4-carboxy, rhodanine-3-acetyl, 2-norbornaneacetyl, nicotinoyl, 9-oxo-9H-thioxanthene-3-carboxyl-10,10 dioxide, 2-thiophenecarboxy, 5-nitro-2-furanoyl, indole-3-acetyl, isonicotinoyl, 3α-hydroxy-5β-cholan-24-oyl, (3α,7α,12α)-trihydroxy-5β-cholan-24-oyl, (3α,5β-12α)-3,12, dihydroxy-5-cholan-24-oyl, (3α, 5β, 6α)-3, 6-dihydroxy-cholan-24-oyl, L-alaninyl, L-cysteinyl, L-aspartinyl, L-glutamninyl, L-phenylalaninyl, glycinyl, L-histidinyl, L-isoleucinyl, L-lyscinyl, L-leucinyl, L-methionylsulfoxide, L-methionyl, L-asparginyl, L-prolinyl, L-glutaminyl, L-arganinyl, L-serinyl, L-threoninyl, L-valinyl, L-tryptophanoyl, L-tyrosinyl, D-alaninyl, D-cysteinyl, D-aspartinyl, D-glutaminyl, D-phenylalaninyl, glycinyl, D-histidinyl, D-isoleucinyl, D-lyscinyl, D-leucinyl, D-methionylsulfoxide, D-methionyl, D-asparginyl, D-prolinyl, D-glutaminyl, D-arganinyl, D-serinyl, D-threoninyl, D-valiyl, D-tryptophanoyl, D-tyrosinyl, 2-aminobutyroyl, 4-aminobutyroyl, 2-aminoisobutyroyl, L-norieucinyl, D-norleucinyl, 6-aminohexanoyl, 7-aminoheptanoyl, thioprolinyl, L-norvalinyl, D-norvalinyl, α-ornithinyl, methionyl sulfonyl, L-naphthylalaninyl, D-naphthylalaninyl, L-phenylglycinyl, D-phenylglycinyl, β-alaninyl, L-cyclohexylalaninyl, D-cyclohexylalaninyl, hydroxyprolinyl, 4-nitrophenylalaninyl, dehydroprolinyl, 3-hydroxy-1-propanesulfonyl, 1-propanesulfonyl, 1-octanesulfonyl, perfluoro-1-octanesulfonly, (+)-10-camphorsulfonyl, (−)-10-camphorsulfonyl, benzenesulfonyl, 2-nitrobenzenesulfonyl, ptoluenesulfonyl, 4-nitrobenzenesulfonyl, n-acetylsulfanilyl, 2,5-dichlorobenzenesulfonyl, 2,4-dinitrobenzenesulfonyl, 2-mesitylenesulfonyl or 2-napthalenesulfonyl;

n is1; and

Y is $C(O)NH_2$ or C(O)NH bound to a funtionalized resin.

In the above Formula I, the $R^1$—Y substituents are such that Y is always bonded to the 1-position of the $R^1$ radical. All naming above and hereinafter reflects this positioning between the two substituents.

In the above Formula I, the stereochemistry of chiral centers associated with the $R^1$ through $R^{12}$ groups can independently be in the R or S configuration, or a mixture of the two. These can be designated as R or S or R,S or d,D, l,L or d,l, D,L.

In the above Formula I, the term "$C_1$ to $C_{10}$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_{10}$ alkyl" group is methyl.

The term "$C_2$ to $C_{10}$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_{10}$ alkylene" denotes such radicals as ethlynyl, propynyl, butynyl, pentynyl, hexynyl, heptynyl, as well as di- and tri-ynes of straight and branched chains.

The term "$C_1$ to $C_{10}$ alkylene" means a $C_1$ to $C_{10}$ alkyl group where the alkyl radical is bonded at two positions connecting together two separate additional groups. Examples of $C_1$ to $C_{10}$ alkylene include methylene, 1,2-ethyl, 1,1-ethyl, 1,3-propyl. The term "$C_2$ to $C_{10}$ alkenylene" means a $C_2$ to $C_{10}$ alkenyl radical which is bonded at two positions connecting together two separate additional groups.

The terms "$C_1$ to $C_{10}$ substituted alkyl," "$C_2$ to $C_{10}$ substituted alkenyl," and "$C_2$ to $C_{10}$ substituted alkynyl," denote that the above $C_1$ to $C_{10}$ alkyl groups and $C_2$ to $C_{10}$ alkenyl and alkynyl groups are substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_7$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$alkyl)carboxamide, cyano, methylsulfonylamino, thio, $C_1$ to $C_4$ alkylthio or $C_1$ to $C_4$ alkyl sulfonyl groups. The substituted alkyl, alkenyl or alkynyl groups may be substituted once or more, and preferably once or twice, with the same or with different substituents.

In preferred embodiments of the subject invention, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, or $C_2$ to $C_{10}$ substituted alkynyl and the like are preferably $C_1$ to $C_7$ or $C_2$ to $C_8$, respectively, and more preferably, $C_1$ to $C_6$ and $C_2$ to $C_7$. However, it would be appreciated by those of skill in the art that one or a few carbons could be added to an alkyl, alkenyl, alkynyl, substituted or unsubstituted, without substantially modifying the structure and function of the subject compounds and that, therefore, such additions would not depart from the spirit of the invention.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4dichloro(n-butyl), 2-aminopropyl, chloroethyl, bromoethyl, fluoroethyl, iodoethyl, chloropropyl, bromopropyl, fluoropropyl, iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "$C_1$ to $C_{10}$ substituted alkylene" means a $C_1$ to $C_{10}$ alkyl group where the alkyl radical is bonded at two positions connecting together two separate additional groups and further bearing an additional substituent. Examples of $C_1$ to $C_{10}$ substituted alkylene includes aminomethylene, 1-(amino)-1,2-ethyl, 2-(amino)-1,2-ethyl, 1-(acetamido)-1,2-ethyl, 2-(acetamido)-1,2-ethyl, 2-hydroxy-1,1-ethyl, 1-(amino)-1,3-propyl. Similarly, the term "$C_2$ to $C_{10}$ substituted alkenylene" means a $C_2$ to $C_{10}$ substituted alkenyl group where the alkenyl radical is bonded at two positions connecting together two separate additional groups and further bearing an additional substituent.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_7$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_7$ substituted alkoxy" means the alkyl portion of the alkoxy can be substituted in the same manner as in relation to $C_1$ to $C_6$ substituted alkyl.

The term "$C_1$ to $C_7$ acyloxy" denotes herein groups such as formyloxy, acetoxy, propionyloxy, butyryloxy, pentanoyloxy, hexanoyloxy, heptanoyloxy and the like.

Similarly, the term "$C_1$ to $C_7$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "$C_1$ to $C_7$ substituted acyl" denotes the acyl group substituted by one or more, and preferably one or two, halogen, hydroxy, protected hydroxy, oxo, protected oxo, cyclohexyl, naphthyl, amino, protected amino, (monosubstituted)amino, protected (monosubstituted) amino, (disubstituted)amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_7$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, NN-di($C_1$ to $C_6$ alkyl)carboxamide, cyano, methylsulfonylamino, thio, $C_1$ to $C_4$ alkylthio or $C_1$ to $C_4$ alkyl sulfonyl groups. The substituted acyl groups may be substituted once or more, and preferably once or twice, with the same or with different substituents.

Examples of $C_1$ to $C_7$ substituted acyl include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by one or two halogen, hydroxy, protected hydroxy, $C_1$ to $C_6$ alkyl, $C_1$ to $C_7$ alkoxy, oxo, protected oxo, (monosubstituted)amino, (disubstituted)amino, trifluoromethyl, carboxy, protected carboxy, phenyl, substituted phenyl, amino, or protected amino groups.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "$C_5$ to $C_7$ substituted cycloalkenyl" denotes the above $C_5$ to $C_7$ cycloalkenyl rings substituted by a $C_1$ to $C_6$ alkyl radical, halogen, hydroxy, protected hydroxy, $C_1$ to $C_7$ alkoxy, trifluoromethyl, carboxy, protected carboxy, oxo, protected oxo, (monosubstituted)amino, protected (monosubstituted) amino, (disubstituted)amino, phenyl, substituted phenyl, amino, or protected amino.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be saturated, fully saturated or partially unsaturated, with fully saturated rings being preferred. A "substituted heterocyclic ring" means any of the above-described heterocycles substituted with any of the substituents as referred to above in relation to substituted phenyl. An "amino-substituted heterocyclic ring" means any one of the above-described heterocyclic rings is substituted with at least one amino group. Preferred heterocyclic rings include morpholino, piperidinyl, piperazinyl, tetrahydrofurano, pyrrolo, and tetrahydrothiophen-yl.

The abbreviation "Ar" stands for an aryl group. Aryl groups which can be used with present invention include phenyl, substituted phenyl, as defined above, heteroaryl, and substituted heteroaryl. The term "heteroaryl" or "heteroaryl ring" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, thiazolo and the like.

The term "substituted heteroaryl" or "substituted heteroaryl ring" means the above-described heteroaryl is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino carboxamide, protected carboxamide, N—($C_1$ to $C_6$alkyl) carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino or N-(phenylsulfonyl) amino groups.

The term "$C_7$ to $C_{12}$ phenylalkyl" denotes a $C_1$ to $C_6$ alkyl group substituted at any position by a phenyl ring. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, (monosubstituted) amino, protected (monosubstituted)amino, (disubstituted) amino, guanidino, heterocyclic ring, substituted heterocyclic ring, $C_1$ to $C_7$ alkoxy, $C_1$ to $C_7$ substituted alkoxy, $C_1$ to $C_7$ acyl, $C_1$ to $C_7$ acyloxy, nitro, carboxy, protected carboxy, carbamoyl, carboxamide, protected carboxamide, N—($C_1$ to $C_6$ alkyl)carboxamide, protected N—(($C_1$ to $C_6$ alkyl)

carboxamide, N,N—($C_1$ to $C_6$ dialkyl)carboxamide, cyano, N—(($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl protected hydroxymethyl, amino, protected amino, (monosubstituted) amino, protected (monosubstituted)amino, (disubstituted) amino, carboxamide, protected carboxamide, N—($C_1$ to $C_6$ alkyl)carboxamide, protected N—($C_1$ to $C_6$ alkyl) carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino, cyclic $C_2$ to $C_7$ alkylene or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxyphenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N—($C_1$ to $C_6$ alkyl)carboxamide, protected N—($C_1$ to $C_6$ alkyl) carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl results.

Examples of the term substituted phenyl include a mono- or di-halo)phenyl group such as 2, 3 or 4-chlorophenyl, 2,6dichlorophenyl, 2,5-dichlorophenyl, 3,4-dichlorophenyl, 2, 3 or 4bromophenyl, 3,4-dibromophenyl, 3-chloro-4-fluorophenyl, 2, 3 or 4fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "phenylene" means a phenyl group where the phenyl radical is bonded at two positions connecting together two separate additional groups. Examples of "phenylene" include 1,2-phenyl, 1,3-phenyl, and 1,4-phenyl.

The term "substituted phenylene" means a phenyl group where the phenyl radical is bonded at two positions connecting together two separate additional groups. Examples of substituted phenylene include 3-chloro-1,2-phenyl, 4-amino-1,3-phenyl, and 3-hydroxy-1,4-phenyl.

The term "phenoxy" denotes a phenyl bonded to an oxygen atom provided that the phenoxy is bonded to the quinoline ring through the oxygen atom as opposed to a carbon atom of the phenyl ring. The term "substituted phenoxy" specifies a phenoxy group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkylicarboxamide, trifluoromethyl, N—(($C_1$ to $C_6$ alkyl)sulfonyl)amino and N-(phenylsulfonyl) amino.

Examples of substituted phenoxy include 2-methylphenoxy, 2-ethylphenoxy, 2-propylphenoxy, 2-isopropylphenoxy, 2-sec-butylphenoxy, 2-tert-butylphenoxy, 2-allylphenoxy, 2-propenylphenoxy, 2-cyclopentylphenoxy, 2-fluorophenoxy, 2-(trifluoromethyl) phenoxy, 2-chlorophenoxy, 2-bromophenoxy, 2-methoxyphenoxy, 2-ethoxyphenoxy, 2-isopropoxyphenoxy, 3-methylphenoxy, 3-ethylphenoxy, 3-isopropylphenoxy, 3-tert-butylphenoxy, 3-pentadecylphenoxy, 3-(trifluoromethyl)phenoxy, 3-fluorophenoxy, 3-chlorophenoxy, 3-bromophenoxy, 3-iodophenoxy, 3-methoxyphenoxy, 3-(trifluoromethoxy) phenoxy, 4-methylphenoxy, 4-ethylphenoxy, 4-propylphenoxy, 4-isopropylphenoxy, 4-sec-butylphenoxy, 4-tert-butylphenoxy, 4-tert-amylphenoxy, 4-nonylphenoxy, 4-dodecylphenoxy, 4-cyclopenylphenoxy, 4-(trifluoromethyl)phenoxy, 4-fluorophenoxy, 4-chlorophenoxy, 4-bromophenoxy-4-iodophenoxy, 4-methoxyphenoxy, 4-(trifluoromethoxy)phenoxy, 4-ethoxyphenoxy, 4-propoxyphenoxy, 4-butoxyphenoxy, 4-hexyloxyphenoxy, 4-heptyloxyphenoxy, 2,3-dimethylphenoxy, 5,6,7,8-tetrahydro-1-naphthoxy, 2,3-dichlorophenoxy, 2,3-dihydro-2,2-dimethyl-7-benzofuranoxy, 2,3-dimethoxyphenoxy, 2,6-dimethylphenoxy, 2,6-diisopropylphenoxy, 2,6-di-sec-butylphenoxy, 2-tert-butyl-6-methylphenoxy, 2,6-di-tert-butylphenoxy, 2-allyl-6-methylphenoxy, 2,6-difluorophenoxy, 2,3-difluorophenoxy, 2,6-dichlorophenoxy, 2,6-dibromophenoxy, 2-fluoro-6methoxyphenoxy, 2,6-dimethoxyphenoxy, 3,5-dimethylphenoxy, 5-isopropyl-3-methylphenoxy, 3,5-di-tert-butylphenoxy, 3,5 -bis(trifluoromethyl)phenoxy, 3,5- difluorophenoxy, 3,5-dichlorophenoxy, 3,5-dimethoxyphenoxy, 3-chloro-5-methoxyphenoxy, 3,4-dimethylphenoxy, 5-indanoxy, 5,6,7,8-tetrahydro-2-naphthoxy, 4-chloro-3-methylphenoxy, 2,4-dimethylphenoxy, 2,5-dimethylphenoxy, 2-isopropyl-5-methylphenoxy, 4-isopropyl-3-methylphenoxy, 5-isopropyl-2-methylphenoxy, 2-tert-butyl-5-methylphenoxy, 2-tert-butyl-4-methylphenoxy, 2,4-di-tert-butylphenoxy, 2,4-di-tert-amylphenoxy, 4-fluoro-2-methylphenoxy, 4-fluoro-3-methylphenoxy, 2-chloro-4-methylphenoxy, 2-chloro-5-methylphenoxy, 4-chloro-2-methylphenoxy, 4-chloro-3-ethylphenoxy, 2-bromo-4-methylphenoxy, 4-iodo-2-methylphenoxy, 2-chloro-5-(trifluoromethyl)phenoxy, 2,4-difluorophenoxy, 2,5-difluorophenoxy, 3,4-difluorophenoxy, 4-chloro-2-fluorophenoxy, 3-chloro-4-fluorophenoxy, 4-chloro-3-fluorophenoxy, 2-bromo-4-fluorophenoxy, 4-bromo-2-fluorophenoxy, 2-bromo-5-fluorophenoxy, 2,4-dichlorophenoxy, 3,4dichlorophenoxy, 2,5-dichlorophenoxy, 2-bromo-4-chlorophenoxy, 2-chloro-4-fluorophenoxy, 4-bromo-2-chlorophenoxy, 2,4-dibromophenoxy, 2-methoxy-4-methylphenoxy, 4-allyl-2-methylphenoxy, trans-2-ethoxy-5-(1-propenyl)phenoxy, 2-methoxy-4-propenylphenoxy, 3,4-dimethoxyphenoxy, 3-ethoxy-4-methoxyphenoxy, 4-allyl-2,6-dimethoxyphenoxy, 3,4-methylenedioxyphenoxy, 2,3, trimethylphenoxy, 2,4-dichloro-3-methylphenoxy, 2,3,4-trifluorophenoxy, 2,3,6-trifluorophenoxy, 2,3,5-trifluorophenoxy, 2,3,4-trichlorophenoxy, 2,3,6-trichlorophenoxy, 2,3,5-trimethylphenoxy, 3,4,5-trimethylphenoxy, 4-chloro-3,5-dimethylphenoxy, 4-bromo-3,5-dimethylphenoxy, 2,4,6-trimethylphenoxy, 2,6-bis(hydroxymethyl)-4-methylphenoxy, 2,6-di-tert-butyl-4-methylphenoxy, 2,6-di-tert-butylmethoxyphenoxy, 2,4,5-trifluorophenoxy, 2-chloro-3,5-difluorophenoxy, 2,4,6-trichlorophenoxy, 3,4,5-trimethoxyphenoxy, 2,3,5-trichlorophenoxy, 4-bromo-2,6-dimethylphenoxy, 4-bromo-6-chloro-2-methylphenoxy, 2,6-dibromo-4-methylphenoxy, 2,6dichloro-4-fluorophenoxy, 2,6-dibromo-4-fluorophenoxy, 2,4,6-tribromophenoxy, 2,4,6-triiodophenoxy, 2-chloro-4,5-dimethylphenoxy, 4-chloro-2-isopropyl-5-methylphenoxy, 2-bromo-4,5-difluorophenoxy, 2,4,5-trichlorophenoxy, 2,3,5,6-tetrafluorophenoxy and the like.

The term "$C_7$ to $C_{12}$ phenylalkoxy" denotes a $C_7$ to $C_{12}$ phenylalkoxy group, provided that the phenylalkoxy is bonded to the quinoline ring through the oxygen atom. By "$C_7$ to $C_{12}$ substituted phenylalkoxy" is meant $C_7$ to $C_{12}$ phenylalkoxy group which can be substituted on the $C_1$ to $C_6$ alkyl portion with one or more, and preferably one or two, groups chosen from halogen, hydroxy, protected hydroxy, oxo, protected oxo, amino, protected amino, (monosubstituted)amino, protected (monosubstituted)amino, (disubstituted)amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N—($C_1$ to $C_6$ alkyl)carboxamide, protected N—($C_1$ to $C_6$ alkyl) carboxamide, N,N—($C_1$ to $C_6$ dialkyl)carboxamide, cyano, N—(($C_1$ to $C_6$ alkylsulfonyl)amino, thiol, $C_1$ to $C_4$ alkylthio, $C_1$ to $C_4$ alkylsulfonyl groups; and/or the phenyl group can be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl) amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkoxy" include groups such as 2-(4-hydroxyphenyl)ethoxy, 4-(4-methoxyphenyl)butoxy, (2R)-3-phenyl-2-amino-propoxy, (2S)-3-phenyl-2-amino-propoxy, 2-indanoxy, 6-phenyl-1-hexanoxy, cinnamyloxy, (+/−)-2-phenyl-1-propoxy, 2,2-dimethyl-3-phenyl-1-propoxy and the like.

The term "phthalimide" means a cyclic imide which is made from phthalic acid, also called 1, 2 benezene-dicarboxylic acid. The term "substituted phthalimide" specifies a phthalimide group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ ally)carboxamide, N,N-di($C_1$ to $C_6$ alkyl)carboxamide, trifluoromethyl, N—(($C_1$ to $C_6$ alkyl)sulfonyl)amino and N-(phenylsulfonyl) amino.

Examples of substituted phthalimides include 4,5-dichlorophthalimido, 3-fluorophthalimido, 4-methoxyphthalimido, 3-methylphthalimido, 4-carboxyphthalimido and the like.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$alkyl)carboxamide, N,N-di($C_1$ to $C_6$ alkyl)carboxamide, trifluoromethyl, N—(($C_1$ to $C_6$ alkyl)sulfonyl)amino or N-(phenylsulfonyl) amino.

Examples of substituted naphthyl include a mono or di(halo)naphthyl group such as 1, 2, 3, 4, 5, 6, 7 or 8-chloronaphthyl, 2, 6dichloronaphthyl, 2,5-dichloronaphthyl, 3,4-dichloronaphthyl, 1, 2, 3, 4, 5, 6, 7 or 8-bromonaphthyl, 3,4 -dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy)

naphthyl group, for example, 2,6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy) naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2,4-di(-protected carboxy) naphthyl; a mono- or di(hydroxymethyl)naphthyl or (protected hydroxymethyl)naphthyl such as 1, 2, 3, 4, 5, 6, 7 or 8-(protected hydroxymethyl)naphthyl or 3,4-di (hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)napbthyl such as 2, 3, or 4-(aminomethyl) naphthyl or 2,4-(protected aminomethyl)-naphthyl; or a mono- or di-(N-methylsulfonylamino)naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The terms "halo" and "halogen" refer to the fluoro, chloro, bromo or iodo groups. There can be one or more halogen, which are the same or different. Preferred halogens are chloro and fluoro.

The term "(monosubstituted)amino" refers to an amino group with one substituent chosen from the group consisting of phenyl, substituted phenyl, $C_1$ to $C_6$ alkyl $C_1$ to $C_6$ substituted alkyl, $C_1$ to $C_7$ acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl and heterocyclic ring. The (monosubstituted)amino can additionally have an amino-protecting group as encompassed by the term "protected (monosubstituted)amino."

The term "(disubstituted)amino" refers to amino groups with two substituents chosen from the group consisting of phenyl, substituted phenyl, $C_1$ to $C_6$ alkyl, $C_1$ to $C_6$ substituted alkyl $C_1$ to $C_7$ acyl, $C_2$ to $C_7$ alkenyl, $C_2$ to $C_7$ alkynyl, $C_7$ $C_{12}$ phenylalkyl, and $C_7$ to $C_{12}$ substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the (monosubstituted)amino nitrogen atom. In addition, the term "protected carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5 -dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy) benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetralydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting group is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydoxymethyl" which refer to a hydroxy or hydroxymethyl substituted with one of the above hydroxy-protecting groups.

The substituent term "$C_1$ to $C_4$ alkylthio" refers to sulfide groups such as melthylthio, ethylthio, n-propylthio, isopropylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "$C_1$ to $C_4$ alkylsulfonyl" encompasses groups such as methylsulfonyl, ethylsulfonyl, n-propylsulfonyl, isopropylsulfonyl, n-butylsulfonyl, t-butylsulfonyl and the like.

The terms "$C_1$ to $C_4$ substituted alkylthio," "$C_1$ to $C_4$ substituted alkylsulfoxide," and "$C_1$ to $C_4$ substituted alkylsulfonyl" denote the $C_1$ to $C_4$ alkyl portion of these groups may be substituted as described above in relation to "substituted alkyl."

The terms "phenylthio,""phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" mean that the phenyl of these groups can be substituted as described above in relation to "substituted phenyl."

The term "$C_1$ to $C_6$ alkylaminocarbonyl" means a $C_1$ to $C_6$ alkyl attached to an aminocarbonyl group, where the $C_1$ to $C_6$ alkylaminocarbonyl groups are the resulting urea when an isocyanate is used in the reaction scheme. Examples of $C_1$ to $C_6$ alkylaminocarbonyl include methylaminocarbonyl (from methylisocyanate), ethylaminocarbonyl (from ethylisocyanate), propylaminocarbonyl (from propylisocyanate), butylaminocarbonyl (from butylisocyatate). The term "$C_1$ to $C_6$ substituted alkylaminocarbonyl" denotes a substituted alkyl bonded to an aminocarbonyl group, which alkyl may be substituted as described above in relation to $C_1$ to $C_6$ substituted alkyl. Examples of $C_1$ to $C_6$ substituted alkylaminocarbonyl include, for example, methoxymethylaminocarbonyl (from methoxymethylisocyanate), 2-chloroethylaminocarbonyl (from 2-chloroethylisocyanate), 2-oxopropylaminocarbonyl (from 2-oxopropylisocyanate), and 4-phenylbutylaminocarbonyl (from phenylbutylisocyanate).

The term "phenylaminocarbonyl" means a phenyl attached to an aminocarbonyl group, where the phenylaminocarbonyl groups are the result of using a phenylisocyanate in the reaction scheme. The term "substituted phenylaminocarbonyl" denotes a substituted phenyl bonded to an aminocarbonyl group, which phenyl may be substituted as described above in relation to substituted phenyl. Examples of substituted phenylaminocarbonyl include 2-chlorophenylaminocarbonyl (from 2-chlorophenylisocyanate), 3-chlorophenylaminocarbonyl (from 3-chlorophenylisocyanate), 2-nitorphenylaminocarbonyl (from 2-nitrophenylisocyanate), 4-biphenylaminocarbonyl (from 4-biphenylisocyanate), and 4methoxyphenylaminocarbonyl (from 4-methoxyphenylisocyanate).

The substituent terms "cyclic $C_2$ to $C_7$ alkylene," substituted cyclic $C_2$ to $C_7$ alkylene," "cyclic $C_2$ to $C_7$ heteroalkylene," and "substituted cyclic $C_2$ to $C_7$ heteroalkylene" define such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ to $C_7$ heteroalkylene.

The cyclic alkylene or heteroalkylene group may be substituted once or twice by the same or different substituents selected from the group consisting of the following moieties: hydroxy, protected hydroxy, carboxy, protected carboxy, oxo, protected oxo, $C_1$ to $C_4$ acyloxy, formyl, $C_1$ to $C_7$ acyl, $C_1$ to $C_6$ alkyl, $C_1$ to $C_7$ alkoxy, $C_1$ to $C_4$ alkylthio, $C_1$ to $C_4$ alkylsulfoxide, $C_1$ to $C_4$ alkylsulfonyl, halo, amino, protected amino, (monosubstituted)amino, protected (monosubstituted)amino, (disubstituted)amino, hydroxymethyl and a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the phenyl is fused to a pyridino, pyrano, pyrrolo, pyridinyl, dihydropyrrolo, or dihydropyridinyl ring. Examples of fused cyclic groups which each contain one oxygen atom and one or two double bonds are when the phenyl ring is fused to a furo, pyrano, dihydrofurano, or dihydropyrano ring. Examples of fused cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

One or more of the 4-substituted quinoline derivatives, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1–19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_3$ is substituted with a (quaternary ammonium) methyl group. A preferred cation for the carboxylate anion is the sodium cation.

The compounds of the above Formulae can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more 4-substituted quinoline derivatives, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the α-($C_1$ to $C_7$) alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-diooxlen-4-ylmethyl, 5-phenyl-2-oxo-1,3-diooxlen-4-ylmethyl and the like; the $C_1$ to $C_4$ alkylthiomethyl groups, for example methylthiomethyl, ethylthiomethyl, iso-propylthiomethyl and the like; the acyloxymethyl groups, for example pivaloyloxymethyl, pivaloyloxyethyl, α-acetoxymethyl and the like; the ethoxycarbonyl-1-methyl group; the α-acetoxyethyl; the 1-($C_1$ to $C_7$ alkyloxycarbonyloxy)ethyl groups such as the 1-(ethoxycarbonyloxy)ethyl group; and the 1-($C_1$ to $C_7$ alkylaminocarbonyloxy)ethyl groups such as the 1-(methylaminocarbonyloxy)ethyl group.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("NMe"), norvaline ("Nva"), β-Alanine, L- or D-naphthalanine, omithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration or the D-amino acid can readily be substituted for that in the L-configuration.

As used herein, a chemical or combinatorial "library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). The libraries can be screened in any variety of assays, such as those detailed below as well as others useful for assessing the biological activity. The libraries are usefull in their ability to rapidly synthesize and screen a diverse number or compounds. Moreover, the libraries will generally have at least one active compound and are generally prepared in such that the compounds are in equimolar quantities.

"Combinatorial chemistry" or "combinatorial synthesis" refers to the parallel synthesis of diverse compounds by sequential addition of reagents which leads to the generation of large chemical libraries having molecular diversity. Combinatorial chemistry, therefore, involves the systematic and repetitive, covalent connection of a set of different "building blocks" of varying structures to yield large arrays of diverse molecular entities.

The compounds of Formula I and combinatorial libraries containing the same can be prepared as set forth in the Reaction Schemes provided in the Figures and described below. The substituents $R^1$ to $R^9$ in the Reaction Schemes have the same meaning as those described above. The substituent Y in the Reaction Schemes is the same as defined above with the exception that it is still bound to resin or is the functionalized resin and, therefore, has one less hydrogen.

In brief, the 4-substituted quinoline compounds of the present invention can be prepared according to Reaction Scheme I as shown in FIG. 1. As depicted in FIG. 1, a solid support resin-bound aniline (1) (resin identified by a shaded circle) is reacted, in situ, with an aldehyde (2) and is thereby, converted to the corresponding imine (3). This is performed in the presence of a dieneophile and an acid. In the presence of the dieneophile, the imine(3) undergoes a hetero-Diels-Alder-like reaction and yields the 4-substituted tetrahydro-quinoline (4).

Figure 2:
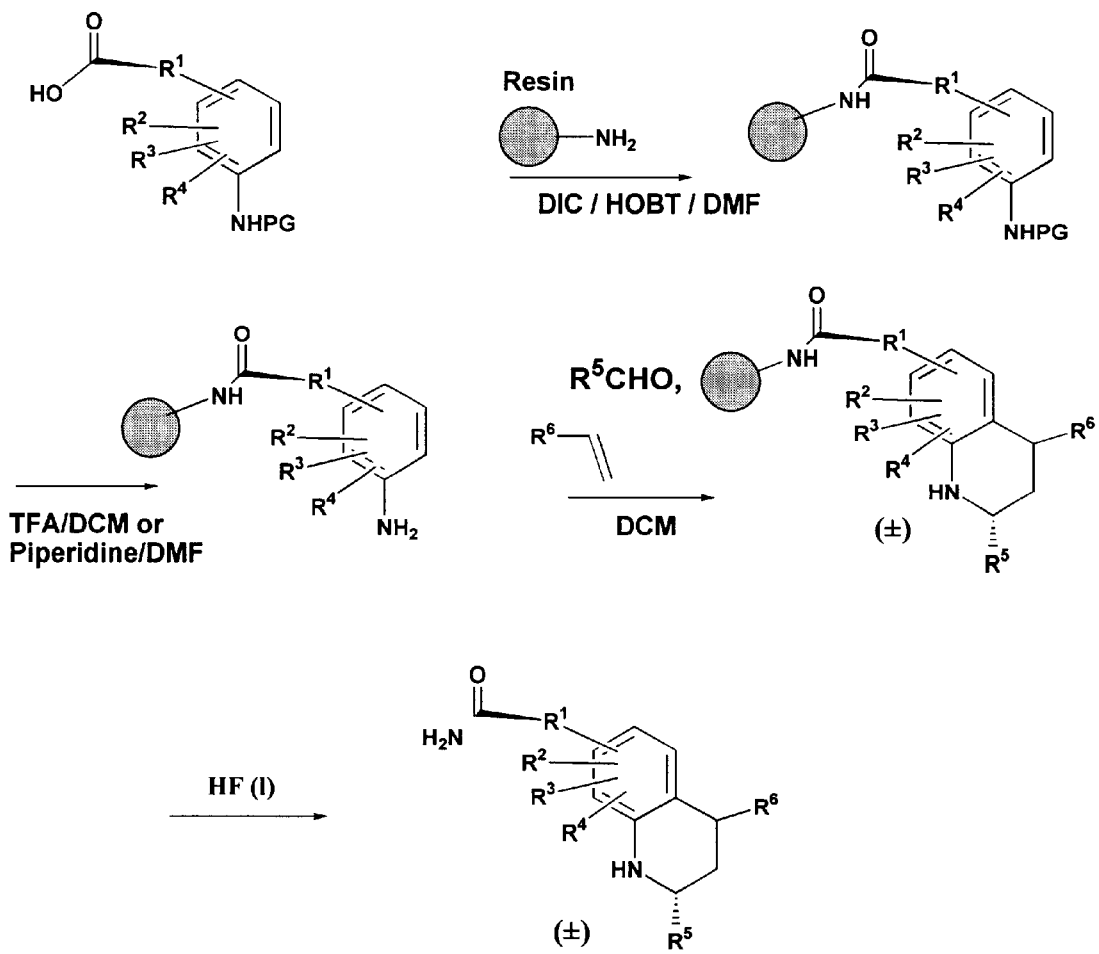
FIG. 2 shows a more detailed reaction scheme, Reaction Scheme II, for the preparation of the subject 4-substituted quinolines and libraries containing the same.

More specifically, as shown by Reaction Scheme II in FIG. 2, the 4-substituted quinolines and libraries containing the same are prepared by the following more detailed steps. First, the anilines, (as shown in FIG. 2), are coupled to resin, such as MBHA (FIG. 2), MBA, Tentagel™ and the like as described below, using a carbodiimide coupling agent, such as dicyclohexylcarbodiimide, diisopropylcarbodiimide, N-dimethylamninoethyl-N'-ethyl-carbodiimide and the like, and an activator, such as 1-hydroxybenzotriazole, 7-aza-1-hydroxybenzotriazole and the like, in an aprotic polar solvent such as dichloromethane, dimethylformamide and the like, at between 10° C. and 100° C. preferably at 25° C., for 2 to 24 hours, preferably 8 to 16 hours. The protecting group ("PG") of the α-amino group is removed using a strong acid such as trifluoroacetic acid or trifluoromethanesulfonic acid and the like (1–95%) or using an amine base such as piperidine, pyrrolidine, or morpholine and the like (1–95%) in an aprotic solvent such as dichloromethane, dimethylformamide and the like, at between 10° C. and 100° C., preferably at 25° C., for 2 to 24 hours, preferably 8 to 16 hours. The free amino group of the individual or mixtures of resin-bound anilines is condensed with an aldehyde in the presence of a dieneophile, such as 4-methoxystyrene, 3,5-dimethoxystyrene, N-vinylpyrrolidine, N-methyl-N-vinylpyrrolidine and the like and an acid, such as trifluoroacetic acid, toluenesulfonic acid and the like, using in a polar solvent, such as dichloromethane, dimethylformamide, dimethylacetamide, N-methylpyrrolidinone or the like, for a period of 1 to 72 hours, usually 12 to 24 hours at 20° C. to 75° C. and preferably at 25° C. to arrive at novel 4-substituted quinoline derivatives. Finally, the compounds can be cleaved from the resin by the methods common to those skilled in the art and the compounds tested for biological activity.

Figure 3:
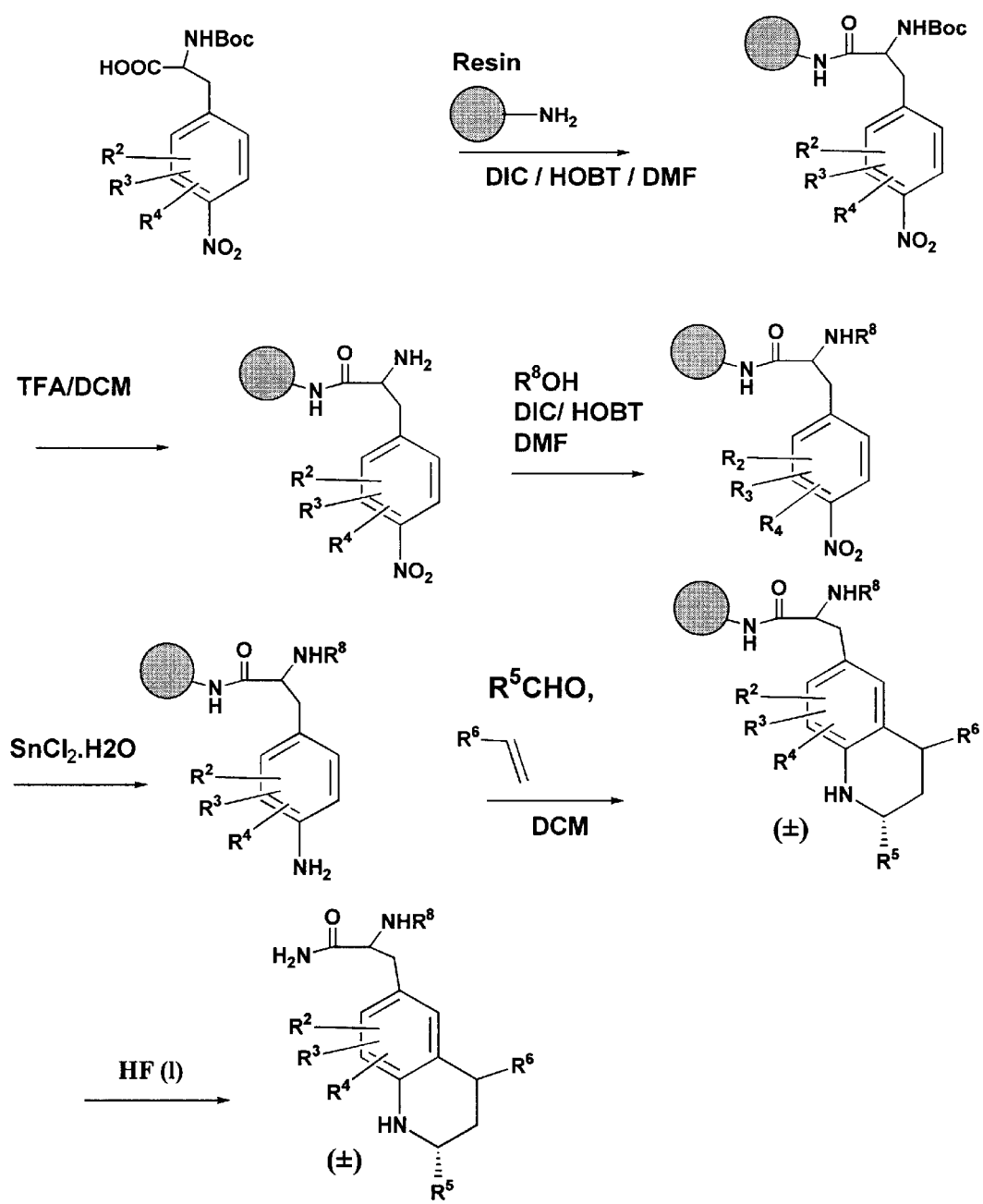
FIG. 3 provides Reaction Scheme III for the preparation of libraries and compounds containing alternatively substituted 4-substituted quinolines at the $R^{11}$ position.

More specifically, as shown by Reaction Scheme III in FIG. 3, the 4-substituted quinolines and libraries containing the same are prepared by the following more detailed steps. First, as shown in FIG. 3, N-Boc-nitrophenylalanines or, alternatively, the FMOC protected analogs are coupled to resin, such as MBHA, MBA, Tentagel™ and the like as described below, using a carbodiimide coupling agent, such as dicyclohexylcarbodiimide, diisopropyl-carbodiimide, N-dimethylaminoethyl-N'-ethyl-carbodiimide and the like, and an activator, such as 1-hydroxybenzotriazole, 7-aza-1-hydroxybenzotriazole and the like, in an aprotic polar solvent such as dichloromethane, dimethylformamide and the like, at between 10° C. and 100° C., preferably at 25° C., for 2 to 24 hours, preferably 8 to 16 hours. The BOC of the α-amino group is removed using a strong acid such as trifluoroacetic acid or trifluoromethanesulfonic acid and the like (1–95%) in an aprotic solvent such as dichloromethane, dimethylformamide and the like, at between 10° C. and 100° C., preferably at 25° C., for 2 to 24 hours, preferably 8 to 16 hours. Alternatively, the FMOC of the α amino acid is removed using an amine base such as piperidine, pyrrolidine, or morpholine and the like (1–95%) in an aprotic solvent such as dichloromethane, dimethylformamide and the like, at between 10° C. and 100° C., preferably at 25° C., for 2 to 24 hours, preferably 8 to 16 hours. The free amino group are coupled to a carboxylic acid, such as acetic acid, benzoic acid and the like (FIG. 3), using a carbodiimide coupling agent, such as dicyclohexylcarbodiimide, diisopropyl-carbodiimide, N-dimethylaminoethyl-N'-ethyl-carbodiimide and the like, and an activator, such as 1-hydroxybenzotriazole, 7-aza-1-hydroxybenzotriazole and the like, in an aprotic polar solvent such as dichloromethane, dimethylfornamide and the like, at between 10° C. and 100° C., preferably at 25° C., for 2 to 24 hours, preferably 8 to 16 hours.. The nitro group of the phenylalanine is subjected to conditions to reduce the nitro group to an amine, in the case of Reaction Scheme III tin dichloride, in an aprotic solvent such as chloroform, dimethylformamide, dimethylacetamide, N-methylpyrrolidinone for 2 to 36 hours and preferably 16 hours at 20° C. to 125° C., preferably at 25–30° C. The free amino group of the individual or mixtures of resin-bound aminophenylalanines is condensed with an aldehyde in the presence of a dieneophile, such as 4-methoxystyrene, 3,5-dimethoxystyrene, N-vinylpyrrolidine, N-methyl-N-vinylpyrrolidine and the like, and an acid such as trifluoroacetic acid or toluenesulfonic acid and the like, using in a polar solvent, such as dichloromethane, dimethylformamide, dimethylacetamide, N-methylpyrrolidinone or the like, for a period of 1 to 72 hours, usually 12 to 24 hours at 20° C. to 75° C. and preferably at 25° C. to arrive at novel 4-substituted quinoline derivatives. Finally, the compounds can be cleaved from the resin by the methods common to those skilled in the art and the compounds tested for biological activity. It should be appreciated by those of skill in the art that with certain resins, cleavage from the resin results in the functional group on the resin coming off the resin and being maintained with the cleaved compounds. For example, with an amino-resin, such as methylbenzhydrylamine resin, the amine group from the resin is cleaved off the resin and makes the 4-substituted quinoline(s) of interest an amide.

The term "functionalized resin" means any resin where functional groups have been introduced into the resin, as is common in the art. Such resins include, for example, those functionalized with amino, amide, or hydroxy groups. Such resins which can serve as solid supports are well known in the art and include, for example, 4-methylbenzhydrylamine-copoly(styrene-1% divinylbenzene) (MBHA), 4-hydroxymethylphenoxymethyl-copoly(styrene-1% divinylbenzene), 4-oxymethyl-phenyl-acetamido-copoly(styrene-1% divinylbenzene)(Wang), 4-(oxymethyl)-phenylacetamido methyl (Pam), Tentage™, from Rapp Polymere Gmbh, and trialkoxy-diphenyl-methyl ester-copoly(styrene-1% divinylbenzene) (RINK) all of which are commercially available. Preparation of the combinatorial libraries can be by the "split resin approach." The split resin approach is described by, for example, U.S. Pat. No. 5,010, 175 to Rutter, WO PCT 91/19735 to Simon, and Gallop et al., J. Med. Chem., 37:1233–1251 (1994), all of which are incorporated herein by reference.

Exemplary amino carboxylic acids which can be used in the above Reaction Schemes include 2, 3, and 4-aminobenzoic acid, aminohippuric acid, 4'-aminophenylalanine, 4'-nitrophenylalanine, anthranilic acid (2-aminobenzoic acid), 2-amino-4-chlorobenzoic acid, 2-amino-4-fluorobenzoic acid, 4-nitroanthranilic acid, 2-amino-5-bromobenzoic acid, 2-amino-5-chlorobenzoic acid, 2-amino-5-fluorobenzoic acid, 2-amino-5-iodobenzoic acid, 2-amino-5-methylbenzoic acid, 2-amino-6-methylbenzoic acid, 4,5-difluoroanthranilic acid, 3-amino-2-naphthoic acid, 4-aminobenzoic acid, 4-amino-2-chlorobenzoic acid, 4-amino-2-hydroxybenzoic acid, 4-amino-3-hydroxybenzoic acid, 4-amino-3-methoxybenzoic acid, and 4-amino-3-methylbenzoic acid. Additional amino benzoic acids or aminoaryl carboxylic acids are provided in the ensuing Examples.

Exemplary aldehydes which can be used in the above Reaction Schemes I and II are glyoxylic acid, 1-napthaldehyde, 2,3,4-trifluorobenzaldehyde, 2,3,5-trichlorobenzaldehyde, 2,3-difluorobenzaldehyde, 2,4-dichlorobenzaldehyde, 2,5-difluorobenzaldehyde, 2,5-dimethylbenzaldehyde, 2,6-difluorobenzaldehyde, 2-bromobenzaldehyde, 2-chloro-5-nitrobenzaldehyde, 2-fluorobenzaldehyde, 3,4-(methylenedioxy)-6-nitrobenzaldehyde (6-nitropiperonal), 3,4-difluorobenzaldehyde, 3,5-bis(trifluoromethyl)benzaldehyde, 3,5-dichlorobenzaldehyde, 3-cyanobenzaldehyde, 3-fluorobenzaldehyde, 3-formylchromone, 3-nitro-4-chlorobenzaldehyde, 3-phenoxybenzaldehyde, 4-cyanobenzaldehyde, 4-pyridinecarboxaldehyde, 3-methoxy-2-nitrobenzaldehyde, 3-hydroxy-4-nitrobenzaldehyde. Additional aldehydes include the following, 2-nitrobenzaldehyde, 2,4-dinitrobenzaldehyde, 4-methyl-2-nitrobenzaldehyde, 4,5-methylenedioxy-2-nitrobenzaldehyde, 5-ethyl-2-nitrobenzaldehyde, 4,5-dimethoxy-2-nitrobenzaldehyde, 5-chloro-2-nitrobenzaldehyde, 3-fluoro-2-nitrobenzaldehyde, 3-trifluoro-2-nitrobenzaldehyde, 4(dimethylamino)-2-nitrobenzaldehyde, 3-methoxy-2-nitrobenzaldehyde, 5-hydroxy-2-nitrobenzaldehyde, 2,6-dinitrobenzaldehyde and the like.

Exemplary carboxylic acid which can be used in the above Reaction Schemes include, but are not limited to, acetic acid, butyric acid, cyclobutanecarboxylic acid, cycloheptanecarboxylic acid, cyclohexanebutyric acid, cyclohexanecarboxylic acid, cyclohexanepropionic acid, cyclohexylacetic acid, cyclopentanecarboxylic acid, cyclopentylacetic acid, hydrocinnamic acid, isobutyric acid, isovaleric acid, octanoic acid, propionic acid, tert-butylacetic acid, trimethylacetic acid, 1-adamantaneacetic acid, 4-methyl-1-cyclohexanecarboxylic acid, 4-methylcyclohexaneacetic acid, 4-methylvaleric acid, 2-ethyl-2-hexenoic acid, 2-ethylbutyric acid, 2-ethylhexanoic acid, 2-methylbutyric acid, 2-methylcyclopropanecarboxylic acid, 2-norbomaneacetic acid, 2-phenylbutyric acid, 2-propylpentanoic acid, 3,3,3-triphenylpropionic acid, 3,3-diphenylpropionic acid, 4-tert-butyl-cyclohexanecarboxylic acid, 3,5,5-trimethylhexanoic acid, 5-phenylvaleric acid, 3-(2-methoxyphenyl)propionic acid, 3-(3,4,5-trimethoxyphenyl)propioniic acid, 3-(3,4-dimethoxyphenyl)-propionic acid, heptanoic acid, 3-cyclopentylpropionic acid, formic acid, lauric acid, 3-methylvaleric acid, 3-phenylbutyric acid, α-cyclohexylphenylacetic acid, αmethylcinnamic acid, crotonic acid, ethoxyacetic acid, 4-chlorocinnamic acid, 4ethoxyphenylacetic acid, m-tolylacetic acid, methoxyacetic acid, p-tolylacetic acid, phenoxyacetic acid, phenylacetic acid, tiglic acid, trans-3-hexenoic acid, trans-cinnamic acid, trans-styrylacetic acid, triphenylacetic acid, 4-fluorophenylacetic acid, vinylacetic acid, (2,5-dimethoxyphenyl)acetic acid, (2-naphthoxy)acetic acid, (3,4-dimethoxyphenyl)acetic acid, (α-α-α-trifluoro-m-tolyl)acetic acid, (methylthio)acetic acid, 1-(4-chlorophenyl)-1-cyclopentanecarboxylic acid, 1-naphthylacetic acid, 1-phenyl-1-cyclopropanecarboxylic acid, 4-isobutyl-α-methylphenylacetic acid, 4-methoxyphenylacetic acid, 2,4-hexadienoic acid, 2-(trifluoromethyl)-cinnamic acid, 2-chloro-4-fluorophenylacetic acid, 2-naphthylacetic acid, 3,4,5-trimethoxycinnamic acid, 3,4-dichlorophenylacetic acid, 3,4dimethylbenzoic acid, 3,4,5-trimethoxyphenylacetic acid, 3-benzoylpropionic acid, 3-bromophenylacetic acid, 3-fluorophenylacetic acid, 3-methoxyphenylacetic acid, 3-thiopheneacetic acid, 4-biphenylacetic acid, 4-bromophenylacetic acid, α,α,α-trifluoro-m-toluic acid, α,α,α-trifluoro-o-toluic acid, benzoic acid, niflumic acid, o-anisic acid, o-toluic acid, piperonylic acid, 1-napthoic acid, 2,3-dichlorobenzoic acid, 2,3-dimethoxybenzoic acid, 2,4-dichlorobenzoic acid, 2,4-difluorobenzoic acid, 2,4-dimethoxybenzoic acid, 2,4-dimethylbenzoic acid, 2,5-dichlorobenzoic acid, 2,5-dimethylbenzoic acid, 2,6-dichlorobenzoic acid, 2,6-difluorobenzoic acid, 2,6dimethoxybenzoic acid, 2-bromobenzoic acid, 2-chloro-4,5-difluorobenzoic acid, 2-chlorobenzoic acid, 2-ethoxybenzoic acid, 2-fluorobenzoic acid, 2-napthoic acid, 3,4,5-triethoxybenzoic acid, 3,4,5-trimethoxybenzoic acid, 3,4-dichlorobenzoic acid, 3,4-difluorobenzoic acid, 3,4-dimethoxybenzoic acid, 3,5-bis(trifluoromethyl)-benzoic acid, 5-bromo-2-chlorobenzoic acid, 3,5-dimethyl-p-anisic acid, 3-bromobenzoic acid, 3-chlorobenzoic acid, 3-cyanobenzoic acid, 3-dimethylaminobenzoic acid, 3-fluoro-4-methylbenzoic acid, 3-fluorobenzoic acid, 3-iodo-4-methylbenzoic acid, 3-phenoxybenzoic acid, 4-chloro-o-anisic acid, α,α,α-trifluoro-p-toluic acid, 4-cyanobenzoic acid, 4-dimethylaminobenzoic acid, 4-ethoxybenzoic acid, isonicotinic acid, 4-ethylbenzoic acid, m-anisic acid, m-toluic acid, nicotinic acid, p-anisic acid, p-toluic acid, picolinic acid, pyrrole-2-carboxylic acid, 4-fluorobenzoic acid, 4-isopropoxybenzoic acid, tetrahydro-2-fiuroic acid, tetrahydro-3-furoic acid, trans-3-(3-pyridyl)acrylic acid, xanthene-9-carboxylic acid, (4-pyridylthio)acetic acid, (phenylthio)acetic acid, 4-iodobenzoic acid, 4-isopropylbenzoic acid, 2-furoic acid, 2-pyrazinecarboxylic acid, 2-thiopheneacetic acid, 2-thiophenecarboxylic acid, 5-bromonicotinic acid, 3,5-dichlorobenzoic acid, 6-chloronicotinic acid, 3,5-dimethoxybenzoic acid, 3,5-dimethylbenzoic acid, chromone-2-carboxylic acid, 1-isoquinolinecarboxylic acid, 3-methyl-2-thiophenecarboxaldehyde, 4-ethylbiphenylcarboxylic acid, 4-(diethylamino)benzoic acid, 4-benzoylbenzoic acid, 4-biphenylcarboxylic acid, 4-bromobenzoic acid, 4-butylbenzoic acid, 4-chlorobenzoic acid, additionally acid chlorides include the following; acetyl chloride, phenoxyacetyl chloride, 4-chlorophenoxyacetyl chloride benzyloxyacetyl chloride and acetoxyacetyl chloride.

The 4-substituted quinolines prepared by the above Reaction Schemes, once cleaved from the resin, result in compounds of Formula II:

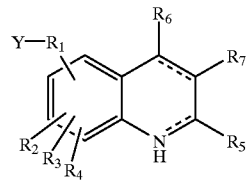

Formula II

These 4-substituted quinoline compounds of Formula II can be converted, generally before cleavage from tile resin, to alternatively substituted compounds having an alkyl or acyl, or other functionality as defined by $R^9$ above and provided by Formula I:

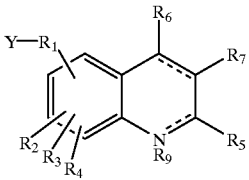

Formula I

Figure 4:
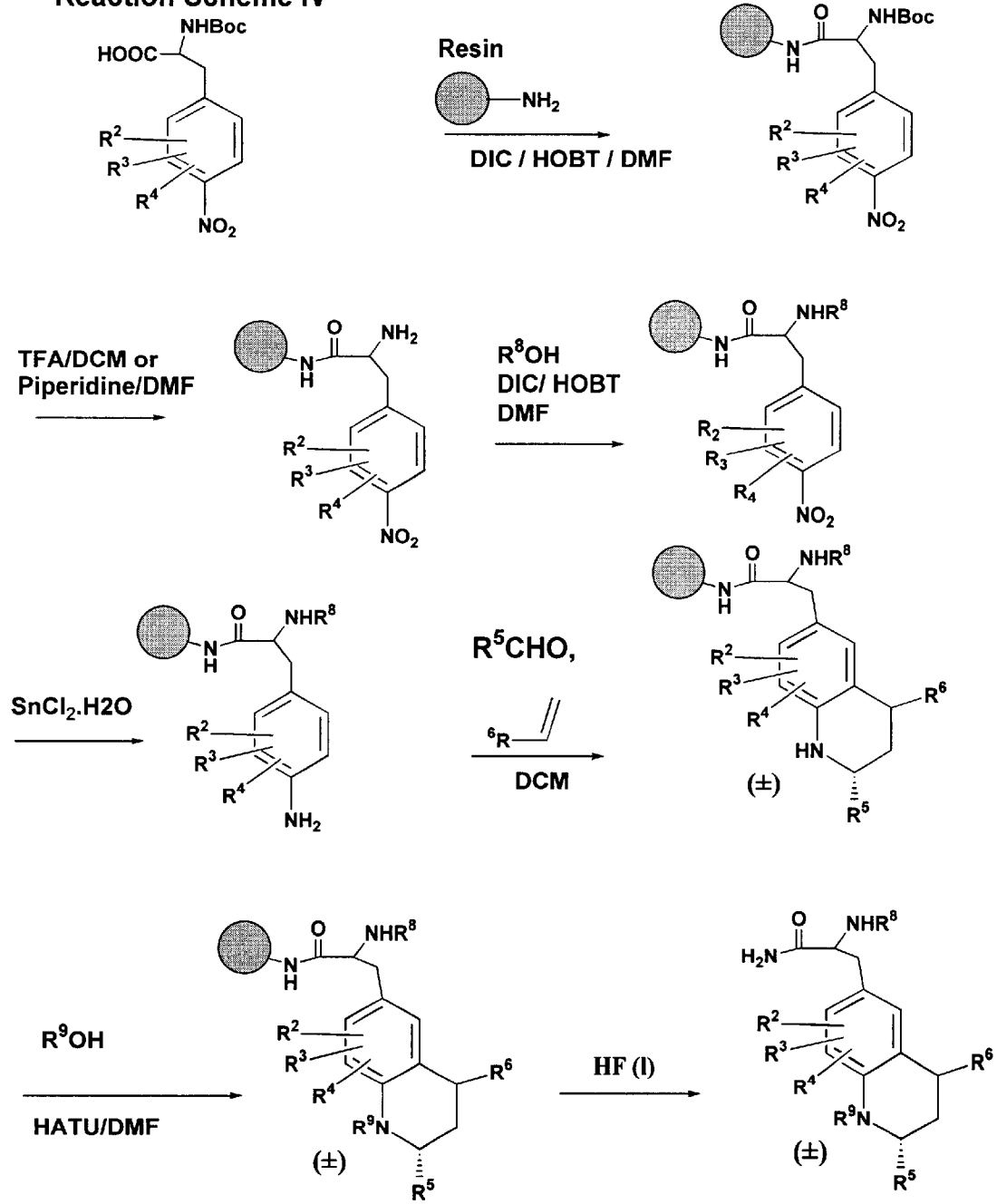
FIG. 4 provides Reaction Scheme IV for the preparation of libraries and compounds containing alternatively substituted 4-substituted quinolines at the $R^9$ position.

The 4-substituted quinolines of Formula II, before cleavage from the resin, can be substituted at positions $R^9$ following Reaction Scheme IV provided in FIG. 4. Briefly, as shown in Reaction Scheme IV, the 4-substituted quinoline prepared by the above Reaction Schemes I, II or III is condensed with a carboxylic acid, carboxylic acid anhydride, acid halide, alkyl halide or isocyanate in an aprotic solvent, such as dimethylformamide, dichloromethane, 1-methyl-2-pyrrolidinone, N-N,-dimethylacetamide, tetrahydrofuran, dioxane and the like, in the presence of an acid acceptor, if desired, to furnish the substituted 4-substituted quinoline.

For example, preparation of the library containing alternatively substituted 4-substituted quinolines other than $R^9$ equal to a hydrogen atom involves, instead of cleaving from the resin, free NH of the newly formed 4-substituted quinoline compound being reacted with a carboxylic acid activated with N-[(dimethylamino)-1H-1,2,3-triazolo[4,5-b] pyridin-1-ylmethylene]-N-methylmethanaminium hexafluorophosphate N-oxide (HATU, Perspective Biosystems, Farmingham, Mass.), dissolved in dimethylformamide, N-N,-dimeftiylacetaride, 1-methyl-2-pyrrolidinone and the like. The reaction is allowed to proceed for 1 to 24 hours at 20° C. to 80° C., preferably at 25° C. for 3 to 5 hours to yield various carboxamide derivatives. Finally, the compounds are cleaved from the resin as described above and tested for biological activity.

Exemplary carboxylic acid, carboxylic acid anhydride, acid halide, alkyl halide or isocyanate which can be used include nalidixic acid, 2-phenyl-4-quinolinecarboxylic acid, 2-pyraznecarboxylic acid, niflumic acid, 4-nitrophenylacetic acid, 4-(-nitrophenyl)butyric acid, (3,4-dimethoxyphenyl) acetic acid, 3,4-(methylenedioxy)phenylacetic acid, 4-nitrocinnamic acid, 3,4,-(methylenedioxy)cinnamic acid, 3,4,5-timethoxycinnamic acid, benzoic acid, 2-chlorobenzoic acid, 2-nitrobenzoic acid, 2-(p-toluoyl) benzoic acid, 2,4-dinitrophenylacetic acid, 3-(3,4,5-trimethoxyphenyl)-proprionic acid, 4-biphenylacetic acid, 1-napthylacetic acid, (2-napthoxy)acetic acid, trans-cinnamic acid, picolinic acid, 3-amino-4-hydroxybenzoic acid, (4-pyridylthio)acetic acid, 2,4-dichlorobenzoic acid, 3,4-dichlorobenzoic acid, 4-biphenylcarboxylic acid, thiophenoxyacetic acid, 1-benzoylpropionic acid, phenylacetic acid, hydrocinnamic acid, 3,3-diphenylpropionic acid, 3,3,3-triphenylpropionic acid, 4-phenylbutyric acid, phenoxyacetic acid, (+/–)-2-phenoxypropionic acid, 2,4-dimethoxybenzoic acid, 3,4-dimethoxybenzoic acid, 3,4-dihydroxybenzoic acid, 2,4-dihydroxybenzoic acid, 3,4,5-trimethoxybenzoic acid, 3,4,5-triethoxybenzoic acid, 3,4,5-trihydroxybenzoyl, 2-benzoylbenzoic acid, 1-napthoic acid, xanthene-9-carboxylic acid, 4-chloro-2-nitrobenzoic acid, 2-chloro-4-nitrobenzoic acid, 4-chloro-3-nitrobenzoic acid, 2-chloro-5-nitrobenzoic acid, 4-dimethylaminobenzoic acid, 4-(diethylamino)benzoic acid, 4-nitrobenzoic acid, 3-dimethylamninobenzoic acid, p-toluic acid, p-anisic acid, trimethylacetic acid, tert-butylacetic acid, (–)-menthoxyacetic acid, cyclohexanecarboxylic acid, cyclohexylacetic acid, dicyclohexylacetic acid, cyclohexanebutyric acid, cycloheptanecarboxylic acid, abietic acid, acetic acid, octanoic acid, (methylthio)acetic acid, 3-nitropropionic acid, 4-amino-3 hydroxybenzoic acid, 2-methyl-4-nitro-1-imidizole propionic acid, 2-furoic acid, (s)(–)-2-pyrrolidone-5-carboxylic acid, (2-pyrimidylthio) acetic acid, 4-methoxy-2-quinolinecarboxylic acid, 1-adaimantanecarboxylic acid, piperonylic acid, 5-methyl-3-phenylisoxazole-4-carboxylic acid, rhodanine-3-acetic acid, 2-norbornaneacetic acid, nicotinnic acid, 9-oxo-9H-thioxanthene-3-carboxylic acid 10,10 dioxide, 2-thiophenecarboxylic acid, 5-nitro-2-fluroic acid, indole-3-acetic acid, isonicotinic acid, lithocholic acid, cholic acid, deoxycholic acid, hyodeoxycholic acid, Boc-L-Ala, Boc-L-Cys(Mob), Boc-L-Asp(Bzl), Boc-L-Glu(Bzl), Boc-L-Phe, Boc-Gly, Boc-L-His(Tos), Boc-L-Ile, Boc-L-Lys(Clz), Boc-L-Leu, Boc-Met(O), Boc-L-Asn, Boc-L-Pro, Boc-L-Gln, Boc-L-Arg(Tos), Boc-L-Ser(Bzl), Boc-L-Thr(Bzl), Boc-L-Val, Boc-L-Trp, Boc-L-Tyr(Brz), Boc-D-Ala, Boc-D-Cys (Mob), Boc-D-Asp(Bzl), Boc-D-Glu(Bzl), Boc-D-Phe, Boc-D-His(Dnp), Boc-D-Ile, Boc-D-Lys(Clz), Boc-D-Leu, Boc-D-Met(O), Boc-D-Asn, Boc-D-Pro, Boc-D-Gln, Boc-D-Arg(Tos), Boc-DSer(Bzl), Boc-D-Thr(Bzl), Boc-D-Val, Boc-D-Trp(CHO), Boc-D-Tyr(Brz), Boc-L-Met, 2-aminobutyric acid, 4-aminobutyric acid, 2-aminoisobutyric acid, L-norleucine, D-norleucine, 6-aminocaproic acid, 7-arninoheptanoic acid, thioproline, L-Norvaline, D-Norvaline, α-ornithine, methionyl sulfonyl, L-naphthyalanine, D-naphthyalanine, L-phenylglycine, D-phenylglycine, β-alanine, L-cyclohexylalanine, D-cyclohexylalanine, hydroxyproline, nitrophenylalanine, dehydroproline, 1,3-propane sultone, 1-propanesulfonyl chloride, 1-octanesulfonyl chloride, perfluoro-1-octanesulfonly fluoride, (+)-10-camphorsulfonyl chloride, (–)-10-camphorsulfonyl chloride, benzenesulfonly chloride, 2-nitrobenzenesulfonyl chloride, p-toluenesulfonyl chloride, 4-nitrobenzenesulfonyl chloride, n-acetylsulfanilyl chloride, 2,5-dichlorobenzenesulfonyl chloride, 2,4-dinitrobenzenesulfonyl chloride, 2-mesitylenesulfonyl chloride, 2-napthalenesulfonyl chloride, phenylisocyanate, methylisocyanate and t-butyl isocyanate. Those abbreviations used above for amino acids and their protecting groups are ones commonly used in the field, each of which are identified, for example, in Stewart and Young, supra.

Figure 5:
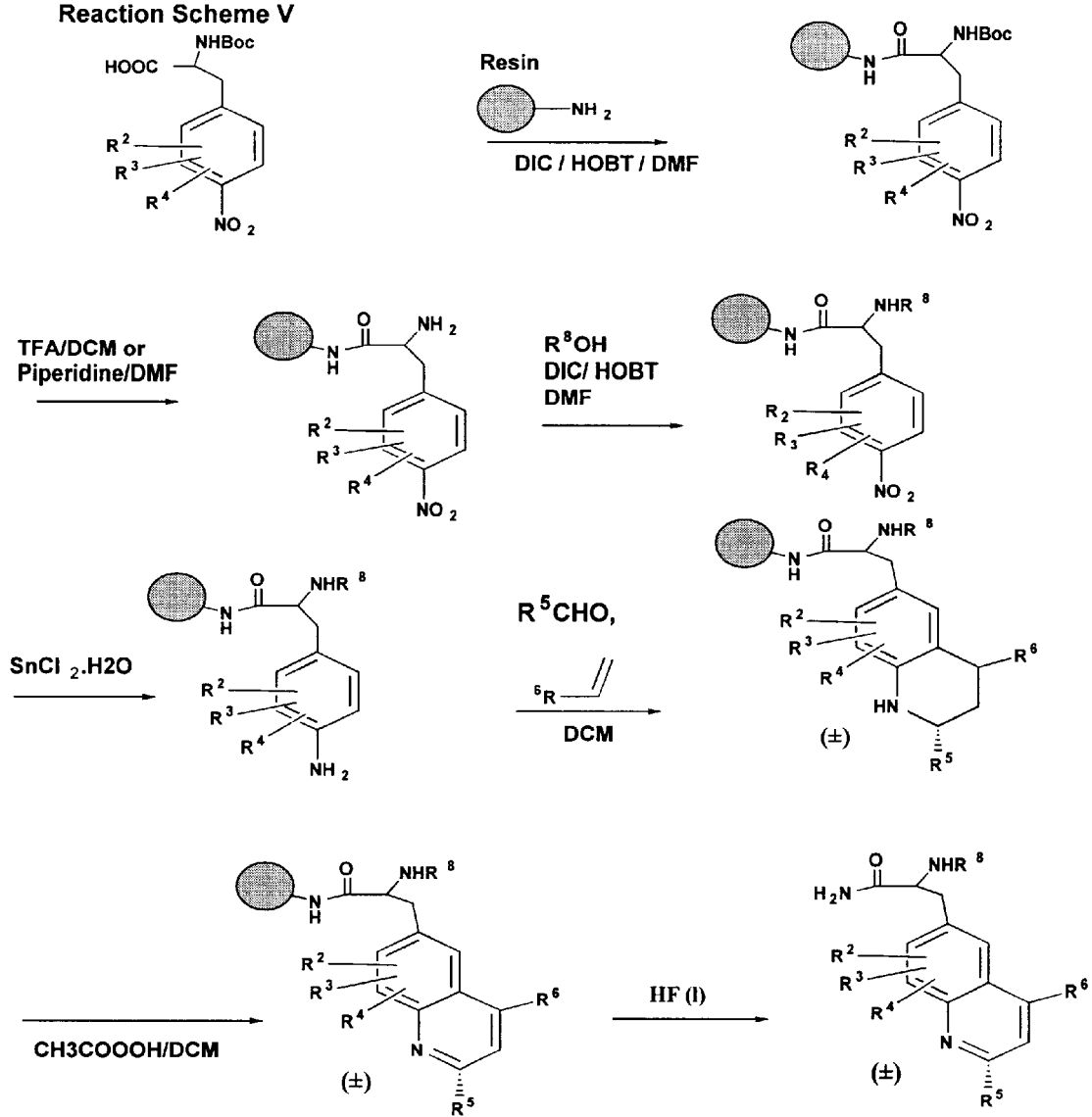
FIG. 5 provides Reaction Scheme V for the preparation of oxidized libraries and compounds of the present invention.

The 4-substituted quinolines of Formula II which are in the 1,2,3,4-tetrahydro form, before or after cleavage from the resin, can be oxidized to the quinoline provided $R^9$ is a hydrogen atom following Reaction Scheme V provided in FIG. 5. Briefly, as shown in Reaction Scheme V, the 4-substituted quinoline prepared by the above Reaction Schemes I, II or III is reacted with an oxidant, such as peractetic acid, meta-chloroperbenzoic acid, iodine in an aprotic solvent, such as dimethylformamide, dichloromethane, 1-methyl-2-pyrrolidinone, N-N,-dimethylacetamide, tetrahydrofuran, dioxane and the like, to furnish the substituted quinoline.

Pharmaceutical compositions containing the new 4-substituted quinoline derivatives are also included within the scope of the present invention, as are methods of using the compounds and compositions. The new 4-substituted quinoline compounds of the present invention can be used for a variety of purposes and indications. For instance, related tetrahydroquinolines have been reported to N-methyl-D-aspartate (NMDA) receptor site antagonists and, therefore, useful in reducing ischemic brain damage as described, for example, in Leeson et al., *J. Med. (Chem.* 35:1954 (1992), which is incorporated herein by reference. Moreover, to evaluate whether the subject 4-substituted quinolines have antimicrobial activity, and, therefore, can be used to treat infections, the ability of the compounds to inhibit bacterial growth can be determined by methods well known in the art. An exemplary in vitro antimicrobial activity assay is described in Blondelle and Houghten, Biochemistry 30:4671–4678 (1991), which is incorporated herein by reference. In brief, *Staphylococcus aureus* ATCC 29213 (Rockville, Md.,) is grown overnight at 37° C. in Mueller-Hinton broth, then reinoculated and incubated at 37° C. to reach the exponential phase of bacterial growth (i.e., a final bacterial suspension containing $10^5$ to $5 \times 10^5$ colony-forming units/ml). The concentration of cells is established by plating 100 µl of the culture solution using serial dilutions (e.g., $10^{-2}$, $10^{-3}$ and $10^{-4}$) onto solid agar plates. In 96-well tissue culture plates 4-substituted quinolines, individual or in mixtures, are added to the bacterial suspension at concentrations derived from serial two-fold dilutions ranging from 1500 to 2.9 µg/ml. The plates are incubated overnight at 37° C. and the growth determined at each concentration by $OD_{620}$ nm. The $IC_{50}$ (the concentration necessary to inhibit 50% of the growth of the bacteria) can then be calculated.

Additional assays can be used to test the biological activity of the instant 4-substituted quinolines. Such as a competitive enzyme-linked immunoabsorbent assay and radio-receptor assays, both as described in greater detail below. The latter test, the radio-receptor assay, can be selective for either the µ, δ or κ opiate receptors and is therefore an indication of 4-substituted quinolines analgesic properties.

Competitive Enzyme-Linked Immunosorbent Assay (ELISA): The competitive ELISA method which can be used here is a modification of the direct ELISA technique described previously in Appel et al., J. Immunol. 144:976–983 (1990), which is incorporated herein by reference. It differs only in the MAb addition step. Briefly, multi-well microplates are coated with the antigenic peptide (Ac-GASPYPNLSNQQT-$NH_2$) at a concentration of 100 pmol/50 µl. After blocking, 25 µl of a 1.0 mg/ml solution of each 4-substituted quinoline mixture of a synthetic combinatorial library (or individual 4-substituted quinoline) is added, followed by MAb 125-10 F3 (Appel et al., supra) (25 µl per well). The MAb is added at a fixed dilution in which the 4-substituted quinoline in solution effectively competes for MAb binding with the antigenic peptide adsorbed to the plate. The remaining steps are the same as for direct ELISA. The concentration of 4-substituted quinoline necessary to inhibit 50% of the MAb binding to the control peptide on the plate ($IC_{50}$) is determined by serial dilutions of the 4-substituted quinoline.

Radio-Receptor Assay: Particulate membranes can be prepared using a modification of the method described in Pasternak et al., Mol. Pharmacol. 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall® RC5C SA-600: Du Pont, Wilmington, Del.) (16,000 rpm) for 10 mins. The pellets are resuspended in fresh Tris-HCl buffer and incubated at 37° C. for 40 mins. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in M. M. Bradford, M. M., Anal. Biochem. 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 µg/ml of 4-substituted quinoline, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cprn. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the 4-substituted quinolines, individually or in mixtures. $IC_{50}$ values (the concentration necessary to inhibit 50% of $^3$H-DAMGO binding) are then calculated. As opposed to this µ receptor selective assay, assays selective for δ receptors can be carried out using [$^3$H]-Naltrindole (3 nM, specific activity 32 Ci/mmol as radioligand or, alternatively, assays selective for κ receptors can be carried out using [$^3$H]-U69,593 (3 nM, specific activity 62 Ci/mmol) as radioligand.

As pharmaceutical compositions for treating infections, pain, or any other indication the 4-substituted quinoline compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active 4-substituted quinoline. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

EXAMPLE 1

Combinatorial Library of 4-(4-Methoxyphenyl) Tetrahydroquinoline Derivatives This Example provides a representative solid-phase combinatorial synthesis of a library which contains approximately 2380 derivatives of 4-aryltetrahydroquinolines (THQs).

Following the above Reaction Scheme I, preparation of a library containing the THQs involves the following steps. Briefly, first, 17 diverse aminobenzoic acids, varying at position of Y—$R^1$, $R^2$, $R^3$ or $R^4$ without use of amino-protecting groups, were coupled to MBHA resin employing the tea-bag method of Houghten et. al, as described, for example in U.S. Pat. No. 4,631,211 to Houghten and Houghten et al., *Proc. Natl. Acad. Sci.*, 82:5131–5135 (1985), both of which are incorporated herein by reference. After coupling and thorough washing the 17 tea-bags, each containing one resin-bound aminobenzoic acid, were opened and the resin beads combined and thoroughly mixed in a large tea-bag as a suspension in dichloromethane (DCM). The resin mixture was dried under vacuum, then divided into equivalent portions and resealed in 70 labeled tea-bags, each tea-bag now containing a mixture of the 17 aminobenzoic acids. This was followed by reaction with 70 aldehydes, each differing by their $R^5$ substituent, and 4-methoxystyrene in the presence of trifluoroacetic acid. After washing with a series of solvents, the resins were dried under vacuum and the mixtures individually cleaved from the MBHA resin using a hydrogen fluoride (HF) procedure. The individual mixtures varying at Y—$R^1$, $R^2$, $R^3$ or $R^4$ and constant at $R^5$, each a mixture containing 34 individual compounds, including enantiomers, can then be tested for biological activity using any one of a variety of screening assays, such as those described above or others well known in the art.

The individual aminobenzoic acids which were used to prepare the library of 2380 THQs include the following: anthranilic acid, 2-amino-4-chlorobenzoic acid, 2-amino-4-fluorobenzoic acid, 2-amino-5-bromobenzoic acid, 2-amino-5-chlorobenzoic acid, 2-amino-5-fluorobenzoic acid, 2-amino-5-iodobenzoic acid, 2-amino-5-methylbenzoic acid, 4,5-difluoroantranilic acid, 3-amino-2-naphthoic acid, 4-aminobenzoic acid, 4-amino-2-chlorobenzoic acid, 4-amino-2-hydroxybenzoic acid, 4-amino-3-hydroxybenzoic acid, 4-amino-3-methoxybenzoic acid, 4-amino-3-methylbenzoic acid, and 4-aminohuppuric acid.

Individual aldehydes employed were as follows: 1-methyl-2-pyrrolecarboxaldehyde, 1-napthaldehyde, 2,2-dimethyl-4-pentenal, 2,3,4-trifluorobenzaldehyde, 2,3,5-trichlorobenzaldehyde, 2,3-difluorobenzaldehyde, 2,3-dimethylvaleraldehyde, 2,4-dichlorobenzaldehyde, 2,5-difluorobenzaldehyde, 2,5-dimethylbenzaldehyde, 2,6-difluorobenzaldehyde, 2-bromobenzaldehyde, 2-chloro-5-nitrobenzaldehyde, 2-chloro-6-fluorobenzaldebyde, 2-cyanobenzaldebyde, 2-ethylbutyraldehyde, 2-fluorobenzaldehyde, 2-formylphenoxyacetic acid, 2-methoxy-1-naphthaldehyde, 2-methylbutyraldehyde, 2-methylundecanal, 2-methylvaleraldehyde, 2-nitro-5-chlorobenzaldehyde, 2-nitrobenzaldehyde, 2-pyridinecarboxaldehyde, 3,4-(methylenedioxy)-6-nitrobenzaldehyde, 3,4-difluorobenzaldebyde, 3,5-bis(trifluoromethyl)benzaldehyde, 3,5-dichlorobenzaldehyde, 3-(3,4-dichlorophenoxy)benzaldehyde, 3-bromo-4-fluorobenzaldehyde, 3-bromobenzaldehyde, 3-carboxybenzaldehyde, 3-cyanobenzaldehyde, 3-fluorobenzaldehyde, 3-formylchromone, 3-furaldehyde, 3-hydroxy-4-nitrobenzaldehyde, 3-hydroxybenzaldehyde, 3-methoxy-2-nitrobenzaldehyde, 3-nitro-4-cblorobenzaldehyde, 3-nitrobenzaldehyde, 3-phenoxybenzaldehyde, 3-phenylbutraldehyde, 3-pyridinecarboxaldehyde, 4-bromo-2-thiophenecarboxaldehyde, 4-bromobenzaldehyde, 4-carboxybenzaldehyde, 4-chloro-3-nitrobenzaldehyde, 4-cyanobenzaldehyde, 4-fluorobenzaldehyde, 4-nitrobenzaldehyde, 4-pyridinecarboxaldehyde, 4-quinolinecarboxaldehyde, 5-bromosalicylaldehyde, 5-nitro-2-furaldehyde, 5-norbornene-2-carboxaldehyde, 6-methyl-2-pyridinecarboxaldehyde, 9-ethyl-3-carbazolecarboxaldehyde, benzaldehyde, chloroacetaldehyde, cyclohexanecarboxaldehyde, D,L-glyceraldehyde, glyoxylic acid monohydrate, parafonnldehyde, pyruvic aldehyde, salicylaldehyde, tribromoacetaldehyde, trifluoro-p-tolualdehyde, and trimethylacetaldehyde.

1. Coupling of Aminobenzoic Acids to MBHA Resin

Seventeen polypropylene mesh packets (tea-bags, ~22" square, 65μ; McMaster Carr, Chicago, Ill.) of (5 g, 0.89 meq/g) MBHA resin were prepared, washed with DCM (2×, ~5 ml each), neutralized with 5% diisopropylethylamine/dicbloromethane (DIEA/DCM) (3×, ~5 ml each), and washed with DCM (2×, ~5 ml each). Each resin packet was individually coupled overnight (~16 hrs) by adding 5×aminobenzoic acid (0.5 M)in 1:1 DMF/DCM solvent system followed by 5×diisopropylcarbodiimide (DIC) in DCM (0.5 M) and hydroxybenzotriazole (HOBt) (5×). Following coupling completion, resin packets were washed with DCM (2×), DMF (2×), and DCM (1×) and MeOH (1×).

After drying under vacuum 4–12 hrs, each individual packet was then opened and a proportional amount of resin transferred to a large Tea-bag (~5" square) which was sealed and shaken in DCM for 1 hour. After a MeOH wash the mixed resin was dried under vacuum and then 30 mg portions (calc. 25 micromole) distributed into labeled Tea-bags (~1.5" square) for use in subsequent chemistry.

TABLE 1

Experimental Data for Aminobenzamide Controls

| No. | Amide formed upon cleavage | Yield (mg) | Yield (%) | Calc. MW | Obs.* MW (M+1) | $^1$H NMR (d, d6-DMSO) |
|---|---|---|---|---|---|---|
| 1 | Anthranilamide (2-amino-benzamide) | 8.5 | 83 | 136.1 | 137.1 | 7.90(b, 1H), 7.62(d, 1H), 7.20–7.42(b and dd, 2H), 6.88(d, 1H), 6.75(dd, 1H), 5.30 (vb) |
| 2 | 2-amino-4-chlorobenzamide | 9.8 | 77 | 170.6 | 171.1 | 7.80(b, 1H), 7.52(d, 1H), 7.15(b, 1H), 6.71(d, 1H), 6.47 (dd, 1H), 3.50(vb, 2H) |
| 3 | 2-amino-4-fluorobenzamide | 6.2 | 54 | 154.1 | 155.1 | 7.70(b, 1H), 7.47(t, 1H), 7.08(b, 1H), 6.42(dd, 1H), 6.26 (ddd, 1H), 4.65(vb, 2H) |
| 4 | 2-amino-5-bromobenzamide | 11.2 | 69 | 215 | 215.1 216.9 | 7.83(b, 1H), 7.66(d, 1H), 7.29–7.13(dd and b, 2H), 6.80–6.52 (b and d, 3H) |
| 5 | 2-amino-5-chlorobenzamide | 9.1 | 71 | 170.6 | 171.1 | 7.83(b, 1H), 6.71(d, 1H) 7.30–7.09(b and dd, 2H), 7.77–7.60(b and d, 3H) |
| 6 | 2-amino-5-fluorobenzamide | 8.8 | 76 | 154.1 | 155 | 7.80(b, 1H), 7.43 (dd, 1H), 7.25(b, 1H), 7.06(ddd, 1H), 6.73(dd, 1H), 4.97 (vb) |
| 7 | 2-amino-5-iodobenzamide | 14.1 | 72 | 262 | 262.9 | 7.93–7.78(b and d, 2H), 7.38(dd, 1H), 7.25(b, 1H), 6.54(d, 1H), 3.45(vb, 2H) |
| 8 | 2-amino-5-methylbenzamide | 11.1 | 99 | 150.2 | 151.1 | 7.82(b, 1H), 7.41(s, 1H), 7.19(b, 1H), 7.05(dd, 1H), 6.70 (dd, 1H), 3.55(vb), 2.17(s,3H) |
| 9 | 4,5-difluoro-anthranilamide | 4.4 | 34 | 172.1 | 173.1 | 7.78(b, 1H), 7.63 (dd, 1H), 7.22(b, 1H), 6.62(dd, 1H), 3.70(vb) |
| 10 | 3-amino-2-naphthamide | 9.4 | 67 | 186.2 | 187.1 | 8.17(b and s, 2H), 7.95(2, 1H), 7.76(d, 1H), 7.60(d, 1H), 7.58(b, 1H)738(dd, 1H), 7.10(dd, 1H), 7.08(s, 1H) |
| 11 | 4-aminobenzamide | 9.5 | 93 | 136.1 | 137.1 | 7.64(d, 2H), 6.65(d, 1H), 5.10(vb) |
| 12 | 4-amino-2-chlorobenzamide | 8.8 | 69 | 170.6 | 171.6 | 7.57(b,1H), 7.22(d, 2H), 6.63(d, 1H), 6.53(d, 1H), 4.10 (vb) |
| 13 | 4-amino-2-hydroxybenzamide | 10.4 | 91 | 152.1 | 153.3 | 7.60(b,1H), 7.28(s, 1H), 7.21(d, 1H), 6.94(b, 1H), 6.71(d, 1H), 3.50(vb) |
| 14 | 4-amino-3-hydroxybenzamide | 10 | 88 | 152.1 | 153.4 | 7.90(b,1H), 7.50(d, 1H), 6.11(d, 1H), 6.05(s, 1H), 5.35 (vb) |
| 15 | 4-amino-3-methoxybenzamide | 11 | 88 | 166.2 | 167.2 | 7.71(b, 1H), 7.41(s, 1H), 7.36(d, 1H), 7.11(b, 1H), 6.80(d, 1H), 4.70(vb), 3.72 (s, 3H) |
| 16 | 4-amino-3- | 9.2 | 82 | 150.2 | 151.3 | 7.75–7.48(b and s |

TABLE 1-continued

Experimental Data for Aminobenzamide Controls

| No. | Amide formed upon cleavage | Yield (mg) | Yield (%) | Calc. MW | Obs.* MW (M+1) | $^1$H NMR (d, d6-DMSO) |
|---|---|---|---|---|---|---|
| | methylbenzamide | | | | | and d, 3H), 6.94(b, 1H), 6.75(d, 1H), 4.60(vb), 2.13(s, 3H) |
| 17 | 4-aminohippuric amide (N-(4-amino) benzoylamino-acetamide) | 14.1 | 97 | 193.2 | 194.1 | 8.76(b, 0.5H),8.57 (b, 0.5H), 8.44(b, 0.5H), 8.23(b, 0.5H), 7.83(dd, 2H), 7.62 (m, 4H), 7.33(bd, 1H), 7.00(bd, 1H), 6.62(d, 2H) |

*"Obs. MW" stands for Observed Molecular Weight

2. Reaction of the Mixture of Resin-Bound Aminobenzoic Acids with Aldehydes and 4-Methoxystyrene Tea-bags containing mixtures of 17 aminobenzamide-resins (30 mg, calc. 25 mmole) were added to each solution of 70 aldehydes (1 M) in DMF (10 mL) and cooled in the freezer (−10° C.) for 15–30 minutes. After cooling, 2.42 mL of 4-methoxystyrene (2M final concentration) was added and the solution cooled in the freezer again for 15–30 minutes. Then 0.77 mL of trifluoroacetic acid (1M) was added and the cyclization reaction shaken for 45–50 hours at room temperature. Following completion of the 4-(4-Methoxyphenyl)tetrahydroquinoline formation, the resin packets were washed with DCM (2×), DMF (2×), and DCM (1×), MeOH (1×) and dried under vacuum.

The 4-(4-methoxyphenyl)tetrahydroquinoline controls and mixtures were cleaved off the resin by treatment with HF (liquid (l)) at −15° C. for 2 hrs in the presence of anisole scavenger followed by warning to room temperature while removing HF (gaseous (g)) with a nitrogen stream.

EXAMPLE 2

Combinatorial Library of 4-(3,4-Dimethoxyphenyl) Tetrahydroquinoline Derivatives This Example provides another representative solid-phase combmatorial synthesis of a library which contains approximately 2380 derivatives of 4-aryltetrahydroquinolines (THQs).
1. Reaction of the Mixture of Resin-Bound Aminobenzoic Acids with Aldehydes and 3,4-Dimethoxystyrene Seventy individual Tea-bags containing mixtures of 17 aminobenzamide-resins (30 mg, calc. 25 mmole) prepared in Example 1 above were added to each solution of 70 aldehydes (1 M) in DMF (10 mL) and cooled in the freezer (−10° C.) for 15–30 minutes. After cooling, 2.96 mL of 3,4-dimethoxystyrene (2M final concentration) was added and the solution cooled in the freezer again for 15–30 minutes. To which 0.77 mL of trifluoroacetic acid (1M) was added and the cyclization reaction shaken for 45–50 hours at room temperature. The 4-(3,4-dimethoxyphenyl) tetrahydroquinoline controls and mixtures were washed and cleaved off the resin according to the procedures in Example 1.

EXAMPLE 3

Combinatorial Library of 3-Methyl-4-(2,4,5-Trimethoxyphenyl)Tetrahydroquinoline Derivatives This Example provides another representative solid-phase combinatorial synthesis of a library which contains approximately 2380 derivatives of 4-aryltetrahydroquinolines (THQs).
1. Reaction of the Mixture of Resin-Bound Aminobenzoic Acids with Aldehydes and 2,4,5-Trimethoxropenylbenzene Seventy individual Tea-bags containing mixtures of 17 aminobenzamide-resins (30 mg, calc. 25 mmole) prepared in Example 1 above were added to each solution of 70 aldehydes (1 M) in DMF (10 mL) and cooled in the freezer (−10° C.) for 15–30 minutes. To which 1.94 mL of cis-2,4,5-trimethoxystyrene (1M final concentration) was added and the solution cooled in the freezer again for 15–30 minutes. To the cooled solution, 0.77 mL of trifluoroacetic acid (1M) was added and the cyclization reaction shaken for 45–50 hours at room temperature. The 3-methyl-4-(2,4,5-dimethoxyphenyl)tetrahydroquinoline controls and mixtures were washed and cleaved off the resin according to the procedures in Example 1.

EXAMPLE 4

Combinatorial Library of 4-(N-Methylacetamide) Tetrahydroquinoline Derivatives

This Example provides another representative solid-phase combinatorial synthesis of a library which contains approximately 2380 derivatives of 4-amidotetrahydroquinolines (THQs).
1. Reaction of the Mixture of Resin-Bound Aminobenzoic Acids with Aldehydes and N-Methyl-N-Vinylacetamide Seventy individual Tea-bags containing mixtures of 17 aminobenzamide-resins (30 mg, calc. 25 mmole) prepared as reported in Example 1 above were added to each solution of 70 aldehydes (1 M) in DCM (10 mL) and cooled in the freezer (−10° C.) for 15–30 minutes. After cooling, 1.04 mL of N-methyl-N-vinylacetamide (1M final concentration) was added and the solution cooled in the freezer again for 15–30 minutes. To the solution, 0.77 mL of trifluoroacetic acid (1M) was added and the cyclization reaction shaken for 45–50 hours at room temperature. The 4-N-methylacetamide)tetrahydroquinoline controls and mixtures were washed and cleaved off the resin according to the procedures in Example 1.

EXAMPLE 5

Combinatorial Library of 4-(2-pyrrolidone) Tetrahydroquinoline Derivatives

This Example provides another representative solid-phase combinatorial synthesis of a library which contains approximately 2380 derivatives of 4-amidotetrrhydroquinolines (THQs).

1. Reaction of the Mixture of Resin-Bound Aminobenzoic Acids with Aldehydes and N-Vinyl-2-pyrrolidone Seventy individual Tea-bags containing mixtures of 17 aminobenzamide-resins (30 mg, calc. 25 mmole) prepared as reported in Example 1 above were added to each solution of 70 aldehydes (1 M) in DCM (10 mL) and cooled in the freezer (−10° C.) for 15–30 minutes. To the cooled solution, 1.07 mL of N-vinyl-2-pyrrolidone (1M final concentration) was added and the solution cooled in the freezer again for 15–30 minutes. After cooling, 0.77 mL of trifluoroacetic acid (1M) was added and the cyclization reaction shaken for 45–50 hours at room temperature. The 4-(2-pyrrolidone) tetrahydroquinoline controls and mixtures where washed and cleaved off the resin according to the procedures in Example 1.

EXAMPLE 6

Combinatorial Library of Branched 4 (4Methoxyphenyl)Tetrahydroquinoline Derivatives This Example provides a representative solid-phase combinatorial synthesis of a library which contains 39,440 derivatives of Branched 4-aryltetrahydroquinolines (THQs).

Following the above Reaction Scheme II, preparation of a library containing the THQs involves the following steps. Briefly, first, L and D N-BOC p-nitrophenylalanine were attached to MBHA resin using tea-bags. After removal of the BOC protecting group the nitrogen is acylated with 170 acid derivatives creating variation of the $R^8$ substituent, again employing the tea-bags to carry out the operations. The acylated products were mixed by appropriate resin mixing techniques and the nitro group converted to an amino functionality by reduction. The 2 subgroups (L or D Branch) were distributed into tea-bags and reacted with 58 aldehydes and 4-methoxystyrene in the presence of trifluoroacetic acid to generate new 4-(4-methoxyphenyl)tetrahydroquinoline derivatives. After standard HF cleavage the individual mixtures varying at $R^8$ and constant at $Y—R^1$ and $R^5$, each a mixture containing 340 individual compounds, including enantiomers, which can then be tested for biological activity.

The individual acids which can be used to prepare with a library of 39,440 THQs include the following: acetic acid, α,α,α-trifluoro-m-toluic acid, α,α,α-trifluoro-o-toluic acid, α,α,α-trifluoro-p-toluic acid, α-cyclohexylphenylacetic acid, α-methylcinnamic acid, benzoic acid, butyric acid, chromone-2-carboxylic acid, crotonic acid, cyclobutanecarboxylic acid, cycloheptanecarboxylic acid, cyclohexanebutyric acid, cyclohexanecarboxylic acid, cyclohexanepropionic acid, cyclohexylacetic acid, cyclopentanecarboxylic acid, cyclopentylacetic acid, ethoxyacetic acid, formic acid, heptanoic acid, hydrocinnamic acid, isobutyric acid, isonicotinic acid, isovaleric acid, lauric acid, m-anisic acid, m-toluic acid, m-tolylacetic acid, methoxyacetic acid, nicotinic acid, niflumic acid, o-anisic acid, o-toluic acid, octanoic acid, p-anisic acid, p-toluic acid, p-tolylacetic acid, phenoxyacetic acid, phenylacetic acid, picolinic acid, piperonylic acid, propionic acid, pyrrole-2-carboxylic acid, tert-butylacetic acid, tetrahydro-2-furoic acid, tetrahydro-3-furoic acid, tiglic acid, trans-3-hexenoic acid, trans-cinnamic acid, trans-styrylacetic acid, trimethylacetic acid, triphenylacetic acid, vinylacetic acid, xanthene-9-carboxylic acid, 1-isoquinolinecarboxylic acid, 1-naphthylacetic acid, 3,5-dimethyl-p-anisic acid, 1-napthoic acid, 1-phenyl-1-cyclopropanecarboxylic acid, 2,3 -dichlorobenzoic acid, 3,5-dimethoxybenzoic acid, 2,3-methoxybenzoic acid, 2,4-dichlorobenzoic acid, 2,4-difluorobenzoic acid, 2,4-dimethoxybenzoic acid, 2,4-dimethylbenzoic acid, 2,4-hexadienoic acid, 2,5-dichlorobenzoic acid, 2,5-dimethylbenzoic acid, 2,6-dichlorobenzoic acid, 2,6-difluorobenzoic acid, 2,6-dimethoxybenzoic acid, 2-(trifluoromethyl)cinnamic acid, 3-(3,4,5-trimetboxypbenyl)propionic acid, 3-bromophenylacetic acid, 3-(3,4-dimethoxyphenyl)propionic acid, 2-bromobenzoic acid, 2-chloro-4,5-difluorobenzoic acid, 2-chloro-4-fluorophenylacetic acid, 2-chlorobenzoic acid, 2-ethoxybenzoic acid, 2-ethyl-2-hexenoic acid, 2-ethylbutyric acid, 2-ethylhexanoic acid, 2-fluorobenzoic acid, 2-furoic acid, 2-methylbutyric acid, 2-methylcyclopropanecarboxylic acid, 2-naphthylacetic acid, 99%, 2-napthoic acid, 2-norbornaneacetic acid, 3-(2-methoxyphenyl)propionic acid, 2-phenylbutyric acid, 3,5-dimethylbenzoic acid, 2-propylpentanoic acid, 2-pyrazinecarboxylic acid, 2-thiopheneacetic acid, 2-thiophenecarboxylic acid, 3,3,3-triphenylpropionic acid, 3,3-diphenylpropionic acid, 3,4,5-triethoxybenzoic acid, 3,4,5-trimetboxybenzoic acid, 3-benzoylpropionic acid, 3,4, 5-trimethoxycinnamic acid, 3,4,5-trimethoxyphenylacetic acid, 3,4-dichlorobenzoic acid, 3,4-dichloropbenylacetic acid, 3,4-difluorobenzoic acid, 3,4-dimethoxybenzoic acid, 3,4-dimethylbenzoic acid, 3,5,5-trimethylhexanoic acid, 3,5-bis(trifluoromethyl)benzoic acid, 3,5-dichlorobenzoic acid, (2,5-dimethoxyphenyl)acetic acid, (2-naphthoxy) acetic acid, (3,4-dimethoxyphenyl)acetic acid, 3-chlorobenzoic acid, (4-pyridylthio)acetic acid, (α,α,α-trifluoro-m-tolyl)acetic acid, trans-3-(3-pyridyl)acrylic acid, (methylthio)acetic acid, (phenylthio)acetic acid, 1-(4-chlorophenyl)-1-cyclopentanecarboxylic acid, 3-bromobenzoic acid, 3-cyanobenzoic acid, 1-adamantaneacetic acid, 3-cyclopentylpropionic acid, 3-dimethylaminobenzoic acid, 3-fluoro-4-methylbenzoic acid, 3-fluorobenzoic acid, 3-fluorophenylacetic acid, 3-iodo-4-methylbenzoic acid, 3-methoxyphenylacetic acid, 3-methyl-2-thiophenecarboxaldehyde, 3-methylvaleric acid, 3-phenoxybenzoic acid, 3-phenylbutyric acid, 3-thiopheneacetic acid, 4'-ethylbiphenylcarboxylic acid, 4-(diethylamino)benzoic acid, 4-benzoylbenzoic acid, 4-biphenylacetic acid, 4-biphenylcarboxylic acid, 4-bromobenzoic acid, 4-bromophenylacetic acid, 4-butylbenzoic acid, 4-chlor-o-anisic acid, 4-chlorobenzoic acid, 4-chlorocinnamic acid, 4-cyanobenzoic acid, 4-dimethylaminobenzoic acid, 4-ethoxybenzoic acid, 4-ethoxyphenylacetic acid, 4-ethylbenzoic acid, 4-fluorobenzoic acid, 4-fluorophenylacetic acid, 4-iodobenzoic acid, 4-isobutyl-α-methylphenylacetic acid, 4-isopropoxybenzoic acid, 4-isopropylbenzoic acid, 4-methoxyphenylacetic acid, 4-methyl-1-cyclohexanecarboxylic acid, 4-methylcyclohexaneacetic acid, 4-methylvaleric acid, 4-tert-butyl-cyclohexanecarboxylic acid, 5-bromo-2-chlorobenzoic acid, 5-bromonicotinic acid, 5-phenylvaleric acid, 6-chloronicotinic acid, individual aldehydes which can be employed are as follows: cyclohexanecarboxaldehyde, salicylaldehyde, trimethylacetaldehyde, 1-napthaldehyde, 2,3,4-trifluorobenzaldebyde, 2,3-difluorobenzaldehyde, 2,5-difluorobenzaldehyde, 2,5-dimethylbenzaldehyde, 2-bromobenzaldehyde, 2-chloro-5-nitrobenzaldehyde, 2-ethylbutyraldehyde, 2-nitro-5-chlorobenzaldehyde, 2-nitrobenzaldehyde, 2-pyridinecarboxaldehyde, 3,4-(methylenedioxy)-6-nitrobenzaldehyde, 3,4difluorobenzaldehyde, 3-(3,4-dichlorophenoxy) benzaldehyde, 3-bromobenzaldehyde, 3-fluorobenzaldehyde, 3-nitro-4-chlorobenzaldehyde, 3-nitrobenzaldehyde, 4-bromobenzaldehyde, 4-fluorobenzaldehyde, 4-nitrobenzaldehyde, 2,3- dimethylvaleraldehyde, 3-methoxy-2-nitrobenzaldehyde, 4-chloro-3-nitrobenzaldehyde.

1. Coupling of L or D p-Nitrophenylalanine to MBHA Resin

Polypropylene mesh packets (Tea-bags, ~5") of (5 g each, 0.89 meq/g) MBHA resin were prepared, washed with DCM (2×, ~25 ml each), neutralized with 5% diisopropylethylamine/dichloromethane (DIEA/DCM) (3×, ~25 ml each), and washed with DCM (2×, ~25 ml each). Each resin packet set is individually coupled 2–4 hrs by adding 2.5×L or D N-BOC p-nitrobenzoic acid (0.5 M)in 1:1 DMF/DCM solvent system followed by 2.5× diisopropylcarbodiimide (DIC) in DCM (0.5 M) and HOBt (2.5×). Following coupling completion, resin packets were washed with DCM (2×), DMF (2×), and DCM (1×) and MeOH (1×). The N-BOC protecting group was removed by shaking the bags with a solution of 55% TFA in DCM at room temperature for 30 mins. The liquid was decanted and the packets were washed with DCM (3×), 5% DIEA in DCM (3×). After drying under vacuum 4–12 hrs, each individual packet was then opened and the resin transferred in 75 mg (calc. 63 mmole) portions to a small labeled Tea-bags (~1.5" square) for use in subsequent chemistry.

2. Acylation of L and D p-Nitrophenylalanine

Groups of the resin packets (2×75 mg and a 30 mg) were individually coupled with 170 different acids overnight (~16 hrs) by adding 5×acid (0.5 M) in 1:1 DCM solvent system followed by 5×diisopropylcarbodiimide (DIC) in DCM (0.5 M) and HOBt (5×). Following coupling completion, resin packets were washed with DCM (2×), DMF (2×), and DCM (1×) and MeOH (1×). The 30 mg bags from each of the 170 acid reactions were cleaved by standard HF procedures and the products analyzed (See Table 2 below). One of the 75 mg bags from each acid of the reaction was opened and combined into one large Tea-bag (5" square) and each was then mixed in DCM for 30 min. After drying under vacuum the resin-bound acid mixtures sets were distributed in 30 mg portions into 141 Tea-bags for use in subsequent chemistry.

TABLE 2

Experimental Data for N-Acylated 4-Nitrophenylalanine

| No. | N-Acyl Substituent ($R^1$) | HPLC RT [25 cm (1) or 5 cm (s) column] | Expected MW | Observed MW |
|---|---|---|---|---|
| 1 | acetyl | 21.77(1) | 251.31 | (ND) |
| 2 | α-cyclohexylphenylacetyl | 43.60(1) | 409.33 | (ND) |
| 3 | α-methylcinnamoyl | 37.03(1) | 353.4 | (ND) |
| 4 | α,α,α-trifluoro-m-toluoyl | 37.12(1) | 381.33 | (ND) |
| 5 | α,α,α-trifluoro-o-toluoyl | 34.18(1) | 381.33 | (ND) |
| 6 | α,α,α-trifluoro-p-toluoyl | 37.92(1) | 381.33 | (ND) |
| 7 | benzoyl | 30.99(1) | 313.31 | (ND) |
| 8 | butyroyl | 27.14(1) | 279.32 | (ND) |
| 9 | crotonoyl | 26.52(1) | 277.3 | (ND) |
| 10 | cyclobutanecarboxyl | 29.65(1) | 291.33 | (ND) |
| 11 | cycloheptanecarboxyl | 35.88(1) | 333.41 | (ND) |
| 12 | cyclohexanebutyroyl | 41.29(1) | 361.51 | (ND) |
| 13 | cyclohexanecarboxyl | | 319.41 | (ND) |
| 14 | cyclohexanepropionoyl | 38.72(1) | 347.43 | (ND) |
| 15 | cyclohexylacetyl | 35.32(1) | 333.41 | (ND) |
| 16 | cyclopentanecarboxyl | 30.82(1) | 305.35 | (ND) |
| 17 | cyclopentylacetyl | 33.48(1) | 319.38 | (ND) |
| 18 | ethoxyacetyl | 2.04(s) | 295.32 | (ND) |
| 19 | 4-chlorocinnamoyl | 3.90(s) | 373.82 | (ND) |
| 20 | 4-cyanobenzoyl | 3.22(s) | 338.34 | (ND) |
| 21 | hydrocinnamoyl | 34.00(1) | 341.41 | (ND) |
| 22 | 4-dimethylaminobenzoyl | 3.11(s) | 356.4 | (ND) |
| 23 | 4-ethoxybenzoyl | 3.53(s) | 357.39 | (ND) |
| 24 | isobutyroyl | 26.86(1) | 279.32 | (ND) |
| 25 | isonicotinoyl | 21.51(1) | 314.32 | (ND) |
| 26 | 4-ethoxyphenylacetyl | 3.47(s) | 371.41 | (ND) |
| 27 | isovaleroyl | 29.78(1) | 293.34 | (ND) |
| 28 | 4-ethylbenzoyl | 3.71(s) | 341.39 | 341.9 |
| 29 | m-anisoyl | 32.11(1) | 343.36 | (ND) |
| 30 | m-toluoyl | 33.73(1) | 327.36 | (ND) |
| 31 | m-tolylacetyl | 34.29(1) | 341.39 | (ND) |
| 32 | methoxyacetyl | | 281.29 | (ND) |
| 33 | nicotinoyl | 22.09(1) | 314.31 | (ND) |
| 34 | niflumoyl | 4.32(s) | 473.43 | (ND) |
| 35 | o-anisoyl | 4.51(s) | 343.36 | 343.9 |
| 36 | o-toluoyl | 32.03(1) | 327.36 | (ND) |
| 37 | octanoyl | 4.17(s) | 335.42 | (ND) |
| 38 | p-anisoyl | 32.16(1) | 343.41 | (ND) |
| 39 | p-toluoyl | 33.65(1) | 327.41 | (ND) |
| 40 | p-tolylacetyl | 34.28(1) | 341.39 | (ND) |
| 41 | phenoxyacetyl | 3.62(s) | 343.36 | 343.9 |
| 42 | phenylacetyl | 3.44(s) | 327.41 | (ND) |
| 43 | picolinoyl | 3.22(s) | 314.32 | 315.0(M+1) |
| 44 | piperonoyl | 31.23(1) | 357.34 | (ND) |
| 45 | propionoyl | 2.62(s) | 261.25 | |
| 46 | pyrrole-2-carboxyl | 2.90(s) | 302.31 | (ND) |
| 47 | 4-fluoro-α-methylphenylacetyl | 4.74(s) | 359.38 | 359.8 |
| 48 | 4-fluorobenzoyl | 3.29(s) | 331.32 | (ND) |

TABLE 2-continued

Experimental Data for N-Acylated 4-Nitrophenylalanine

| No. | N-Acyl Substituent (R¹) | HPLC RT [25 cm (1) or 5 cm (s) column] | | Expected MW | Observed MW |
| --- | --- | --- | --- | --- | --- |
| 49 | 4-fluorophenylacetyl | 2.80 | (s) | 345.35 | (ND) |
| 50 | tert-butylacetyl | 32.57 | (1) | 307.41 | (ND) |
| 51 | tetrahydro-2-furoyl | 2.61/2.68 | (s) | 307.33 | 307.9 |
| 52 | tetrahydro-3-furoyl | 2.39/2.45 | (s) | 307.33 | 307.9 |
| 53 | tigloyl | 3.17 | (s) | 291.33 | (ND) |
| 54 | trans-3-(3-pyridyl)acroyl | | | 340.36 | (ND) |
| 55 | trans-3-hexenoyl | 32.34 | (1) | 305.35 | (ND) |
| 56 | trans-cinnamoyl | | | 339.41 | (ND) |
| 57 | trans-styrylacetyl | 34.80 | (1) | 353.4 | (ND) |
| 58 | trimethylacetyl | 40.52 | (1) | 293.31 | 294.0(M+1) |
| 59 | triphenylacetyl | 4.89 | (s) | 479.54 | (ND) |
| 60 | 4-isobutyl-α-methylphenylacetyl | 3.33 | (s) | 397.5 | (ND) |
| 61 | vinylacetyl | 26.32 | (1) | 277.3 | (ND) |
| 62 | xanthene-9-carboxyl | 3.57 | (s) | 417.44 | (ND) |
| 63 | (2,5-dimethoxyphenyl)acetyl | | | 387.41 | (ND) |
| 64 | (2-naphthoxy)acetyl | 3.84 | (s) | 393.42 | (ND) |
| 65 | (3,4-dimethoxyphenyl)acetyl | 29.03 | (1) | 387.41 | (ND) |
| 66 | (4-pyridylthio)acetyl | 19.81 | (1) | 360.41 | 361.2(M+#) |
| 67 | (α,α,α-trifluoro-m-tolyl)acetyl | | | 395.36 | (ND) |
| 68 | (methylthio)acetyl | 2.68 | (s) | 297.35 | (ND) |
| 69 | (phenylthio)acetyl | 3.51 | (s) | 359.42 | (ND) |
| 70 | 1-(4-chlorophenyl)-1-cyclopentanecarboxyl | 27.83/28.67 | (1) | 415.9 | 416 |
| 71 | α-adamantaneacetyl | 40.50 | (1) | 385.48 | (ND) |
| 72 | 1-naphthylacetyl | 3.90 | (s) | 377.42 | (ND) |
| 73 | 1-napthoyl | 3.64 | (s) | 363.39 | 363.8 |
| 74 | 1-phenyl-1-cyclopropanecarboxyl | 38.07 | (1) | 353.4 | (ND) |
| 75 | 4-iodobenzoyl | 3.79 | (s) | 439.23 | (ND) |
| 76 | 4-isopropoxybenzoyl | 4.38 | (s) | 371.41 | (ND) |
| 77 | 2,3-dichlorobenzoyl | 35.78 | (1) | 382.22 | (ND) |
| 78 | 4-methoxyphenylacetyl | 3.94 | (s) | 357.39 | (ND) |
| 79 | 2,3-dimethoxybenzoyl | 3.61 | (s) | 373.39 | (ND) |
| 80 | 2,4-dichlorobenzoyl | 36.44 | (1) | 382.22 | (ND) |
| 81 | 2,4-difluorobenzoyl | 3.40 | (s) | 349.32 | (ND) |
| 82 | 4-methyl-1-cyclohexanecarboxyl | 3.21 | (s) | 333.41 | (ND) |
| 83 | 2,4-dimethoxybenzoyl | 33.78 | (1) | 373.39 | (ND) |
| 84 | 2,4-dimethylbenzoyl | 3.78 | (s) | 341.39 | (ND) |
| 85 | 2,4-hexadienoyl | 3.42 | (s) | 303.34 | (ND) |
| 86 | 2,5-dichlorobenzoyl | 3.82 | (s) | 382.22 | (ND) |
| 87 | 2,5-dimethylbenzoyl | 3.76 | (s) | 341.39 | (ND) |
| 88 | 2,6-dichlorobenzoyl | 3.58 | (s) | 382.22 | 381.9 |
| 89 | 2,6-difluorobenzoyl | 3.35 | (s) | 349.31 | (ND) |
| 90 | 4-methylcyclohexaneacetyl | 3.84 | (s) | 347.44 | (ND) |
| 91 | 2,6-dimethoxybenzoyl | 3.37 | (s) | 373.39 | (ND) |
| 92 | 2-(trifluoromethyl)-cinnamoyl | 4.27 | (s) | 407.37 | (ND) |
| 93 | 4-methylvaleroyl | 3.33 | (s) | 307.37 | (ND) |
| 94 | 2-bromobenzoyl | 3.52 | (s) | 392.23 | (ND) |
| 95 | 2-chloro-4,5-difluorobenzoyl | 3.83 | (s) | 383.76 | (ND) |
| 96 | 2-chloro-4-fluorophenylacetyl | 3.70 | (s) | 379.8 | (ND) |
| 97 | 2-chlorobenzoyl | 3.47 | (s) | 347.78 | (ND) |
| 98 | 2-ethoxybenzoyl | 3.67 | (s) | 357.39 | (ND) |
| 99 | 2-ethyl-2-hexenoyl | 4.03 | (s) | 333.41 | (ND) |
| 100 | 2-ethylbutyroyl | 3.41 | (s) | 307.37 | (ND) |
| 101 | (+/−)-2-ethylhexanoyl | 3.99 | (s) | 335.42 | (ND) |
| 102 | 2-fluorobenzoyl | 3.47 | (s) | 331.32 | (ND) |
| 103 | 2-furyl | 3.03 | (s) | 303.29 | (ND) |
| 104 | 4-hydroxyquinoline-2-carboxyl | | | 380.38 | (ND) |
| 105 | (+/−)-2-methylbutyroyl | 3.10 | (s) | 293.34 | (ND) |
| 106 | 2-methylcyclopropanecarboxyl | 3.10 | (s) | 291.33 | (ND) |
| 107 | 2-naphthylacetyl | 3.91 | (s) | 377.42 | (ND) |
| 108 | 2-napthoyl | 3.78 | (s) | 363.39 | (ND) |
| 109 | 2-norbornaneacetyl | 3.86 | (s) | 345.41 | (ND) |

TABLE 2-continued

Experimental Data for N-Acylated 4-Nitrophenylalanine

| No. | N-Acyl Substituent (R¹) | HPLC RT [25 cm (l) or 5 cm (s) column] | | Expected MW | Observed MW |
|---|---|---|---|---|---|
| 110 | 2-phenylbutyroyl | 3.88 | (s) | 355.41 | (ND) |
| 111 | 2-propylpentanoyl | 3.96 | (s) | 335.42 | (ND) |
| 112 | 2-pyrazinecarboxyl | 2.74 | (s) | 315.31 | (ND) |
| 113 | 2-thiopheneacetyl | 3.32 | (s) | 333.38 | (ND) |
| 114 | 3,3,3-triphenylpropionoyl | 4.60 | (s) | 493.59 | (ND) |
| 115 | 3,3-diphenylpropionoyl | 4.26 | (s) | 417.51 | (ND) |
| 116 | 3,4,5-triethoxybenzoyl | 4.16 | (s) | 445.51 | (ND) |
| 117 | 3,4,5-trimethoxybenzoyl | 3.45 | (s) | 403.41 | (ND) |
| 118 | 3,4,5-trimethoxycinnamoyl | 3.69 | (s) | 429.45 | (ND) |
| 119 | 3,4-dichlorobenzoyl | 4.17 | (s) | 382.22 | (ND) |
| 120 | 3,4-dichlorophenylacetyl | | | 396.61 | (ND) |
| 121 | 3,4-difluorobenzoyl | 3.71 | (s) | 349.32 | (ND) |
| 122 | 4-imidazolecarboxyl | | | 303.3 | (ND) |
| 123 | 4-tert-butyl-cyclohexanecarboxyl | 4.32 | (s) | 375.49 | 375.9 |
| 124 | 3,4-dimethoxybenzoyl | 3.29 | (s) | 373.41 | (ND) |
| 125 | 3,4-dimethylbenzoyl | 3.77 | (s) | 341.39 | (ND) |
| 126 | 3,5,5-trimethylhexanoyl | 4.21 | (s) | 349.45 | (ND) |
| 127 | 3,5-bis(trifluoromethyl)benzoyl | 4.49 | (s) | 449.33 | (ND) |
| 128 | 5-bromo-2-chlorobenzoyl | 3.65 | (s) | 426.67 | (ND) |
| 129 | 5-bromonicotinoyl | 3.18 | (s) | 393.22 | (ND) |
| 130 | 5-phenylvaleroyl | 3.80 | (s) | 369.44 | (ND) |
| 131 | 3,5-dichlorobenzoyl | 4.18 | (s) | 382.22 | (ND) |
| 132 | 6-chloronicotinoyl | 3.10 | (s) | 348.77 | (ND) |
| 133 | 3,5-dimethoxybenzoyl | | | 372.39 | (ND) |
| 134 | 3,5-dimethyl-p-anisoyl | 3.82 | (s) | 371.41 | (ND) |
| 135 | 3,5-dimethylbenzoyl | 3.79 | (s) | 341.39 | (ND) |
| 136 | 3-(2-methoxyphenyl)propionoyl | 3.53 | (s) | 371.41 | (ND) |
| 137 | 3-(3,4,5-trimethoxyphenyl)propionoyl | 3.43 | (s) | 431.47 | (ND) |
| 138 | 3,4,5-trimethoxyphenylacetyl | 3.21 | (s) | 417.44 | (ND) |
| 139 | 3-(3,4-dimethoxyphenyl)propionoyl | 3.35 | (s) | 401.44 | (ND) |
| 140 | heptanoyl | 3.61 | (s) | 321.4 | (ND) |
| 141 | 3-benzoylpropionoyl | 3.52 | (s) | 369.4 | (ND) |
| 142 | 3-bromobenzoyl | 3.87 | (s) | 392.23 | (ND) |
| 143 | 3-bromophenylacetyl | 3.79 | (s) | 406.26 | (ND) |
| 144 | chromone-2-carboxyl | 3.29 | (s) | 381.36 | (ND) |
| 145 | 5-methyl-2-pyrazinecarboxyl | | | 329.34 | (ND) |
| 146 | 3-chlorobenzoyl | 3.61 | (s) | 347.78 | (ND) |
| 147 | 3-cyanobenzoyl | 3.42 | (s) | 338.34 | (ND) |
| 148 | 3-cyclopentylpropionoyl | 3.89 | (s) | 333.41 | (ND) |
| 149 | 3-dimethylaminobenzoyl | 2.58 | (s) | 356.4 | (ND) |
| 150 | 3-fluoro-4-methylbenzoyl | 3.80 | (s) | 345.35 | (ND) |
| 151 | 3-fluorobenzoyl | 3.52 | (s) | 331.32 | (ND) |
| 152 | 3-fluorophenylacetyl | 3.50 | (s) | 345.35 | (ND) |
| 153 | 6-methoxy-α-methyl-2-napthaleneacetyl | | | 421.48 | (ND) |
| 154 | 3-iodo-4-methylbenzoyl | 4.18 | (s) | 453.26 | (ND) |
| 155 | formyl | | | 237.24 | (ND) |
| 156 | 6-methylnicotinoyl | | | 328.35 | (ND) |
| 157 | 1-isoquinolinecarboxyl | 3.47 | (s) | 364.35 | (ND) |
| 158 | lauryl | 4.98 | (s) | 391.53 | (ND) |
| 159 | 3-methoxyphenylacetyl | 3.25 | (s) | 357.39 | ((ND) |
| 160 | 3-methyl-2-thiophenecarboxyl | 3.28 | (s) | 333.39 | (ND) |
| 161 | 3-methylvaleroyl | 3.48 | (s) | 307.37 | (ND) |
| 162 | 3-phenoxybenzoyl | 4.05 | (s) | 405.43 | (ND) |
| 163 | 3-phenylbutyroyl | 3.57 | (s) | 355.41 | (ND) |
| 164 | 3-thiopheneacetyl | 3.15 | (s) | 333.38 | (ND) |
| 165 | 4'-ethyl-4-biphenylcarboxyl | | | 417.49 | (ND) |
| 166 | 4-(diethylamino)benzoyl | 2.76 | (s) | 384.45 | (ND) |
| 167 | 4-benzoylbenzoyl | 3.79 | (s) | 417.44 | (ND) |
| 168 | 4-biphenylacetyl | 3.91 | (s) | 403.46 | (ND) |
| 169 | 4-biphenylcarboxyl | 4.01 | (s) | 389.41 | (ND) |
| 170 | 4-bromobenzoyl | 3.61 | (s) | 392.23 | (ND) |
| 171 | 4-bromophenylacetyl | 3.56 | (s) | 406.26 | (ND) |
| 172 | 4-butylbenzoyl | 4.20 | (s) | 369.44 | (ND) |

TABLE 2-continued

Experimental Data for N-Acylated 4-Nitrophenylalanine

| No. | N-Acyl Substituent (R$^1$) | HPLC RT [25 cm (1) or 5 cm (s) column] | Expected MW | Observed MW |
|---|---|---|---|---|
| 173 | 4-chloro-o-anisoyl | 3.71(s) | 377.8 | (ND) |
| 174 | 4-chlorobenzoyl | 3.53(s) | 347.78 | (ND) |

3. Reduction of the Mixtures of Resin-Bound L and D N-Acylated p-Nitroahenylalanine All of the Tea-bags from the previous step were placed in a large container and shaken with a solution of SnCl$_2$.2H$_2$O in DMF (2.0 M, 1.5 L) at room temperature overnight (~16 hrs). The packets were washed with DMF (3×), methanol (2×), DCM (2×), air-dried for 30 min and then dried under vacuum for 1–2 hrs. The bags were sorted into appropriate sets for use in the subsequent chemistry.

4. Reaction of the Mixtures of Resin-Bound L and D N-Acylated p-Aminophenylalanine with Aldehydes and 4-Methoxystyrene Following the procedure in Example 1 30 mg Tea-bags (separately 170 bags of the L and the D series branched N-acylated p-aminophenylalanine and 1 sibling bag containing L-N-propanoyl p-aminophenylalanine) were added to each solution of 25 aldehydes (1 M) in DMF (10 mL) and cooled in freezer (–10° C.) for 15–30 minutes. Following, 2.42 mL of 4-methoxystyrene (2M final concentration) was added and the solution cooled in the freezer again for 15–30 minutes. After cooling, 0.77 mL of trifluoroacetic acid (1M) was added and the cyclization reaction shaken for 45–50 hours at room temperature. Following completion of the 4-(4-methoxyphenyl)tetrahydroquinoline formation, the resin packets were washed with DCM (2×), DMF (2×), and DCM (1×), MeOH (1×) and dried under vacuum.

The branched 4-(4-methoxyphenyl)tetrahydroquinoline controls (L-N-propanoyl p-aminophenylalanine sibling bags) and mixtures were cleaved off the resin by treatment with HF (liquid (l)) at –15° C. for 2 hrs in the presence of anisole scavenger followed by warming to room temperature while removing HF (gaseous (g)) with a nitrogen stream. Results for the control bags are given in Table 3.

TABLE 3

Branched-2-Substituted-4(4-methoxyphenyl)tetrahydroquinoline derivatives.

| No. | 2-Substituent (R$^5$) R$^8$ = Propanoyl | HPLC RT (5 cm) | Calc. MW | Obs.* MW |
|---|---|---|---|---|
| 1 | 1-napthyl | 5.75 | 507.63 | 508.4 |
| 2 | 1,1-dimethyl-4-butenyl | 6.04 | 463.62 | 464.8 |
| 3 | 2,3,4-trifluorophenyl | 5.74 | 511.55 | 512.1 |
| 4 | 2,3,5-trichlorophenyl | 6.01 | 560.91 | 561.1 |
| 5 | 2,3-difluorophenyl | 5.55 | 493.56 | 494.2 |
| 6 | 1,2-dimethylbutyl | 4.83 | 465.64 | 466.5 |
| 7 | 2,4-dichlorophenyl | 6.25 | 526.46 | 526.2 |
| 8 | 2,5-difluorophenyl | 5.57 | 493.56 | 494.2 |
| 9 | 2,5-dimethylphenyl | 5.43 | 485.63 | 486.5 |
| 10 | 2,6-difluorophenyl | 5.35 | 493.56 | 494.1 |
| 11 | 2-bromophenyl | 5.8 | 536.48 | 536.4/5 |
| 12 | 2-chloro-5-nitrophenyl | 5.57 | 537.02 | 537.3 |
| 13 | 2-cyanophenyl | 3.77 | 482.58 | 483.3 |
| 14 | 1-ethylpropyl | 4.59 | 451.61 | 452.3 |
| 15 | 2-fluorophenyl | 5.35 | 475.56 | 476.2 |
| 16 | 2-methylcarboxyphenoxymethyl | 4.66 | 531.61 | 532.3 |
| 17 | 2-methoxy-1-naphthyl | 4.72 | 537.66 | 538.5 |
| 18 | 1-methylpropyl | 4.3 | 437.58 | 438.8 |

TABLE 3-continued

Branched-2-Substituted-4(4-methoxyphenyl)tetrahydroquinoline derivatives.

| No. | 2-Substituent (R$^5$) R$^8$ = Propanoyl | HPLC RT (5 cm) | Calc. MW | Obs.* MW |
|---|---|---|---|---|
| 19 | 2-methyldecany | 6.63 | 535.77 | 536.4 |
| 20 | 1-methylbutyl | 4.57 | 451.61 | 452.7 |
| 21 | 2-nitro-5-chlorophenyl | 5.77 | 537.02 | 537.3 |
| 22 | 2-nitrophenyl | 5.37 | 502.57 | 503.6 |
| 23 | 2-pridylmethyl | 0.34 | 458.56 | 459.3 |
| 24 | 3,4-methylenedioxy-6-nitrophenyl | 5.44 | 546.58 | 547.5 |
| 25 | 3,4-difluorophenyl | 5.53 | 493.56 | 494.2 |
| 26 | 3,5-bis(trifluoromethylphenyl) | 6.38 | 593.57 | 594.1 |
| 27 | 3,5-dichlorophenyl | 6.52 | 526.46 | 527.3 |
| 28 | 3,3,4-dichlorophenoxyphenyl | 6.75 | 618.56 | 618.4 |
| 29 | 3-bromophenyl | 5.74 | 536.48 | 536.4/5 |
| 30 | 3-carboxyphenyl | 4.48 | 501.58 | 502.2 |
| 31 | 3-cyanophenyl | 5.34 | 482.58 | 582.7 |
| 32 | 3-fluorophenyl | 5.29 | 475.56 | 476.3 |
| 33 | (3-chromonyl)methyl | 4.9 | 525.55 | 526.4 |
| 34 | 3-furyl | 4.75 | 447.54 | 448.2 |
| 35 | 3-hydroxy-4-nitrophenyl | | | |
| 36 | 3-hydroxyphenyl | 4.2 | 473.57 | 474.2 |
| 37 | 3-methoxy-2-nitrophenyl | 5.42 | 532.6 | 533.5 |
| 38 | 3-nitro-4-chlorophenyl | 5.79 | 537.02 | 537.2 |
| 39 | 3-nitrophenyl | 5.37 | 502.57 | 503.5 |
| 40 | 3-phenoxyphenyl | 5.48 | 549.67 | 550.8 |
| 41 | 3-phenylbutyryl | 4.8 | 499.66 | 500.4 |
| 42 | 3-pyridinemethyl | 0.51 | 458.56 | 459.5 |
| 43 | 4-bromo-2-thiophenylmethyl | 5.78 | 542.5 | 542.5/5 |
| 44 | 4-bromophenyl | 5.68 | 536.48 | 536.4/5 |
| 45 | 4-chloro-3-nitrophenyl | 5.77 | 537.02 | 537.4 |
| 46 | 4-cyanophenyl | 5.18 | 482.58 | 483.3 |
| 47 | 4-fluorophenyl | 5.09 | 475.56 | 476.4 |
| 48 | 4-nitrophenyl | 5.44 | 502.57 | 503.2 |
| 49 | 4-quinolinylmethyl | 3.65 | 508.62 | 509.5 |
| 50 | 5-bromo-2-hydroxyphenyl | 4.72 | 552.47 | 552.5/5 |
| 51 | 5-nitro-2-furyl | 5.02 | 492.54 | 493.3 |
| 52 | 6-methyl-2-pyridinecarboxyl | 0.35 | 472.59 | 4.73.5 |
| 53 | phenyl | 5.14 | 457.57 | 458.5 |
| 54 | cyclohexanemethyl | 4.65 | 463.62 | 464.6 |
| 55 | 1,2-dihydroxyethyl | 0.35 | 441.53 | 442.5 |
| 56 | 2-hydroxyphenyl | 4.25 | 473.57 | 474.3 |
| 57 | p-trifluoromethylphenyl | 6.26 | 525.57 | 526.3 |
| 58 | tert-butyl | 4.58 | 437.58 | 438.3 |

*"Obs. MW" stands for Observed Molecular Weight

EXAMPLE 7

Combinatorial Library of Branched 4-(3,4-Dimethoxyphenyl)tetrahydroquinoline Derivatives This Example provides a representative solid-phase combinatorial synthesis of a library which contains 35,360 derivatives of branched 4-aryltetrahydroquinolines (THQs).

1. Reaction of the Mixtures of Resin-Bound L and D N-Acylated p-Aminophenylalanine with Aldehydes and 3,4-Dimethoxystyrene Following the procedure in Example 6, 30 mg Tea-bags (mixtures for both L and D Series of 170 branched N-acylated-4-aminophenylalanine) were added to each of 52 separate aldehyde solutions (1 M) in DMF (10 mL) and cooled in freezer (−10° C.) for 15–30 minutes. After cooling, 2.96 mL of 3,4dimethoxystyrene (2M final concentration) was added and the solution again cooled in the freezer for 15–30 minutes. Following, 0.77 mL of trifluoroacetic acid (1M) was added and the cyclization reaction shaken for 45–50 hours at room temperature. Following completion of the branched 4-(3,4-dimethoxyphenyl)tetrahydroquinoline formation, the resin packets were washed and cleaved according to the procedure in Example 6. Results for control samples are given in Table 4.

TABLE 4

Branched-2-Substituted-4-(3,4-Dimethoxyphenyl)tetrahydroquinoline derivatives.

| No. | 2-Substituent ($R^5$) $R^8$ = Propanoyl | HPLC RT (5 cm) | Calc. MW | Obs.* MW |
|---|---|---|---|---|
| 1 | 1-napthyl | 5.51 | 381.47 | 538.2 |
| 2 | 1,1-dimethyl-4-butenyl | 4.81 | 381.47 | 494.6 |
| 3 | 2,3,4-trifluorophenyl | 5.42 | 381.47 | 542.7 |
| 4 | 2,3,5-trichlorophenyl | 5.75 | 381.47 | 591.2 |
| 5 | 2,3-difluorophenyl | 5.2 | 381.47 | 524.7 |
| 6 | 1,2-dimethylbutyl | 4.56 | 381.47 | 496.7 |
| 7 | 2,4-dichlorophenyl | 4.95 | 381.47 | 556.8 |
| 8 | 2,5-difluorophenyl | 5.21 | 381.47 | 525 |
| 9 | 2,5-dimethylphenyl | 5.09 | 381.47 | 516.7 |
| 10 | 2,6-difluorophenyl | 4.96 | 381.47 | 524.3 |
| 11 | 2-bromophenyl | 5.43 | 381.47 | 566.7/5 |
| 12 | 2-chloro-5-nitrophenyl | 5.33 | 381.47 | 567.6 |
| 13 | 2-chloro-6-fluorophenyl | 4.65 | 381.47 | 540.1 |
| 14 | 1-ethylpropyl | 4.27 | 381.47 | 482.7 |
| 15 | 2-fluorophenyl | 5.03 | 381.47 | 506.6 |
| 16 | 2-methoxy-1-naphthyl | 4.43 | 381.47 | 568.6 |
| 17 | 1-methylpropyl | 3.82 | 381.47 | 468.5 |
| 18 | 2-methyldecanyl | 6.25 | 381.47 | 566.3 |
| 19 | 1-methylbutyl | 4.38 | 381.47 | 482.7 |
| 20 | 2-nitro-5-chlorophenyl | 7.11 | 381.47 | 569.6 |
| 21 | 2-nitrophenyl | 5.07 | 381.47 | 533.4 |
| 22 | 2-pyridylmethyl | 0.26 | 381.47 | 489.7 |
| 23 | 3,4-difluorophenyl | 5.23 | 381.47 | 524.8 |
| 24 | 3,5-bis(trifluoromethyl)phenyl | 6.07 | 381.47 | 624.8 |
| 25 | 3,5-dichlorophenyl | 5.83 | 381.47 | 556.7 |
| 26 | 3-(3,4-dichlorophenoxy)phenyl | 6.44 | 381.47 | 648.6/6 |
| 27 | 3-bromo-4-fluorophenyl | 5.51 | 381.47 | 584.75 |
| 28 | 3-bromophenyl | 5.43 | 381.47 | 566.9/5 |
| 29 | 3-carboxyphenyl | 4.74 | 381.47 | 531.8 |
| 30 | 3-cyanophenyl | 4.61 | 381.47 | 512.6 |
| 31 | 3-fluorophenyl | 4.98 | 381.47 | 506.5 |
| 32 | (3-chromonyl)methyl | 4.57 | 381.47 | 556.4 |
| 33 | 3-furyl | 0.26 | 381.47 | 474.8 |
| 34 | 3-hydroxy-4-nitrophenyl | 5 | 381.47 | 549.1 |
| 35 | 3-hydroxyphenyl | 3.87 | 381.47 | 504.7 |
| 36 | 3-methoxy-2-nitrophenyl | 5.12 | 381.47 | 563.6 |
| 37 | 3-nitro-4-chlorophenyl | 5.45 | 381.47 | 567.6 |
| 38 | 4-bromo-2-thiophenylmethyl | 5.49 | 381.47 | 572.4/5 |
| 39 | 4-bromophenyl | 5.36 | 381.47 | 566.6/5 |
| 40 | 4-carboxyphenyl | 4.09 | 381.47 | 532.6 |
| 41 | 4-chloro-3-nitrophenyl | 5.42 | 381.47 | 567.4 |
| 42 | 4-fluorophenyl | 7.41 | 381.47 | 505.6 |
| 43 | 4-nitrophenyl | 5.15 | 381.47 | 533.3 |
| 44 | 4-quinolinylmethyl | 0.9 | 381.47 | 539.8 |
| 45 | 5-nitro-2-furyl | 4.47 | 381.47 | 523.7 |
| 46 | 6-methyl-2-pyndinecarboxyl | 0.26 | 381.47 | 503.7 |
| 47 | 9-ethyl-3-carbazolecarboxyl | 5.39 | 381.47 | 605.2 |
| 48 | phenyl | 4.56 | 381.47 | 488.5 |
| 49 | cyclohexanemethyl | 4.29 | 381.47 | 494.3 |
| 50 | 1,2-dihydroxyethyl | 4.39 | 381.47 | 472.6 |
| 51 | 2-hydroxyphenyl | 3.95 | 381.47 | 504.5 |
| 52 | tert-butyl | 4.27 | 381.47 | 468.6 |

*"Obs. MW" stands for Observed Molecular Weight

EXAMPLE 8
Combinatorial Library of Branched 3-Methyl-4-(2,4,5-Trimethoxyphenyl)Tetrahydroquinoline Derivatives This Example provides a representative solid-phase combinatorial synthesis of a library which contains approximately 27,200 derivatives of branched 4-aryltetrahydroquinolines (THQs).

1. Reaction of the Mixtures of Resin-Bound L and D N-Acylated p-Aminophenylalanine with Aldehydes and 2,4,5-Trimethoxyropeylbenzene Following the procedure in Example 6, 30 mg Tea-bags (mixtures for both L and D Series of 170 Branched N-Acylated4-aminophenylalanine) are added to each of 40 separate solutions aldehydes (1 M) in DMF (10 mL) and cooled in freezer (−10° C.) for 15–30 minutes. After cooling, 1.94 mL of cis-2,4,5-trimethoxypropenylbenzene (1M final concentration) is added and the solution again cooled in the freezer for 15–30 minutes. Next, 0.77 mL of trifluoroacetic acid (1M) is added and the cyclization reaction is shaken for 45–50 hours at room temperature. Following completion of the branched 3-methyl-4-(2,4,5-trimethoxyphenyl) tetrahydroquinoline formation, the resin packets are washed and cleaved according to the procedure in Example 6.

EXAMPLE 9

Combinatorial Library of Branched 4-Methylacetamide)tetrahydroquinoline Derivatives This Example provides a representative solid-phase combinatorial synthesis of a library which contains approximately 27,200 derivatives of branched 4-amidotetrahydroquinolines (THQs).

1. Reaction of the Mixtures of Resin-Bound L and D N-Acylated p-Aminophenylalanine with Aldehydes and N-Methyl-N-vinylacetamide Following the procedure in Example 6, 30 mg Tea-bags (mixtures for both L and D series of 170 branched N-acylated-4-aminophenylalanine) are added to each solution of 40 aldehydes (1 M) in DCM (10 mL) and cooled in freezer (−10° C.) for 15–30 minutes. Thereafter, 1.04 mL of N-methyl-N-vinylacetamide (1M final concentration) is added and the solution is cooled in the freezer again for 15–30 minutes. After cooling, 0.77 mL of trifluoroacetic acid (1M) is added and the cyclization reaction is shaken for 45–50 hours at room temperature. Following completion of the branched 4-(N-methyl-N-acetyl-amino) tetrahydroquinoline formation, the resin packets are washed and cleaved according to the procedure in Example 6.

EXAMPLE 10

Combinatorial Library of Branched 4-(2-Pyrrolidone)tetrahydroquinoline Derivatives This Example provides a representative solid-phase combinatorial synthesis of a library which contains approximately 27,200 derivatives of branched 4-amidotetrrhydroquinolines (THQs).

1. Reaction of the Mixtures of Resin-Bound L and D N-Acylated p-Aminophenylalanine with Aldehydes and N-Vinyl-Pyrrlidone Following the procedure in Example 6, 30 mg Tea-bags (mixtures for both L and D series of 170 branched N-acylated-4-aminophenylalanine) are added to each solution of 40 aldehydes (1 M) in DCM (10 mL) and cooled in freezer (−10° C.) for 15–30 minutes. To the solution, 1.07 mL of N-methyl-N-vinylacetamide (1M final concentration) is added and the solution is again cooled in the freezer for 15–30 minutes. Following, 0.77 mL of trifluoroacetic acid (1M) is added and the cyclization reaction is shaken for 45–50 hours at room temperature. Following completion of the branched 4-(N-pyrrolidinyl)tetrahydroquinoline formation, the resin packets are washed and cleaved according to the procedure in Example 6.

EXAMPLE 11

Combinatorial Library of Branched 4-(4-Methoxyphenyl)Quinoline Derivatives

This Example provides a representative solid-phase combinatorial synthesis of a library which contains 14,280 derivatives of branched 4-arylquinolines 1. Oxidation of the Mixtures of Resin-Bound L and D 6-Branched(N-Acylated) 4-(4-Methoxyphenyl)Tetrthydroquinolines to L and D 6-Branched(N-Acylated) 4-(4-Methoxyphenyl)Quinolines Following the chemistry procedures employed in Example 6 to prepare the THQ mixtures, 84 30 mg Tea-bags (mixtures for both L and D series of 170 6-branched(N-acylated) 4(4-methoxyphenyl)tetrahydroquinolines) are treated with 2.5 mL of 32% peracetic acid in 50 mL of acetic acid at room temperature for 4–6 hours. The resin bags are washed 3×MeOH, 1×DCM, 1×DMF, 2×DCM and 1×MeOH then dried under vacuum for 8–16 hours. The 4-(4-Methoxyphenyl)quinolines products are cleaved from the resin with HF using standard procedures as described in Example 1 above.

TABLE 5

Branched-2-Substituted-4-(4-Methoxyphenyl)Quinoline Derivatives.

| No. | 2-Substituent ($R^5$) R8 = Propanoyl | HPLC RT (5 cm) | Calc. MW | Obs.* MW |
|---|---|---|---|---|
| 1 | 1-napthyl | 4.51 | 503.63 | 504.4 |
| 2 | 2,3,4-trifluorophenyl | 5.27 | 507.55 | 508.3 |
| 3 | 2,3,5-trichlorophenyl | 6.01 | 556.91 | 556.7/5 |
| 4 | 2-3-difluorophenyl | 4.92 | 489.56 | 490.3 |
| 5 | 2-4-dichlorophenyl | 5.21 | 522.46 | 522.6/5 |
| 6 | 2-5-difluorophenyl | 5.08 | 489.56 | 490.3 |
| 7 | 2 5-dimethylphenyl | 4.37 | 481.63 | 482.4 |
| 8 | 2 6-difluorophenyl | 4.61 | 489.56 | 490.2 |
| 9 | 2-bromophenyl | 4.56 | 532.48 | 532.6/5 |
| 10 | 2-chloro-6-fluorophenyl | 4.82 | 506.01 | 506.4 |
| 11 | 1-ethylpropyl | 3.99 | 447.61 | 448.2 |
| 12 | 2-fluorophenyl | 4.34 | 471.56 | 472.3 |
| 13 | 2-methylcarboxyphenoxymethyl | 4.09 | 527.61 | 528.4 |
| 14 | 2-methox -1-naphthyl | 4.45 | 533.66 | 534.4 |
| 15 | 2-nitro-5-chlorophenyl | 5.68 | 533.02 | 534.1 |
| 16 | 2-nitrophenyl | 4.66 | 498.57 | 499.6 |
| 17 | 2-pridylmethyl | 0.34 | 454.56 | 455.8 |
| 18 | 3,4-methylenedioxy-6-nitrophenyl | 4.63 | 542.58 | 543.7 |
| 19 | 3,4-difluorophenyl | 4.95 | 489.56 | 490.3 |
| 20 | 3,5-dichlorophenyl | 6.15 | 522.46 | 522.7 |
| 21 | 3-(3,4-dichlorophenoxy)phenyl | 5.88 | 614.56 | 614.7/6 |
| 22 | 3-bromphenyl | 5.04 | 532.48 | 532.715 |
| 23 | 3-carboxyphenyl | 3.96 | 497.58 | 498.5 |
| 24 | 3-cyanophenyl | 4.8 | 478.58 | 479.7 |
| 25 | 3-fluorophenyl | 4.61 | 471.56 | 472.4 |
| 26 | 3-furyl | 3.81 | 443.54 | 444.3 |
| 27 | 3-hydroxyphenyl | 3.79 | 469.57 | 470.4 |
| 28 | 3-nitro-4-chlorophenyl | 5.71 | 533.02 | 533.6 |
| 29 | 3-phenoxyphenyl | 5.16 | 545.67 | 546.8 |
| 30 | 3-phenylbutyryl | 4.47 | 495.66 | 494.5 |
| 31 | 4-bromo-2-thiophenylmethyl | 5.87 | 538.5 | 538.6/5 |
| 32 | 4-bromophenyl | 4.86 | 532.48 | 432.7/5 |
| 33 | 4-carboxyphenyl | 4.01 | 497.58 | 498.5 |
| 34 | 4-cyanophenyl | 4.81 | 478.58 | 4,795 |
| 35 | 4-fluorophenyl | 4.33 | 471.56 | 472.4 |
| 36 | 4-nitrophenyl | 5.21 | 498.57 | 499.5 |
| 37 | 5-bromo-2-hydroxyphenyl | 6.02 | 548.47 | 548.8/5 |
| 38 | 9-ethyl-3-carbazolecarboxyl | 4.94 | 570.73 | 571.8 |
| 39 | phenyl | 4.09 | 453.57 | 454.5 |

EXAMPLE 12

Combinatorial Library of Branched 4-(3,4-Dimethoxyphenyl)Quinoline Derivatives This Example provides a representative solid-phase combinatorial synthesis of a library which contains 15,300 derivatives of branched 4-arylquinolines.

1. Oxidation of the Mixtures of Resin-Bound L and D 6-Branched(N-Acylated) 4-(3,4-Dimethoxyphenyl)Tetrahydroquinolines to L and D 6-Branched(N-Acylated) 4-(3,4-Dimethoxyphenyl)Quinolines Following the chemistry procedures employed in Example 6,90 THQ mixtures are prepared. The 140 30 mg Tea-bags (mixtures for both L and D series of 170 6-branched(N-acylated) 4-(3,4-dimethoxyphenyl) tetrahydroquinolines) are treated with 2.5 mL of 32% peracetic acid in 50 mL of acetic acid at room temperature for 4–6 hours. The resin bags are washed 3×MeOH, 1×DCM, 1×DMF, 2×DCM and 1×MeOH and then dried under vacuum for 8–16 hours. The branched 4-(3,4-dimethoxyphenyl)quinoline products are cleaved from the resin with HF using standard procedures as described in Example 1 above.

TABLE 6

Branched-2-Substituted-4-(3,4-Dimethoxyphenyl)Quinoline Derivatives.

| No. | 2-Substituent ($R^5$) R8 = Propanoyl | HPLC RT (5 cm) | Calc. MW | Obs. MW |
|---|---|---|---|---|
| 1 | 1-napthyl | 4.38 | 533.65 | 534.3 |
| 2 | 2,3,4-trifluorophenyl | 5.04 | 537.57 | 538.5 |
| 3 | 2,3,5-trichlorophenyl | 5.72 | 586.93 | 586.9/588. |
| 4 | 2,3-difluorophenyl | 4.69 | 519.58 | 520.7 |
| 5 | 2,4-dichlorophenyi | 4.95 | 552.48 | 552.9/554. |
| 6 | 2,5-difluorophenyl | 4.71 | 519.58 | 520.6 |
| 7 | 2,5-dimethylphenyl | 4.15 | 511.65 | 512.8 |
| 8 | 2,6-difluorophenyl | 4.36 | 519.58 | 520.4 |
| 9 | 2-bromophenyl | 4.33 | 562.5 | 562.7/564. |
| 10 | 2-chloro-6-fluorophenyl | 4.55 | 536.03 | 537 |
| 11 | 1-ethylpropyl | 0.38 | 477.63 | 478.7 |
| 12 | 2-fluorophenyl | 4.12 | 501.58 | 502.5 |
| 13 | 2-methylcarboxyphenoxymethyl | 3.94 | 557.63 | 558.4 |
| 14 | 2-methoxy-1-naphthyl | 4.2 | 563.68 | 564.5 |
| 15 | 1-methylpropyl | 3.51 | 463.6 | 464.4 |
| 16 | 2-methyldecanyl | 5.26 | 561.79 | 562.5 |
| 17 | 1-methylbutyl | 0.28 | 477.63 | 478.4 |
| 18 | 2-pyridylmethyl | 0.26 | 484.58 | 485.9 |
| 19 | 3,4-(methylenedioxy)-6-nitrophenyl | 4.41 | 572.6 | 573.8 |
| 20 | 3,4-difluorophenyl | 4.76 | 519.58 | 520.6 |
| 21 | 3,5-dichlorophenyl | 5.97 | 552.48 | 552.7 |
| 22 | 3-(3,4-dichlorophenoxy)phenyl | 5.67 | 644.58 | 645 |
| 23 | 3-bromo-4-fluorophenyl | 5.04 | 580.49 | 581.1/582. |
| 24 | 3-bromophenyl | 4.83 | 562.5 | 563.9/565. |
| 25 | 3-carboxyphenyl | 3.85 | 527.6 | 528.3 |
| 26 | 3-cyanophenyl | 4.61 | 508.6 | 509.9 |
| 27 | 3-fluorophenyl | 4.4 | 501.58 | 502.6 |
| 28 | 3-furyl | 0.26 | 473.56 | 474.8 |
| 29 | 3-hydroxyphenyl | 3.61 | 499.59 | 500.8 |
| 30 | 3-nitro-4-chlorophenyl | 5.41 | 563.04 | 563.8 |
| 31 | 3-phenoxyphenyl | 4.99 | 575.69 | 576.9 |
| 32 | 4-bromo-2-thiophenylmethyl | 5.39 | 568.52 | 568.9/570. |
| 33 | 4-bromophenyl | 4.69 | 562.5 | 563.0/565. |
| 34 | 4-carboxyphenyl | 0.32 | 527.6 | 528.7 |
| 35 | 4-chloro-3-nitrophenyl | 5.38 | 563.04 | 563.6 |
| 36 | 4-fluorophenyl | 5.45 | 501.58 | 502.1 |
| 37 | 4-nitrophenyl | 4.98 | 528.59 | 529.7 |
| 38 | 4-quinolinylmethyl | 0.41 | 534.64 | 535.9 |
| 39 | 5-bromo-2-hydroxyphenyl | 5.83 | 578.49 | 578.8/580. |
| 40 | 6-methyl-2-pyridinecarboxyl | 0.26 | 498.61 | 499.7 |
| 41 | 9-ethyl-3-carbazolecarboxyl | 4.76 | 600.75 | 601.4 |
| 42 | phenyl | 3.85 | 483.59 | 484.4 |
| 43 | 2-hydroxyphenyl | 4.76 | 499.59 | 500.4 |
| 44 | p-trifluoromethylphenyl | 5.16 | 551.59 | 552.4 |
| 45 | tert-butyl | 3.5 | 463.6 | 464.4 |

All journal article and reference citations provided above, in parentheses or otherwise, whether previously stated or not, are incorporated herein by reference.

Although the invention has been described with reference to the examples provided above, it should be understood that

We claim:
1. A single compound of the formula:

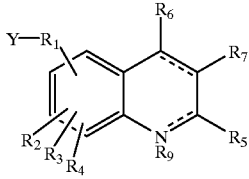

Formula I wherein in the above Formula I, the dashed lines ( - - - ) means fully saturated or fully unsaturated and further wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

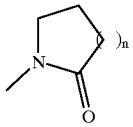

wherein n is from 1 to 2, and a group of the formula:

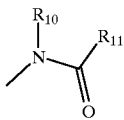

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is $C(O)NHR^{12}$, wherein $R^{12}$ is a hydrogen atom, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

2. The single compound of claim 1, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

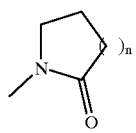

wherein n is from 1 to 2, and a group of the formula:

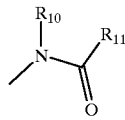

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom and $C_1$ to $C_{10}$ alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is $C(O)NHR^{12}$, wherein $R^{12}$ is a hydrogen atom.

3. The single compound of claim 1, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted) aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

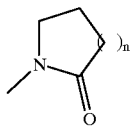

wherein n is from 1 to 2, and a group of the formula:

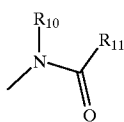

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

4. The single compound of claim 1, wherein:

$R^1$ is absent or present, and, when present is selected from the group consisting of $CH_2NHCO$ and $CH_2CH(NHR^8)$, wherein $R^8$ is selected from the group consisting of acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/−)-2-ethylhexanoyl, 2-fluorobenzoyl, 4-hydroxyquinoline-2-carboxyl, (+/−)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl)propionoyl, heptanoyl, 3-benzoylpropionoyl, 3-bromobenzoyl, 3-bromophenylacetyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, lauryl, 3-methoxyphenylacetyl, 3-methylvaleroyl, 3-phenoxybenzoyl, 3-phenylbutyroyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, and 4-chlorobenzoyl;

$R^2$ $R^3$, and $R^4$ are each, independently, selected from the group consisting of a hydrogen atom, hydroxy, fluoro, chloro, bromo, iodo, methyl, methoxy, nitro and —CH=CH—CH=CH—O fused to adjacent positions;

$R^5$ is selected from the group consisting of 1-methyl-2-pyrrolyl, 1-napthyl, 2,2-dimethyl-3-butenyl, 2,3,4-trifluorophenyl, 2,3,5-trichlorophenyl, 2,3-difluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-(3-oxapropanoic acid))phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-norbornene-2-yl, 6-methyl-2-pyridinyl, 9-ethyl-3-carbazolyl, phenyl, chloromethyl, cyclohexanyl, D,L-1,2-(dihydroxy)ethyl, carboxy, hydrogen atom, acetyl, 2-hydroxyphenyl, tribromomethyl, trifluoro-p-tolulyl, and 2-methyl-2-propyl;

$R^6$ is selected from the group consisting of 4-methoxyphenyl, 4-ethoxyphenyl, 3,4-dimethoxyphenyl, 2,4,5-trimethoxyphenyl, N-pyrrolidonyl, and N-methyl-N-acetyl-amino;

$R^7$ is selected from the group consisting of a hydrogen atom and methyl;

$R^9$ is a hydrogen atom; and

Y is $C(O)NH_2$.

5. The single compound of claim 1, wherein:

$R^1$ is $CH_2CH(NHR^8)$, wherein $R^8$ is selected from the group consisting of acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1- cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/-)-2-ethylhexanoyl, 2-fluorobenzoyl, 4-hydroxyquinoline-2-carboxyl, (+/-)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl)propionoyl, heptanoyl, 3-benzoylpropionoyl, 3-bromobenzoyl, 3-bromophenylacetyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, lauryl, 3-methoxyphenylacetyl, 3-methylvaleroyl, 3-phenoxybenzoyl, 3-phenylbutyroyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, 4-chlorobenzoyl; [acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tetrahydro-2-furoyl, tetrahydro-3-furoyl, tigloyl, trans-3-(3-pyridyl) acroyl, trans-3-hexenoyl, trans-cinnamoyl, trans-styrylacetyl, trimethylacetyl, triphenylacetyl, 4-isobutyl-α-methylphenylacetyl, -vinylacetyl, xanthene-9-carboxyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2 bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/-)-2-ethylhexanoyl, 2-fluorobenzoyl, 2-furyl, 4-hydroxyquinoline-2-carboxyl, (+/-)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 2-pyrazinecarboxyl, 2-thiopheneacetyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-imidazolecarboxyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl)propionoyl, heptanoyl, 3-benzoylpropionoyl, 3-bromobenzoyl, 3-bromophenylacetyl, chromone-2-carboxyl, 5-methyl-2-pyrazinecarboxyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, 1-isoquinolinecarboxyl, lauryl, 3-methoxyphenylacetyl, 3-methyl-2-thiophenecarboxyl, 3-methylvaleroyl, 3-phenoxybenzoyl, 3-phenylbutyroyl, 3-thiopheneacetyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, and 4-chlorobenzoyl;]

$R^2$ $R^3$, and $R^4$ are each, independently, a hydrogen atom;

$R^5$ is selected from the group consisting of 1-methyl-2-pyrrolyl, 1-napthyl, 2,2-dimethyl-3-butenyl, 2,3,4-trifluorophenyl, 2,3,5-trichlorophenyl, 2,3-difluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-(3-oxapropanoic acid)) phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-norbornene-2-yl, 6-methyl-2-pyridinyl, 9-ethyl-3-carbazolyl, phenyl, chloromethyl, cyclohexanyl, D,L-1,2-(dihydroxy) ethyl, carboxy, hydrogen atom, acetyl, 2-hydroxyphenyl, tribromomethyl, trifluoro-p-tolulyl, and 2-methyl-2-propyl;

$R^6$ is selected from the group consisting of 4-methoxyphenyl, 4-ethoxyphenyl, 3,4-dimethoxyphenyl, 2,4,5-trimethoxyphenyl, N-pyrrolidonyl, and N-methyl-N-acetyl-amino;

$R^7$ is selected from the group consisting of a hydrogen atom and methyl;

$R^9$ is a hydrogen atom; and

Y is $C(O)NH_2$.

6. The single compound of claim 1, wherein:

$R^1$ is absent or $CH_2NHCO$;

$R^2$ $R^3$, and $R^4$ are each, independently, selected from the group consisting of a hydrogen atom, hydroxy, fluoro, chloro, bromo, iodo, methyl, methoxy, nitro and —CH=CH—CH=CH— fused to adjacent positions;

$R^5$ is selected from the group consisting of 1-methyl-2-pyrrolyl, 1-napthyl, 2,2-dimethyl-3-butenyl, 2,3,4-trifluorophenyl, 2,3,5-trichlorophenyl, 2,3-difluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-oxa-3-propionoyl)-phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-norbornene-2-yl, 6-methyl-2-pyridinyl, 9-ethyl-3-carbazolyl, phenyl, chloromethyl, cyclohexanyl, D,L-1,2-(dihydroxy) ethyl, carboxy, hydrogen atom, acetyl, 2-hydroxyphenyl, tribromomethyl, trifluoro-p-tolulyl, and 2-methyl-2-propyl;

$R^6$ is selected from the group consisting of 4-methoxyphenyl, 4-ethoxyphenyl, 3,4-dimethoxyphenyl, 2,4,5-trimethoxyphenyl, N-pyrrolidonyl, and N-methyl-N-acetyl-amino;

$R^7$ is selected from the group consisting of a hydrogen atom and methyl;

$R^9$ is a hydrogen atom; and

Y is $C(O)NH_2$.

7. A single compound of the formula:

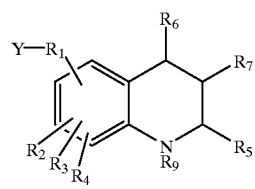

Formula I wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

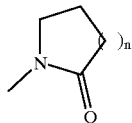

wherein n is from 1 to 2, and a group of the formula:

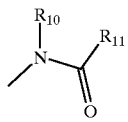

wherein $R_{10}$ and $R_{11}$ are, independently, selected from the group consisting of hydrogen, $C_1$ to $C_{10}$ alkyl, $C_1$ to $C_1$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is $C(O)NHR^{12}$, wherein $R^{12}$ is a hydrogen atom, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, guinolyl and substituted quinolyl;

or a salt thereof.

8. The single compound of claim 7, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

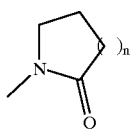

wherein n is from 1 to 2, and a group of the formula:

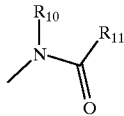

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom, $C_1$ to $C_{10}$ alkyl, and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is $C(O)NHR^{12}$, wherein $R^{12}$ is a hydrogen atom.

9. The single compound of claim 7, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted) aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

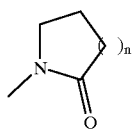

wherein n is from 1 to 2, and a group of the formula:

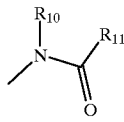

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

10. The single compound of claim 7, wherein:

$R^1$ is absent or present, and, when present is selected from the group consisting of $CH_2NHCO$ and $CH_2CH$ ($NHR^8$), wherein $R^8$ is selected from the group consisting of acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, (2,5-dimethoxyphenyl)acetyl, (2-naphthoxy)acetyl, (3,4-dimethoxyphenyl)acetyl, (4-pyridylthio)acetyl, (α,α, α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/-)-2-ethylhexanoyl, 2-fluorobenzoyl, 4-hydroxyquinoline-2-carboxyl, (+/-)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl) propionoyl, heptanoyl, 3-benzoylpropionoyl, 3-bromobenzoyl, 3-bromophenylacetyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, lauryl, 3-methoxyphenylacetyl, 3-methylvaleroyl, 3-phenoxybenzoyl, 3-phenylbutyroyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, and 4-chlorobenzoyl;

$R^2$ $R^3$, and $R^4$ are each, independently, selected from the group consisting of a hydrogen atom, hydroxy, fluoro, chloro, bromo, iodo, methyl, methoxy, nitro and —CH=CH—CH=CH— fused to adjacent positions;

$R^5$ is selected from the group consisting of 1-methyl-2-pyrrolyl, 1-napthyl, 2,2-dimethyl-3-butenyl, 2,3,4-trifluorophenyl; 2,3,5-trichlorophenyl, 2,3-difluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-(3-oxapropanoic acid)) phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-norbornene-2-yl, 6-methyl-2-pyridinyl, 9-ethyl-3-carbazolyl, phenyl, chloromethyl, cyclohexanyl, D,L-1,2-(dihydroxy) ethyl, carboxy, hydrogen atom, acetyl, 2-hydroxyphenyl, tribromomethyl, trifluoro-p-tolulyl, and 2-methyl-2-propyl;

$R^6$ is selected from the group consisting of 4-methoxyphenyl, 4-ethoxyphenyl, 3,4-dimethoxyphenyl, 2,4,5-trimethoxyphenyl, N-pyrrolidonyl, and N-methyl-N-acetyl-amino;

$R^7$ is selected from the group consisting of a hydrogen atom and methyl;

$R^9$ is a hydrogen atom; and

Y is $C(O)NH_2$.

11. The single compound of claim 7, wherein:

$R^1$ is $CH_2CH(NHR^8)$, wherein $R^8$ is selected from the group consisting of acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tigloyl, trans-3-(3-pyridyl)acroyl, trans-3-hexenoyl, trans-cinnamoyl, trats-styrylacetyl, trimethylacetyl, triphenylacetyl, 4-isobutyl-α-methylphenylacetyl, -vinylacetyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/−)-2-ethylhexanoyl, 2-fluorobenzoyl, 4-hydroxyquinoline-2-carboxyl, (+/−)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl) propionoyl, heptanoyl, 3-benzoylpropionoyl, 3-bromobenzoyl, 3-bromophenylacetyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, lauryl, 3-methoxyphenylacetyl, 3-methylvaleroyl, 3-pherioxybenzoyl, 3-phenylbutyroyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, 4-chlorobenzoyl; [acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tetrahydro-2-furoyl, tetrahydro-3-furoyl, tigloyl, trans-3-(3-pyridyl)acroyl, trans-3-hexenoyl, trans-cinnamoyl, trans-styrylacetyl, trimethylacetyl, triphenylacetyl, 4-isobutyl-α-methylphenylacetyl, -vinylacetyl, xanthene-9-carboxyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopiopanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4- dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/−)-2-ethylhexanoyl, 2-fluorobenzoyl, 2-furyl, 4-hydroxyquinoline-2-carboxyl, (+/−)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 2-pyrazinecarboxyl, 2-thiopheneacetyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-imidazolecarboxyl, 4-tert-butyl-cyclohexanecarboxyl, 3,4-dimethoxybenzoyl, 3,4-dimethylbenzoyl, 3,5,5-trimethylhexanoyl, 3,5-bis(trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl)propionoyl, heptanoyl, 3-benzoylpropionoyl, 3-bromobenzoyl, 3-bromophenylacetyl, chromone-2-carboxyl, 5-methyl-2-pyrazinecarboxyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, 1-isoquinolinecarboxyl, lauryl, 3-methoxyphenylacetyl, 3-methyl-2-thiophenecarboxyl, 3-methylvaleroyl, 3-phenoxybenzoyl, 3-phenylbutyroyl, 3-thiopheneacetyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, and 4-chlorobenzoyl;]

$R^2$, $R^3$, and $R^4$ are each, independently, a hydrogen atom;

$R^5$ is selected from the group consisting of 1-methyl-2-pyrrolyl, 1-napthyl, 2,2-dimethyl-3-butenyl, 2,3,4-trifluorophenyl, 2,3,5-trichlorophenyl, 2,3-difluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-(3-oxapropanoic acid))phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-norbornene-2-yl, 6-methyl-2-pyridinyl, 9-ethyl-3-carbazolyl, phenyl, chloromethyl, cyclohexanyl, D,L-1,2-(dihydroxy)ethyl, carboxy, hydrogen atom, acetyl, 2-hydroxyphenyl, tribromomethyl, trifluoro-p-tolulyl, and 2-methyl-2-propyl;

$R^6$ is selected from the group consisting of 4-methoxyphenyl, 4-ethoxyphenyl, 3,4-dimethoxyphenyl, 2,4,5-trimethoxyphenyl, N-pyrrolidonyl, and N-methyl-N-acetyl-amino;

$R^7$ is selected from the group consisting of a hydrogen atom and methyl;

$R^9$ is a hydrogen atom; and

Y is $C(O)NH_2$.

12. The single compound of claim 7, wherein:

$R^1$ is absent or $CH_2NHCO$;

$R^2$, $R^3$, and $R^4$ are each, independently, selected from the group consisting of a hydrogen atom, hydroxy, fluoro, chloro, bromo, iodo, methyl, methoxy, nitro and —CH═CH—CH═CH— fused to adjacent positions;

$R^5$ is selected from the group consisting of 1-methyl-2-pyrrolyl, 1-napthyl, 2,2-dimethyl-3-butenyl, 2,3,4-trifluorophenyl, 2,3,5-trichlorophenyl, 2,3-difluorophenyl, 1,2-dimethylbutyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 3-pentyl, 2-fluorophenyl, 2-(3-oxa-3-propionoyl)-phenyl, 2-methoxy-1-naphthyl, 2-butyl, 1-methyldecyl, 2-pentyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxy-4-nitro-phenyl, 3-hydroxyphenyl, 3-methoxy-2-nitro-phenyl, 3-nitro-4-chlorophenyl, 3-nitrophenyl, 3-phenoxyphenyl, 2-phenylpropyl, 3-pyridinyl, 4-bromophenyl, 4-carboxyphenyl, 4-chloro-3-nitro-phenyl, 4-cyanophenyl, 4-fluorophenyl, 4-nitrophenyl, 4-pyridinyl, 4-quinolinyl, 5-bromosalicyl, 5-norbornene-2-yl, 6-methyl-2-pyridinyl, 9-ethyl-3-carbazolyl, phenyl, chloromethyl, cyclohexanyl, D,L-1,2-(dihydroxy)ethyl, carboxy, hydrogen atom, acetyl, 2-hydroxyphenyl, tribromomethyl, trifluoro-p-tolulyl, and 2-methyl-2-propyl;

$R^6$ is selected from the group consisting of 4-methoxyphenyl, 4-ethoxyphenyl, 3,4-dimethoxyphenyl, 2,4,5-trimethoxyphenyl, N-pyrrolidonyl, and N-methyl-N-acetyl-amino;

$R^7$ is selected from the group consisting of a hydrogen atom and methyl;

$R^9$ is a hydrogen atom; and

Y is $C(O)NH_2$.

13. A single compound of the formula:

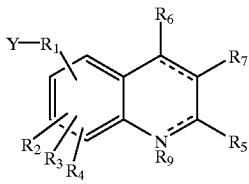

Formula I wherein in the above Formula I, the dashed lines ( - - - ) means fully saturated or fully unsaturated and further wherein:

$R^1$ is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

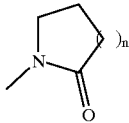

wherein n is from 1 to 2, and a group of the formula:

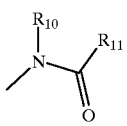

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

14. The single compound of claim 13, wherein:

$R^1$ is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula:
—$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

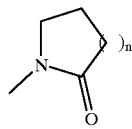

wherein n is from 1 to 2, and a group of the formula:

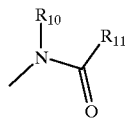

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom and $C_1$ to $C_{10}$ alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

15. The single compound of claim 13, wherein:
$R^1$ is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted) aminocarbonyl, protected (monosubstitituted) aminocarbonyl, (disubstituted)aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclicring, substituted heterocyclic ring, heteroaryl ring and substituted heteroaryl ring;

$R^6$ is selected from the group consisting of phenyl, substituted phenyl, a group of the formula:

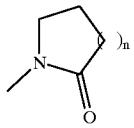

wherein n is from 1 to 2, and a group of the formula:

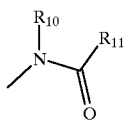

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

16. A single compound of the formula:

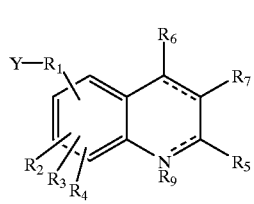

Formula I wherein in the above Formula I, the dashed lines ( - - - ) means fully saturated or fully unsaturated and further wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

—$(CH_2)_p$—Ar—$(CH_2)_q$— wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

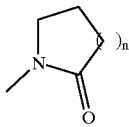

wherein n is from 1 to 2, and a group of the formula:

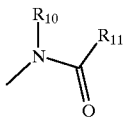

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of $C_1$ to $C_{10}$ alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

17. The single compound of claim 16, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

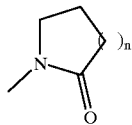

wherein n is from 1 to 2, and a group of the formula:

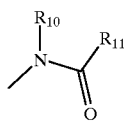

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is $C_1$ to $C_{10}$ alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

18. The single compound of claim 16, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted) aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

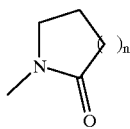

wherein n is from 1 to 2, and a group of the formula:

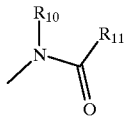

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is $C_1$ to $C_{10}$ alkyl;

$R^9$ is a hydrogen atom; and

Y is $C(O)NH_2$.

19. A single compound of the formula:

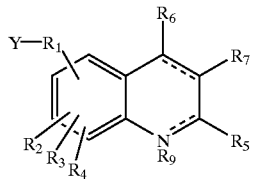

Formula I wherein in the above Formula I, the dashed lines ( - - - ) means fully saturated or fully unsaturated and further wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —CH$_2$CONH— and a group of the formula:

wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_3$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C^5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of naphthyl, substituted naphthyl, a group of the formula:

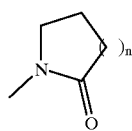

wherein n is from 1 to 2, and a group of the formula:

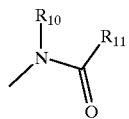

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $C_2OH$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

20. The single compound of claim 19, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —CH$_2$CONH—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of naphthyl, substituted naphthyl, a group of the formula:

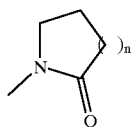

wherein n is from 1 to 2, and a group of the formula:

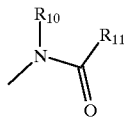

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom, $C_1$ to $C_{10}$ alkyl and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

21. The single compound of claim 19, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted) aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of the formula:

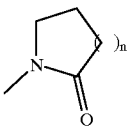

wherein n is from 1 to 2, and the formula:

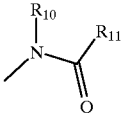

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

22. A single compound of the formula:

Formula I

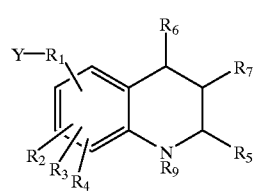

wherein:

$R^1$ selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

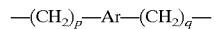
—$(CH_2)_p$—Ar—$(CH_2)_q$— wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2, R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

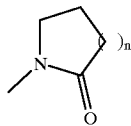

wherein n is from 1 to 2, and a group of the formula:

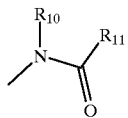

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt thereof.

23. The single compound of claim 22, wherein:

$R^1$ is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula:
—$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

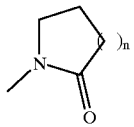

wherein n is from 1 to 2, and a group of the formula:

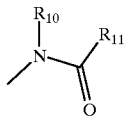

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom, $C_1$ to $C_{10}$ alkyl, and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

24. The single compound of claim 22, wherein:
$R^1$ is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted) aminocarbonyl, protected (monosubstitituted) aminocarbonyl, (disubstituted)aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

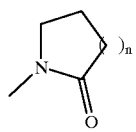

wherein n is from 1 to 2, and a group of the formula:

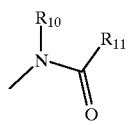

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

25. A single compound of the formula:

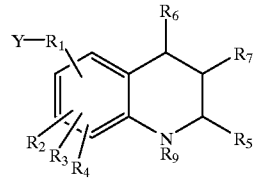

Formula I wherein:
$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

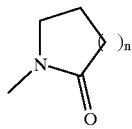

wherein n is from 1 to 2, and a group of the formula:

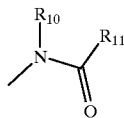

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt thereof.

26. The single compound of claim 25, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ Substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

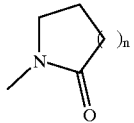

wherein n is from 1 to 2, and a group of the formula:

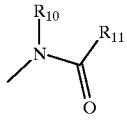

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of $C_1$ to $C_{10}$ alkyl and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

27. The single compound of claim 25, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted)aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

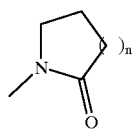

wherein n is from 1 to 2, and a group of the formula:

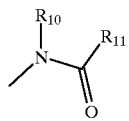

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is $C_1$ to $C_{10}$ alkyl;

$R^9$ is a hydrogen atom; and

Y is $C(O)NH_2$.

28. A single compound of the formula:

Formula I

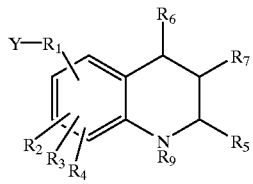

wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

—$(CH_2)_p$—Ar—$(CH_2)_q$— wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of naphthyl, substituted naphthyl, a group of the formula:

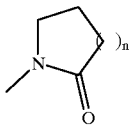

wherein n is from 1 to 2, and a group of the formula:

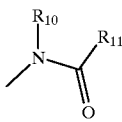

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt thereof.

29. The single compound of claim 28, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of naphthyl, substituted naphthyl, a group of the formula:

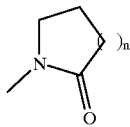

wherein n is from 1 to 2, and a group of the formula:

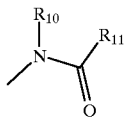

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom, $C_1$ to $C_{10}$ alkyl and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

30. The single compound of claim 28, wherein:

$R^1$ is absent or present and, when present, is selected from the group consisting of —$CH_2CONH$— and —$CH_2CH$ (NHR$^8$)—, wherein R$^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstituted)aminocarbonyl, (disubstituted) aminocarbonyl, $C_1$ to $C_4$ alkylsulfonyl, $C_7$ to $C_{12}$ phenylalkylsulfonyl, phenylsulfonyl, and substituted phenylsulfonyl;

R$^2$ R$^3$, and R$^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

R$^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

R$^6$ is selected from the group consisting of the formula:

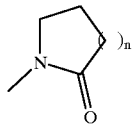

wherein n is from 1 to 2, and the formula:

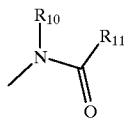

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

R$^7$ is selected from the group consisting of a hydrogen atom and $C_1$ to $C_{10}$ alkyl;

R$^9$ is a hydrogen atom; and

Y is C(O)NH$_2$.

31. A single compound of the formula:

Formula I

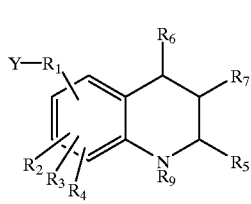

wherein:

R$^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —CH$_2$CONH— and a group of the formula:

wherein p and q are independently selected from a number 0 to 6, wherein both p and q are not both 0; and Ar is an aryl group selected from the group consisting of phenyl, substituted phenyl, heteroaryl ring and substituted heteroaryl ring;

R$^2$, R$^3$, and R$^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

R$^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

R$^6$ is selected from the group consisting of phenyl, substituted phenyl, naphthyl, substituted naphthyl, a group of the formula:

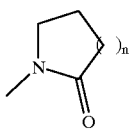

wherein n is from 1 to 2, and a group of the formula:

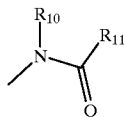

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, SH, $NHR^{12}$, $C(O)NHR^{12}$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt thereof.

32. The single compound of claim 31, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

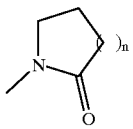

wherein n is from 1 to 2, and a group of the formula:

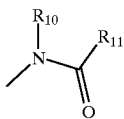

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom, $C_1$ to $C_{10}$ alkyl, and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$ and $C(O)NHR^{12}$, wherein $R^{12}$ is selected from the group consisting of a hydrogen atom, $C_1$ to $C_6$ alkyl and $C_1$ to $C_6$ substituted alkyl.

33. The single compound of claim 31, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted) aminocarbonyl, $C_1$ to $C_4$ alkylsulfonyl; $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

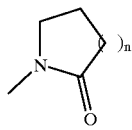

wherein n is from 1 to 2, and a group of the formula:

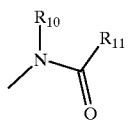

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

34. A single compound of the formula:

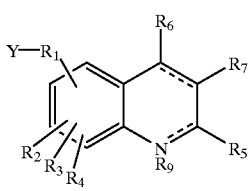

Formula I wherein in the above Formula I, the dashed lines ( - - - ) means fully saturated or fully unsaturated and further wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

—$(CH_2)_p$—Ar—$(CH_2)_q$— wherein p and q are independently selected from a number 0 to 6, wherein both p and q are not both 0;

and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

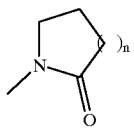

wherein n is from 1 to 2, and a group of the formula:

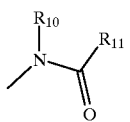

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms;

provided said cyclic $C_2$ to $C_7$ heteroalkylene and substituted cyclic $C_2$ to $C_7$ heteroalkylene are, respectively, quinolyl and substituted quinolyl;

provided, where Y is OH, SH or $NH_2$, $R^1$ is present;

provided, where Y is OH, $R^1$ is not methyl; and provided, where $R^5$ is absent, either Y is not $CO_2H$ or $R^1$ is not methyl;

or a salt of the 4-substituted quinoline.

35. The single compound of claim 34, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

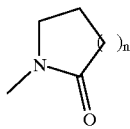

wherein n is from 1 to 2, and a group of the formula:

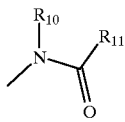

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom and $C_1$ to $C_{10}$ alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

36. The single compound of claim 34, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted) aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

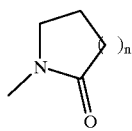

wherein n is from 1 to 2, and a group of the formula:

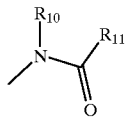

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ its selected from the group consisting of a hydrogen atom and $C_1$ to $C_{10}$ alkyl;

$R^9$ is a hydrogen atom; and

Y is $C(O)NH_2$.

37. A single compound of the formula:

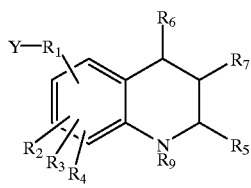

Formula I wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

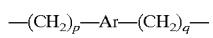

wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

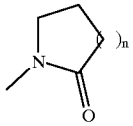

wherein n is from 1 to 2, and a group of the formula:

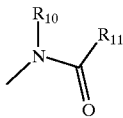

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl, $C_1$ to $C_{10}$ substituted alkyl, and a functionalized resin, provided said ring of said heterocyclic ring, substituted heterocyclic ring, heteroaryl ring or substituted heteroaryl ring contains one ring nitrogen atom and four or five ring carbon atoms;

provided said cyclic $C_2$ to $C_7$ heteroalkylene and substituted cyclic $C_2$ to $C_7$ heteroalkylene are, respectively, quinolyl and substituted quinolyl;

provided, where Y is OH, SH or $NH_2$, $R^1$ is present;

provided, where Y is OH, $R^1$ is not methyl; and provided, where $R^5$ is absent, either Y is not $CO_2H$ or $R^1$ is not methyl;

or a salt thereof.

38. The single compound of claim 37, wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, and a group of the formula: —$CH_2CONH$—;

$R^2$, $R^3$, and $R^4$ are, independently, selected from the group consisting of a hydrogen atom, halo, hydroxy, protected hydroxy, $C_1$ to $C_{10}$ alkyl, $C_1$ to $C_{10}$ substituted alkyl, $C_1$ to $C_7$ alkoxy, $C_1$ to $C_7$ substituted alkoxy, cyclic $C_2$ to $C_7$ alkylene, substituted cyclic $C_2$ to $C_7$ alkylene, and nitro;

$R^5$ is selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of a phenyl, substituted phenyl, naphthyl, substituted naphthyl, a group of the formula:

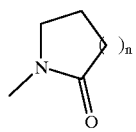

wherein n is from 1 to 2, and a group of the formula:

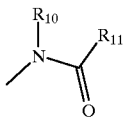

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, substituted phenyl, $C_7$ to $C_{12}$ phenylalkyl, and $C_7$ to $C_{12}$ substituted phenylalkyl;

$R^7$ is selected from the group consisting of a hydrogen atom, $C_1$ to $C_{10}$ alkyl, and $C_1$ to $C_{10}$ substituted alkyl;

$R^9$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, $NHR^{12}$, $C(O)NHR^{12}$, wherein $R^{12}$ is selected from the group consisting of a hydrogen atom, $C_1$ to $C_6$ alkyl and $C_1$ to $C_6$ substituted alkyl.

39. The single compound of claim 37, wherein:

$R^1$ is absent or present and, when present, is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted)aminocarbonyl, protected (monosubstitituted)aminocarbonyl, (disubstituted)aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$ $R^3$, and $R^4$ are each, independently, selected from the group consisting of a hydrogen atom, hydroxy, halo, $C_1$ to $C_6$ alkyl, $C_1$ to $C_7$ alkoxy, cyclic $C_2$ to $C_7$ alkylene, and nitro;

$R^5$ is selected from the group consisting of a hydrogen atom, carboxy, $C_1$ to $C_{10}$ alkyl, $C_1$ to $C_{10}$ substituted alkyl, $C_1$ to $C_{10}$ alkenyl, $C_1$ to $C_{10}$ substituted alkenyl, $C_3$ to $C_7$ cycloalkyl, $C_3$ to $C_7$ substituted cycloalkyl, phenyl, substituted phenyl, naphthyl, substituted naphthyl, heterocyclic ring, substituted heterocyclic ring, heteroaryl ring and substituted heteroaryl ring;

$R^6$ is selected from the group consisting of phenyl, substituted phenyl, a group of the formula:

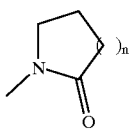

wherein n is from 1 to 2, and a group of the formula:

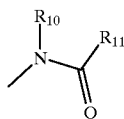

wherein $R_{10}$ and $R_{11}$ are, independently, selected from the group consisting of a hydrogen atom, $C_1$ to $C_{10}$ alkyl, $C_1$ to $C_{10}$ substituted alkyl, phenyl, and substituted phenyl;

$R^7$ is selected from the group consisting of a hydrogen atom and $C_1$ to $C_{10}$ alkyl;

$R^9$ is a hydrogen atom; and

Y is $C(O)NH_2$.

40. A single compound of the formula:

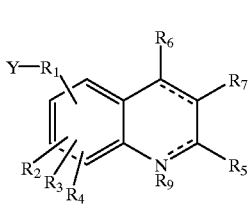

Formula I wherein in the above Formula I, the dashed lines ( - - - ) means fully saturated or fully unsaturated and further wherein:

$R^1$ is selected from the group consisting of —$CH_2CONH$— and —$CH_2CH(NHR^8)$—, wherein $R^8$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, $C_1$ to $C_6$ acyl, $C_1$ to $C_6$ substituted acyl, aminocarbonyl, protected aminocarbonyl, (monosubstituted) aminocarbonyl, protected (monosubstitituted) aminocarbonyl, (disubstituted)aminocarbonyl, $C_1$ to $C_4$ alkylsulfonyl, $C_7$ to $C_{12}$ phenylalkylsulfonyl, phenylsulfonyl, and substituted phenylsulfonyl;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of phenyl, substituted phenyl, naphthyl, substituted naphthyl, a group of the formula:

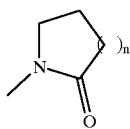

wherein n is from 1 to 2, and a group of the formula:

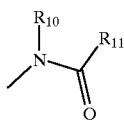

wherein $R^{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of hydrogen, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $NHR^{12}$, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

41. A single compound of the formula:

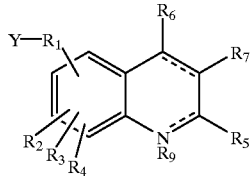

Formula I wherein in the above Formula I, the dashed lines ( - - - ) means fully unsaturated and further wherein:

$R^1$ is absent or present and, when present, is selected from the group consisting of $C_1$ to $C_{10}$ alkylene, $C_1$ to $C_{10}$ substituted alkylene, $C_2$ to $C_{10}$ alkenyl, $C_2$ to $C_{10}$ substituted alkenyl, $C_2$ to $C_{10}$ alkenylene, $C_2$ to $C_{10}$ substituted alkenylene, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenylene, substituted phenylene, naphthyl, substituted naphthyl, $C_7$ to $C_{12}$ phenylalkyl, $C_7$ to $C_{12}$ substituted phenylalkyl, heterocyclic ring, substituted heterocyclic ring, heteroaryl ring, substituted heteroaryl ring, amino, (monosubstituted)amino, a group of the formula: —$CH_2CONH$— and a group of the formula:

—$(CH_2)_p$—A—$(CH_2)_q$— wherein p and q are independently selected from a number 0 to 6, wherein both p and q are not both 0; and Ar is an aryl group selected from the group consisting of phenyl, substituted phenyl, heteroaryl ring and substituted heteroaryl ring;

$R^2$, $R^3$, and $R^4$ are, independently, selected from the group consisting of a hydrogen atom, halo, hydroxy, protected hydroxy, cyano, nitro, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, $C_2$ to $C_{10}$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^5$ is selected from the group consisting of a hydrogen atom, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_2$ to $C_{10}$ alkynyl, $C_2$ to $C_{10}$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, carboxy, protected carboxy, $C_1$ to $C_7$ acyl, $C_1$ to $C_7$ substituted acyl, heterocyclic ring, substituted heterocyclic ring, heteroaryl ring and substituted heteroaryl ring;

$R^6$ is selected from the group consisting of naphthyl, substituted naphthyl, a group of the formula:

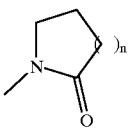

wherein n is from 1 to 2, and a group of the formula:

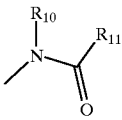

wherein $R_{10}$ and $R_{11}$ are, independently, selected from the group consisting of hydrogen, $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl, $C_1$ to $C_7$ acyl, $C_1$ to $C_7$ substituted acyl, $C_1$ to $C_4$ alkyl sulfoxide, phenylsulfoxide, substituted phenylsulfoxide, $C_1$ to $C_4$ alkylsulfonyl, phenylsulfonyl, and substituted phenylsulfonyl;

$R^7$ is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, phenyl, and substituted phenyl;

$R^9$ is absent or present and, when present, is selected from the group consisting of a hydrogen atom, $C_1$ to $C_{10}$ alkyl, $C_1$ to $C_{10}$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl, provided that when the ring is unsaturated, $R^9$ is absent; and Y is selected from the group consisting of $CO_2H$, OH, SH, $C(O)NHR^{12}$, $CH_2OH$, $CH_2NH_2$, and $CH_2NHR^{12}$, wherein $R^{12}$ is selected from the group consisting of a hydrogen atom, $C_1$ to $C_{10}$ alkyl and $C_1$ to $C_{10}$ substituted alkyl;

provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

42. A single compound of the formula:

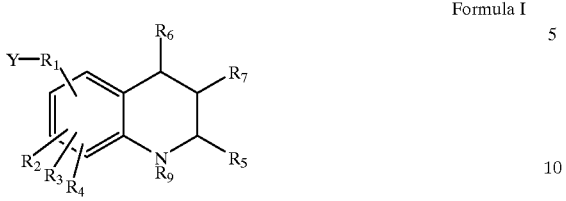

Formula I wherein:

R¹ is absent or present, and, when present, is selected from the group consisting of —CH₂NHCO— and CH₂CH(NHR⁸), wherein R⁸ is selected from the group consisting of acetyl, α-cyclohexylphenylacetyl, α-methylcinnamoyl, α,α,α-trifluoro-m-toluoyl, α,α,α-trifluoro-o-toluoyl, α,α,α-trifluoro-p-toluoyl, benzoyl, butyroyl, crotonoyl, cyclobutanecarboxyl, cycloheptanecarboxyl, cyclohexanebutyroyl, cyclohexanecarboxyl, cyclohexanepropionoyl, cyclohexylacetyl, cyclopentanecarboxyl, cyclopentylacetyl, ethoxyacetyl, 4-chlorocinnamoyl, 4-cyanobenzoyl, hydrocinnamoyl, 4-dimethylaminobenzoyl, 4-ethoxybenzoyl, isobutyroyl, isonicotinoyl, 4-ethoxyphenylacetyl, isovaleroyl, 4-ethylbenzoyl, m-anisoyl, m-toluoyl, m-tolylacetyl, methoxyacetyl, nicotinoyl, niflumoyl, o-anisoyl, o-toluoyl, octanoyl, p-anisoyl, p-toluoyl, p-tolylacetyl, phenoxyacetyl, phenylacetyl, picolinoyl, piperonoyl, propionoyl, pyrrole-2-carboxyl, 4-fluoro-α-methylphenylacetyl, -4-fluorobenzoyl, 4-fluorophenylacetyl, tert-butylacetyl, tigloyl, trans-3-(3-pyridyl)acroyl, trans-3-hexenoyl, trans-cinnamoyl, transstyrylacetyl, trimethylacetyl, triphenylacetyl, 4-isobutyl-α-methylphenylacetyl, -vinylacetyl, (2,5-dimethoxyphenyl)acetyl, (2-naphthoxy)acetyl, (3,4-dimethoxyphenyl)acetyl, (4-pyridylthio)acetyl, (α,α,α-trifluoro-m-tolyl)acetyl, (methylthio)acetyl, (phenylthio)acetyl, 1-(4-chlorophenyl)-1-cyclopentanecarboxyl, -1-adamantaneacetyl, 1-naphthylacetyl, 1-napthoyl, 1-phenyl-1-cyclopropanecarboxyl, 4-iodobenzoyl, 4-isopropoxybenzoyl, 2,3-dichlorobenzoyl, 4-methoxyphenylacetyl, 2,3-dimethoxybenzoyl, 2,4-dichlorobenzoyl, 2,4-difluorobenzoyl, 4-methyl-1-cyclohexanecarboxyl, 2,4-dimethoxybenzoyl, 2,4-dimethylbenzoyl, 2,4-hexadienoyl, 2,5-dichlorobenzoyl, 2,5-dimethylbenzoyl, 2,6-dichlorobenzoyl, 2,6-difluorobenzoyl, 4-methylcyclohexaneacetyl, 2,6-dimethoxybenzoyl, 2-(trifluoromethyl)-cinnamoyl, 4-methylvaleroyl, 2-bromobenzoyl, 2-chloro-4,5-difluorobenzoyl, 2-chloro-4-fluorophenylacetyl, 2-chlorobenzoyl, 2-ethoxybenzoyl, 2-ethyl-2-hexenoyl, 2-ethylbutyroyl, (+/−)-2-ethylhexanoyl, 2-fluorobenzoyl, 4-hydroxyquinoline-2-carboxyl, (+/−)-2-methylbutyroyl, 2-methylcyclopropanecarboxyl, 2-naphthylacetyl, 2-napthoyl, 2-norbornaneacetyl, 2-phenylbutyroyl, 2-propylpentanoyl, 3,3,3-triphenylpropionoyl, 3,3-diphenylpropionoyl, 3,4,5-triethoxybenzoyl, 3,4,5-trimethoxybenzoyl, 3,4,5-trimethoxycinnamoyl, 3,4-dichlorobenzoyl, 3,4-dichlorophenylacetyl, 3,4-difluorobenzoyl, 4-tert-butyl-cyclohexanecarboxyl, 3,4-dimethoxybenzoyl, 3,4-dimethylbenzoyl, 3,5,5-trimethylhexanoyl, 3,5-bis (trifluoromethyl)benzoyl, 5-bromo-2-chlorobenzoyl, 5-bromonicotinoyl, 5-phenylvaleroyl, 3,5-dichlorobenzoyl, 6-chloronicotinoyl, 3,5-dimethoxybenzoyl, 3,5-dimethyl-p-anisoyl, 3,5-dimethylbenzoyl, 3-(2-methoxyphenyl)propionoyl, 3-(3,4,5-trimethoxyphenyl)propionoyl, 3,4,5-trimethoxyphenylacetyl, 3-(3,4-dimethoxyphenyl)propionoyl, heptanoyl, 3-benzoylpropionoyl, 3-bromobenzoyl, 3-bromophenylacetyl, 3-chlorobenzoyl, 3-cyanobenzoyl, 3-cyclopentylpropionoyl, 3-dimethylaminobenzoyl, 3-fluoro-4-methylbenzoyl, 3-fluorobenzoyl, 3-fluorophenylacetyl, 6-methoxy-α-methyl-2-napthaleneacetyl, 3-iodo-4-methylbenzoyl, formyl, 6-methylnicotinoyl, lauryl, 3-methoxyphenylacetyl, 3 methylvaleroyl, 3-phenoxybenzoyl, 3-phenylbutyroyl, 4'-ethyl-4-biphenylcarboxyl, 4-(diethylamino)benzoyl, 4-benzoylbenzoyl, 4-biphenylacetyl, 4-biphenylcarboxyl, 4-bromobenzoyl, 4-bromophenylacetyl, 4-butylbenzoyl, 4-chloro-o-anisoyl, and 4-chlorobenzoyl;

R², R³, and R⁴ are, independently, selected from the group consisting of a hydrogen atom, hydroxy, fluoro, chloro, bromo, iodo, methyl, methoxy, nitro and —CH=CH—CH=CH— fused to adjacent positions;

R⁵ is selected from the group consisting of a hydrogen atom, phenyl, chloroacetyl, cyclohexanyl, D,L-1,2-(dihydroxy)ethyl, carboxy, acetyl, 2-hydroxyphenyl, tribromoacetyl, trimethylacetyl, 1-methyl-2-pyrrolyl, 1-napthyl, 2,3,4-trifluorophenyl, 2,3,5-trichlorophenyl, 2,3-difluorophenyl, 2,4-dichlorophenyl, 2,5-difluorophenyl, 2,5-dimethylphenyl, 2,6-difluorophenyl, 2-bromophenyl, 2-chloro-5-nitrophenyl, 2-chloro-6-fluorophenyl, 2-cyanophenyl, 2-ethylbutyryl, 2-fluorophenyl, 2-(2-oxymethylenecarboxy)phenyl, 2-methoxy-1-naphthyl, 2-nitro-5-chlorophenyl, 2-nitrophenyl, 2-pyridinyl, 3,4-(methylenedioxy)-6-nitrophenyl, 3,4-difluorophenyl, 3,5-bis(trifluoromethyl)phenyl, 3,5-dichlorophenyl, 3-(3,4-dichlorophenoxy)phenyl, 3-bromo-4-fluorophenyl, 3-bromophenyl, 3-carboxyphenyl, 3-cyanophenyl, 3-fluorophenyl, 3-hydroxyphenyl, 3-nitro-4-chlorophenyl, 3-nitrophenyl, 3-phenoxyphenyl, 3-phenylbutyryl, 3-pyridinyl, 4-bromophenyl, 4-carboxyphenyl, 4-cyanophenyl, 4-fluorophenyl, 4-nitrophenyl, 4-pyridinyl, 4-quinolinyl, 5-bromo-2-hydroxyphenyl, 5-norbornene-2-yl, 6-methyl-2-pyridinyl, 9-ethyl-3-carbazolyl, 2,3-dimethylvaleryl, 2,2-dimethyl-4-pentenyl, 3-methoxy-2-nitro-phenyl, 3-hydroxy-4-nitro-phenyl, 2-methylbutyryl, 2-methylvaleryl, 4-chloro-3-nitro-phenyl, 4-trifluromethyl)phenyl, 2-methylundecanyl, and β-phenylcinnaminyl;

R⁶ is selected from the group consisting of nalidixoyl, 2-phenyl-4-quinolinecarboxy, niflumoyl, 4-nitrophenylacetyl, 4-(4-nitrophenyl)butyroyl, (3,4-dimethoxyphenyl)-acetyl, 3,4-(methylenedioxy)phenylacetyl, 4-nitrocinnamoyl, 3,4,-(methylenedioxy)cinnamoyl, 3,4,5-trimethoxycinnamoyl, benzoyl, 2-chlorobenzoyl, 2-nitrobenzoyl, 2-(p-toluoyl)benzoyl, 2,4-dinitrophenylacetyl, 3-(3,4,5-trimethoxyphenyl)-propionyl, 4-biphenylacetyl, 1-napthylacetyl, (2-napthoxy)acetyl, trans-cinnamoyl, picolinyl, 3-amino-4-hydroxybenzoyl, (4-pyridylthio)acetyl, 2,4-dichlorobenzoyl, 3,4-dichlorobenzoyl, 4-biphenylcarboxy, 1-benzoylpropionyl, phenylacetyl, hydrocinnamoyl, 3,3-diphenylpropionyl, 3,3,3- triphenylpropionyl, 4-phenylbutyryl, phenoxyacetyl, (+/−)-2-phenoxypropionyl, 2,4-dimethoxybenzoyl, 3,4-dimethoxybenzoyl, 3,4-dihydroxybenzoyl, 2,4-dihydroxybenzoyl, 3,4,5-trimethoxybenzoyl, 3,4,5-triethoxybenzoyl, 3,4,5-trihydroxybenzoyl, 2-benzoylbenzoyl, 1-napthoyl, 4-chloro-2-nitrobenzoyl, 2-chloro-4-nitrobenzoyl, 4-chloro-3-nitrobenzoyl, 2-chloro-5-nitrobenzoyl, 4-dimethylaminobenzoyl, 4-(diethylamino)benzoyl, 4-nitrobenzoyl, 3-(dimethylamino)benzoyl, p-methylbenzoyl, p-methoxybenzoyl, trimethylacetyl, tert-butylacetyl, (−)-menthoxyacetyl, cyclohexanecarboxy, cyclohexylacetyl, dicyclohexylacetyl, 4-cyclohexylbutyroyl, cycloheptanecarboxy, 13-isopropylpodocarpa-7,13-dien-15-oyl, acetyl, octanoyl, (methylthio)acetyl, 3-nitropropionyl, 4-amino-3 hydroxybenzoyl, 3-(s)(−)-2-pyrrolidone-5-carboxy, 4-methoxy-2-quinolinecarboxy, 1-adamantanecarboxy, piperonoyl, 2-norbornaneacetyl, nicotinoyl, isonicotinoyl, 3α-hydroxy-5β-cholan-24-oyl, (3α,7α,12α)-trihydroxy-5β-cholan-24-oyl, (3α,5β-12α)-3,12, dihydroxy-5-cholan-24-oyl, (3α,5β,6α)-3,6-dihydroxy-cholan-24-oyl, L-alaninyl, L-cysteinyl, L-aspartinyl, L-glutaminyl, L-phenylalaninyl, glycinyl, L-isoleucinyl, L-lyscinyl, L-leucinyl, L-methionylsulfoxide, L-methionyl, L-asparginyl, L-prolinyl, L-glutaminyl, L-arganinyl, L-serinyl, L-threoninyl, L-valinyl, L-tyrosinyl, D-alaninyl, D-cysteinyl, D-aspartinyl, D-glutaminyl, D-phenylalaninyl, glycinyl, D-isoleucinyl, D-lyscinyl, D-leucinyl, D-methionylsulfoxide, D-methionyl, D-asparginyl, D-prolinyl, D-glutaminyl, D-arganinyl, D-serinyl, D-threoninyl, D-valinyl, D-tyrosinyl, 2-aminobutyroyl, 4-aminobutyroyl, 2-aminoisobutyroyl, L-norleucinyl, D-norleucinyl, 6-aminohexanoyl, 7-aminoheptanoyl, thioprolinyl, L-norvalinyl, D-norvalinyl, α-ornithinyl, methionyl sulfonyl, L-naphthylalaninyl, D-naphthylalaninyl, L-phenylglycinyl, D-phenylglycinyl, β-alaninyl, L-cyclohexylalaninyl, D-cyclohexylalaninyl, hydroxyprolinyl, 4-nitrophenylalaninyl, dehydroprolinyl, 3-hydroxy-1-propanesulfonyl, 1-propanesulfonyl, 1-octanesulfonyl, perfluoro-1-octanesulfonyl, (+)-10-camphorsulfonyl, (−)-10-camphorsulfonyl, benzenesulfonyl, 2-nitrobenzenesulfonyl, p-toluenesulfonyl, 4-nitrobenzenesulfonyl, n-acetylsulfanilyl, 2,5-dichlorobenzenesulfonyl, 2,4-dinitrobenzenesulfonyl, 2-mesitylenesulfonyl and 2-napthalenesulfonyl;

$R^7$ is selected from the group consisting of a hydrogen atom and methyl;

$R^9$ is a hydrogen atom; and

Y is $C(O)NHR^{12}$, wherein $R^{12}$ is a hydrogen atom, provided said ring of said heterocyclic ring, substituted heterocyclic ring, heteroaryl ring or substituted heteroaryl ring contains one ring nitrogen atom and four or five ring carbon atoms; and provided said cyclic $C_2$ to $C_7$ heteroalkylene and substituted cyclic $C_2$ to $C_7$ heteroalkylene are, respectively, quinolyl and substituted quinolyl;

or a salt of the 4-substituted quinoline.

\* \* \* \* \*